US011566257B2

(12) United States Patent
Fu et al.

(10) Patent No.: US 11,566,257 B2
(45) Date of Patent: Jan. 31, 2023

(54) **USE OF YR4DS GENE OF *AEGILOPS TAUSCHII* IN STRIPE RUST RESISTANCE BREEDING OF TRITICEAE PLANTS**

(71) Applicants: SHANDONG AGRICULTURAL UNIVERSITY, Shandong (CN); SICHUAN AGRICULTURAL UNIVERSITY, Sichuan (CN)

(72) Inventors: Daolin Fu, Taian (CN); Chaozhong Zhang, Taian (CN); Dengcai Liu, Chengdu (CN); Lin Huang, Chengdu (CN); Jiajie Wu, Taian (CN); Huifei Zhang, Taian (CN); Fei Ni, Taian (CN); Lianquan Zhang, Chengdu (CN); Ge Gao, Taian (CN)

(73) Assignees: SHANDONG AGRICULTURAL UNIVERSITY, Taian (CN); SICHUAN AGRICULTURAL UNIVERSITY, Chengdu (CN)

( * ) Notice: Subject to any disclaimer, the term of this patent is extended or adjusted under 35 U.S.C. 154(b) by 0 days.

(21) Appl. No.: 15/734,088

(22) PCT Filed: Apr. 29, 2019

(86) PCT No.: PCT/CN2019/084906
§ 371 (c)(1),
(2) Date: Dec. 1, 2020

(87) PCT Pub. No.: WO2019/228118
PCT Pub. Date: Dec. 5, 2019

(65) Prior Publication Data

US 2021/0403936 A1 Dec. 30, 2021

(30) Foreign Application Priority Data

Jun. 1, 2018 (CN) ........................ 201810555355.5
Nov. 27, 2018 (CN) ........................ 201811424853.2

(51) Int. Cl.
*C12N 15/82* (2006.01)
*C12Q 1/6895* (2018.01)
*A01H 6/46* (2018.01)

(52) U.S. Cl.
CPC ..... *C12N 15/8282* (2013.01); *C12N 15/8218* (2013.01); *C12Q 1/6895* (2013.01); *C12Q 2600/13* (2013.01)

(58) Field of Classification Search
None
See application file for complete search history.

(56) References Cited

FOREIGN PATENT DOCUMENTS

CN 101760547 A 6/2010
CN 102505016 A 6/2012
CN 105695605 A 6/2016
CN 108004346 A 5/2018
CN 109321582 A 2/2019
WO 2015/036995 A1 3/2015

OTHER PUBLICATIONS

Liu et al (2013, Crop Science, 53:2014-2020.*
X. M. Chen. "Epidemiology and Control of Stripe Rust [*Puccinia striiformis* F. Sp. Tritici] on Wheat". Canadian Journal of Plant Pathology, vol. 27, 2005, pp. 314-337.
Wan-quan Chen et al. "Integrated Management of Wheat Stripe Rust Caused by *Puccinia striiformis* F. Sp. Tritici in China". Scientia Agricultura Sinica, vol. 46., No. 20, 2013, pp. 4254-4262.
Zhen-sheng Kang et al. "Advances in Research of Pathogenicity and Virulence Variation of the Wheat Stripe Rust Fungus *Puccinia striiformis* F. Sp. Tritici". Scientia Agricultura Sinica, vol. 48, No. 17, 2015, pp. 3439-3453.
Daolin Fu et al. "A Kinase-Start Gene Confers Temperature-Dependent Resistance to Wheat Stripe Rust". Science Magazine, vol. 323, Mar. 6, 2009, pp. 1357-1360.
Simon G. Krattinger et al. "A Putative ABC Transporter Confers Durable Resistance to Multiple Fungal Pathogens in Wheat". Science Magazine, vol. 323, Mar. 6, 2009, pp. 1360-1363.
Clemence Marchal et al. "Bed-Domain Containing Immune Receptors Confer Diverse Resistance Spectra to Yellow Rust". Nature Plants, vol. 4, 2018, 47 pages.
Valentina Klymiuk et al. "Cloning of the Wheat Yr15 Resistance Gene Sheds Light on the Plant Tandem Kinase-Pseudokinase Family". Nature Communications, vol. 9, 2018, 12 pages.
Joseph K. Cheng et al. "The Genome Editing Toolbox: a Spectrum of Approaches for Targeted Modification". Current Opinion in Biotechnology, vol. 30, 2014, pp. 87-94.
Qiwei Shan et al. "Genome Editing in Rice and Wheat Using the CRISPR/CAS Sytem". Nature Protocols, vol. 9, No. 10, 2014, pp. 2395-2410.
Yanpeng Wang et al. "Simultaneous Editing of Three Homoeoalleles in Hexaploid Bread Wheat Confers Heritable Resistance to Powdery Mildew". Nature Biotechnology, vol. 32, No. 9, Sep. 2014, pp. 947-951.
Yi Zhang et al. "Efficient and Transgene-Free Genome Editing in Wheat Through Transient Expression of CRISPR/CAS9 DNA or RNA". Nature Communications, vol. 7, 2016, 8 pages.
Ann J Slade et al. "A Reverse Genetic, Nontransgenic Approach to Wheat Crop Improvement by Tilling". Nature Biotechnology, vol. 23, 2005, pp. 75-81.
Bradley J Till et al. "A Protocol for Tilling and Ecotilling in Plants and Animals". Nature Protocols, vol. 1, No. 5, 2006, pp. 2465-2477.
Randall K. Saiki et al. "Enzymatic Amplification of [beta]-Globin Genomic Sequences and Restriction Site Analysis for Diagnosis of Sickle Cell Anemia". Science Magazine, vol. 230, 1985, pp. 1350-1354.

(Continued)

*Primary Examiner* — Jason Deveau Rosen
(74) *Attorney, Agent, or Firm* — Oliff PLC

(57) ABSTRACT

A Yr4DS gene of *Aegilops tauschii* and its use thereof in stripe rust resistance breeding of Triticeae plants. Said gene has a sequence as shown in SEQ ID NO. 1, SEQ ID NO. 3, SEQ ID NO. 5, SEQ ID NO. 7, SEQ ID NO. 9, or SEQ ID NO. 10.

17 Claims, 3 Drawing Sheets

Specification includes a Sequence Listing.

(56) References Cited

OTHER PUBLICATIONS

Anne Hemsley et al. "A Simple Method for Site-Directed Mutagenesis Using the Polymerase Chain Reaction". Nucleic Acids Research, vol. 17, 1989, pp. 6545-6551.
Olfert Landt et al. "A General Method for Rapid Site-Directed Mutagenesis Using the Polymerase Chain Reaction". Gene, vol. 96, 1990, pp. 125-128.
Sriram Kosuri et al. "Large-Scale De Novo DNA Synthesis: Technologies and Applications". Nature Methods, vol. 11, No. 5, May 2014, pp. 499-507.
Stephen F. Altschul et al. "Basic Local Alignment Search Tool". Journal of Molecular Biology, vol. 215, 1990, pp. 403-410.
Samuel Karlin et al. "Applications and Statistics for Multiple High-Scoring Segments in Molecular Sequences". Proceedings of the National Academy of Sciences, vol. 90, Jun. 1993, pp. 5873-5877.
Alan H. Christensen et al. "Maize Polyubiquitin Genes: Structure, Thermal Perturbation of Expression and Transcript Splicing, and Promoter Activity Following Transfer to Protoplasts by Electroporation". Plant Molecular Biology, vol. 18, 1992, pp. 675-689.
Brian J. Haas et al. "De Novo Transcript Sequence Reconstruction From RNA-SEQ: Reference Generation and Analysis With Trinity". Nature Protocols, vol. 8, Aug. 2013, 44 pages.
Jetty S.S. Ammiraju et al. "Random Sheared FOSMID Library as a New Genomic Tool to Accelerate Complete Finishing of Rice (*Oryza sativa* Spp. Nipponbare) Genome Sequence: Sequencing of Gap-Specific FOSMID Clones Uncovers New Euchromatic Portions of the Genome". Theor. Appl. Genet., vol. 111, 2005, pp. 1596-1607.
Lian-Quan Zhang et al. "Frequent Occurrence of Unreduced Gametes in Triticum turgidum-Aegilops tauschii Hybrids". Euphytica, vol. 172, 2010, pp. 285-294.
Miao Liu et al. "Stripe Rust Resistance in Aegilops tauschii Germplasm". Crop Science, vol. 53, 2013, pp. 2014-2020.
Cuiling Yuan et al. "Distribution, Frequency and Variation of Stripe Rust Resistance Loci Yr10, Lr34/Yr18 and Yr36 in Chinese Wheat Cultivars". Journal of Genetics and Genomics, vol. 39, 2012, pp. 587-592.
Fei Ni et al. "Wheat Ms2 Encodes for an Orphan Protein That Confers Male Sterility in Grass Species". Nature Communications, vol. 8, 2017, 12 pages.
Ksenia V. Krasileva et al. "Uncovering Hidden Variation in Polyploid Wheat". PNAS, vol. 114, 2017, pp. E913-E921.
M. De Block et al. "Engineering Herbicide Resistance in Plants by Expression of a Detoxifying Enzyme". The EMBO Journal, vol. 6, No. 9, 1987, pp. 2513-2518.
Bo Lv et al. "Characterization of Flowering Locus T1 (FT1) Gene in Brachypodium and Wheat". Plos One, vol. 9, issue 4, Apr. 2014, pp. e94171.
Qunqun Hao et al. "Isochorismate-Based Salicylic Acid Biosynthesis Confers Basal Resistance to Fusarium Graminearum in Barley". Molecular Plant Pathology, vol. 19, No. 8, 2018, pp. 1995-2010.
Haiquan Zhang et al. "Intraspecific Hybridization Among Aegilops tauschii Varieties & Genetic Analysis and Molecular Markers of a Novel Stripe Rust Resistance Gene From A. tauschii". Chinese Journal of Applied Environmental Biology, vol. 15, No. 1, 2009, pp. 044-047.
Lin Huang et al. "Molecular Tagging of a Stripe Rust Resistance Gene in Aegilops tauschii". Euphytica, vol. 179, 2011, pp. 313-318.
Hai-quan Zhang et al. "Identification and SSR Mapping of Stripe Rust Resistance Gene in Ae. tauschii". Journal of Northwest A & F University (Nat. Sci. Ed.), vol. 36, No. 9, Sep. 2008, pp. 156-160, 168.
Vasu Kuraparthy et al. "Characterization and Mapping of Cryptic Alien Introgression From Aegilops geniculata With New Leaf Rust and Stripe Rust Resistance Genes Lr57 And Yr40 in Wheat". Theor. Appl. Genet., vol. 114, 2007, pp. 1379-1389.
Wei Liu et al. "The Stripe Rust Resistance Gene Yr10 Encodes an Evolutionary-Conserved and Unique CC-NBS-LRR Sequence in Wheat". Molecular Plant, vol. 7, Dec. 2014, pp. 1740-1755.
Aug. 1, 2019 International Search Report issued in International Patent Application No. PCT/CN2019/084906.
Dec. 1, 2020 International Preliminary Report on Patentability issued in International Patent Application No. PCT/CN2019/084906.

* cited by examiner

SEQUENCE LISTING

```
<160> NUMBER OF SEQ ID NOS: 63

<210> SEQ ID NO 1
<211> LENGTH: 4266
<212> TYPE: DNA
<213> ORGANISM: Aegilops tauschii

<400> SEQUENCE: 1
```

-continued

```
gcagctccac ctaccgcagc tggccggtcg tcggtccttg catcgcatcc aaggcgacgc     60
cggctccacc actgccgcca ccactgattg gtaccttaag ctcccgtgaa gctacaaggg    120
aggaggcccc ctcgcctccc atccattgtt cctcaacagc ttgggtgccg agctccccca    180
ccaccacact agacgcgctg ggattcattg gatccgctcc agcgagcgag ccggattcag    240
ttcaccgaga ttatattcac ccttcccgtc tgccaactga ttacctccct tttcccattc    300
taccctgggt gaccactctg ctcactctca ctctttcttt ctcctctacg ccggccgtgc    360
acagcgcgac gccgacgacc gcatcccccc gacgttgccg cagccgccat acaagtagaa    420
ggaccgagat ggcaacctct cccagctttg tgctacaccg caagtactag gagcattgct    480
gaatgccgga tatagatccc cagatctagg ccaagggtct cgctttctgc tcactgttac    540
ttctatcatc tctccaatcg atccaagttc cagctcaagc cactggaccc tgcaactact    600
tgcgagacag cacgggatat ctatctctgc aacaagatcc gtctctcatc tctctagtcg    660
attcaagtac tagttcaagc gtgagcaaac cctgcaacca atggcggggg ttctggatgc    720
tttggcatcc tacgtgacca acatgctcac cgagatggct aaagaggagg tggccatgct    780
aatcggcgtg tctgacggga tcaaagacct aagcatcaag cttggggacc tcaagaattt    840
ccttgctgat gctgatagga ggaacattac cgatgatagt gtgcgggggt gggtgggcga    900
actgaagcgt gccatgtact tggccactga catcgtcgac ctatgtcagc tcaaggccat    960
ggagcaaggt caaacaaagg acagggcgtg ccggtgcctt aaccctctgc tcttttgcat   1020
gcggaatccc ctccacgccc acgacatcgg cacccgcatc aagctgctca accaaaattt   1080
ggatgatatt tgcaagaggg gcagcagttt caatttcatc aagctagaag cctaccaaga   1140
ccaaaagacc actcggtctc ccgccactga ccggaaaaca aattcactga ttgagcggtc   1200
cggtgtggtt ggagagaaga tcgaggagga cacgagggca cttgtggagg tgcttacaag   1260
ggaggcggta ggtgacaaga gtggtcgcct cattgtggtc gccattgttg gtatcggagg   1320
gattggtaag actaccctcg gcaagaaggt cttcaatgat gaggccatcg aaggcaagtt   1380
tactaagaag atatggctta gcatcacaca agatttcacc gatgttgagt tgttaagtac   1440
gaccatcact gccattgggg cagatcttcc tggagggggt ggggctccag acaaggccct   1500
acttgtcgat gctctcaaga acgccatcaa ggacaagaag ttctttcttg tactagatga   1560
cctgtgggat gtcgatgcat ggaacaaaca tctaatgact ccctttagct atggtggccc   1620
cggtagtaga gtcctcatca ccaccagaca tgacactgta gcccgaagca tgaaagcctt   1680
tcatccctac catcatgttg acaaattagc tccacaagat gcttggtcgt tgctcaagaa   1740
gcaggtagtc acaggagagg aaaatgaacc agaagttgat atgctagaag atattgggct   1800
gcagattata gcaaaatgtg atggcttacc acttgctgta aaagttatgg gtggactcct   1860
atgcaagaag gagaaaacac gacgtgattg gcaagacgtc ttgaatgatg atatgtggtc   1920
agtatctcaa atgtcaaagg aactaaatta tgccatatat cttagctatg aggatttgtc   1980
cccttactta aaacagtgct tcttgcactt ctccctcaaa ccaaaaaaga cagtgataac   2040
tgatactgaa atggtgtcca tgtgggttgg tgaaggattg gttgaaggag acacatatac   2100
tcgtagtttg gaagaaggga ataagtacta taaggagcta atagtaagga accttataga   2160
ggtagataca aagtacccta gtcaacttat ttgcaacatg catgatgtta ttcgctcatt   2220
tgctcaattt gtggctaggg atgaaacact agtaggtcac aatggagata ctatcaaaac   2280
aaatcttaga tcaccgaatt atcttagatt atccatagaa acgaaaggag tgggatccga   2340
```

-continued

```
tgaatttgag tggagatatt taagagagca aaaattgctt aggtctctaa tattaactgg   2400

aaacctcaaa agtcagcctg gggattcgtt gactatcttc ccaagtctac gtcttttgca   2460

tatagaatca gcaaatattg ctgcactagt tgaatctatg taccaactca agcatttgag   2520

atatttggca ttaaagagga ctgatatgtg tagactacca gagaacatcc atgagatgaa   2580

attcctacag catattagcc ttgaaggttg tgaaagtttc atgaaacttc ctgatagtat   2640

tatcaagctg caagggttga gatatcttga tatgggtgac acacgtgtaa gtagtattcc   2700

taggggtttc cgagctctta caaatttgac ttcactattt gggtttccag cctatattga   2760

tggtgactgg tgtagtctgg aagagttggg gtctctttcc cagctcaatg aactttcact   2820

acagagccta gaaaatgtat ctagtgcctt gttggctgaa aaggcaaggg taaatgcaaa   2880

gaaacaactt accgtacttg ctttaaaatg tggtggtaga gtgggacatg ggttggtcca   2940

aggagaggtc tctgagtcta aggaggagga gcaaataatt gaggcggtgt ttgatgtgct   3000

ctgtcctcag ccttgcatag aacacatcag aatagaaaga tattttggtc gtcggctccc   3060

aggatggatg gcgtccacag ctatggtgcc cctcgagagc ttgaagattc tatgcctcga   3120

acacctgccc tgctgcaccc aactcccaga tggcttgtgc aggctcccgt atttggagtg   3180

gataaaagtg atgaatgctc cagtaatcaa gtgtattggt cctgaattcg ttcaacagta   3240

caatcagctg caccgtcctt catctcagtt ggctgctacg tttcccaaac tccagatgtt   3300

ggaatttcac ggaatggagg aatgggagga gtgggtttgg gagacggaag tgaaagctat   3360

gcccttattg gaggaacttc gtatcacttc ttgcagactg agccgtatgc ctccaggact   3420

tatgtctcat gcaatggctt tgaagaagct aacaatatgg agcgtccaat gtctccactc   3480

tctagagaac tttgtttctg tagttgaact cgaattggga aacatacctg aactggccat   3540

gatctccaat cttccaaaat tacaaaaact tacaatcgag tgctgcccaa agctcgagat   3600

gctgcaggag atggctgcac tccggagact cgagctgacc attttcaaca gcgaaaatca   3660

acttccggtc tacctgcaga ctgtgaagcc tagtaatttg ctgctgacct gcaacctagc   3720

ggtactcact tccatggctg agggtgaatc tagctccgag tgggacaagt tcagtcatat   3780

caaccacgtt gaggcttatg cagaggatgg agaagatgag aagaaatggc acgtgttcta   3840

cacatctgaa tcctgcaaca tagagacaaa tattcatcag gatcgattgg tcgaagaaga   3900

ggagtaggct gaaactccag ccgaacgagg aaggaccata tgatgcaagg atatataagt   3960

atgtctgctg ttacaacttc aactagtttt gagatcgaat ccatgaaggg atacggggaa   4020

aagcatcagc cataatgcca tatacactta cctgcagaga ttcacacatc atactaattt   4080

cttgtgaagt gtgacatata cagttacgaa tttagagatg taaacttcgt ggcggactat   4140

ccagctggtg aagaaacatg gtgaccttgg caaggctctc ctttgtttag tgcaagcaac   4200

taatggagtt tagactactc tgctttgctc tgctctctga aagcagctca ggttgcaggt   4260

cctctg                                                              4266
```

```
<210> SEQ ID NO 2
<211> LENGTH: 1068
<212> TYPE: PRT
<213> ORGANISM: Aegilops tauschii

<400> SEQUENCE: 2

Met Ala Gly Val Leu Asp Ala Leu Ala Ser Tyr Val Thr Asn Met Leu
1               5                   10                  15

Thr Glu Met Ala Lys Glu Glu Val Ala Met Leu Ile Gly Val Ser Asp
            20                  25                  30
```

-continued

```
Gly Ile Lys Asp Leu Ser Ile Lys Leu Gly Asp Leu Lys Asn Phe Leu
        35                  40                  45

Ala Asp Ala Asp Arg Arg Asn Ile Thr Asp Asp Ser Val Arg Gly Trp
    50                  55                  60

Val Gly Glu Leu Lys Arg Ala Met Tyr Leu Ala Thr Asp Ile Val Asp
65                  70                  75                  80

Leu Cys Gln Leu Lys Ala Met Glu Gln Gly Gln Thr Lys Asp Arg Ala
                85                  90                  95

Cys Arg Cys Leu Asn Pro Leu Leu Phe Cys Met Arg Asn Pro Leu His
            100                 105                 110

Ala His Asp Ile Gly Thr Arg Ile Lys Leu Leu Asn Gln Asn Leu Asp
        115                 120                 125

Asp Ile Cys Lys Arg Gly Ser Ser Phe Asn Phe Ile Lys Leu Glu Ala
    130                 135                 140

Tyr Gln Asp Gln Lys Thr Thr Arg Ser Pro Ala Thr Asp Arg Lys Thr
145                 150                 155                 160

Asn Ser Leu Ile Glu Arg Ser Gly Val Val Gly Glu Lys Ile Glu Glu
                165                 170                 175

Asp Thr Arg Ala Leu Val Glu Val Leu Thr Arg Glu Ala Val Gly Asp
            180                 185                 190

Lys Ser Gly Arg Leu Ile Val Val Ala Ile Val Gly Ile Gly Gly Ile
        195                 200                 205

Gly Lys Thr Thr Leu Gly Lys Lys Val Phe Asn Asp Glu Ala Ile Glu
    210                 215                 220

Gly Lys Phe Thr Lys Lys Ile Trp Leu Ser Ile Thr Gln Asp Phe Thr
225                 230                 235                 240

Asp Val Glu Leu Leu Ser Thr Thr Ile Thr Ala Ile Gly Ala Asp Leu
                245                 250                 255

Pro Gly Gly Gly Gly Ala Pro Asp Lys Ala Leu Leu Val Asp Ala Leu
            260                 265                 270

Lys Asn Ala Ile Lys Asp Lys Lys Phe Phe Leu Val Leu Asp Asp Leu
        275                 280                 285

Trp Asp Val Asp Ala Trp Asn Lys His Leu Met Thr Pro Phe Ser Tyr
    290                 295                 300

Gly Gly Pro Gly Ser Arg Val Leu Ile Thr Thr Arg His Asp Thr Val
305                 310                 315                 320

Ala Arg Ser Met Lys Ala Phe His Pro Tyr His His Val Asp Lys Leu
                325                 330                 335

Ala Pro Gln Asp Ala Trp Ser Leu Leu Lys Lys Gln Val Val Thr Gly
            340                 345                 350

Glu Glu Asn Glu Pro Glu Val Asp Met Leu Glu Asp Ile Gly Leu Gln
        355                 360                 365

Ile Ile Ala Lys Cys Asp Gly Leu Pro Leu Ala Val Lys Val Met Gly
    370                 375                 380

Gly Leu Leu Cys Lys Lys Glu Lys Thr Arg Arg Asp Trp Gln Asp Val
385                 390                 395                 400

Leu Asn Asp Asp Met Trp Ser Val Ser Gln Met Ser Lys Glu Leu Asn
                405                 410                 415

Tyr Ala Ile Tyr Leu Ser Tyr Glu Asp Leu Ser Pro Tyr Leu Lys Gln
            420                 425                 430

Cys Phe Leu His Phe Ser Leu Lys Pro Lys Lys Thr Val Ile Thr Asp
        435                 440                 445
```

-continued

```
Thr Glu Met Val Ser Met Trp Val Gly Glu Gly Leu Val Glu Gly Asp
    450                 455                 460

Thr Tyr Thr Arg Ser Leu Glu Glu Gly Asn Lys Tyr Tyr Lys Glu Leu
465                 470                 475                 480

Ile Val Arg Asn Leu Ile Glu Val Asp Thr Lys Tyr Pro Ser Gln Leu
                485                 490                 495

Ile Cys Asn Met His Asp Val Ile Arg Ser Phe Ala Gln Phe Val Ala
            500                 505                 510

Arg Asp Glu Thr Leu Val Gly His Asn Gly Asp Thr Ile Lys Thr Asn
        515                 520                 525

Leu Arg Ser Pro Asn Tyr Leu Arg Leu Ser Ile Glu Thr Lys Gly Val
    530                 535                 540

Gly Ser Asp Glu Phe Glu Trp Arg Tyr Leu Arg Glu Gln Lys Leu Leu
545                 550                 555                 560

Arg Ser Leu Ile Leu Thr Gly Asn Leu Lys Ser Gln Pro Gly Asp Ser
                565                 570                 575

Leu Thr Ile Phe Pro Ser Leu Arg Leu Leu His Ile Glu Ser Ala Asn
            580                 585                 590

Ile Ala Ala Leu Val Glu Ser Met Tyr Gln Leu Lys His Leu Arg Tyr
        595                 600                 605

Leu Ala Leu Lys Arg Thr Asp Met Cys Arg Leu Pro Glu Asn Ile His
    610                 615                 620

Glu Met Lys Phe Leu Gln His Ile Ser Leu Glu Gly Cys Glu Ser Phe
625                 630                 635                 640

Met Lys Leu Pro Asp Ser Ile Ile Lys Leu Gln Gly Leu Arg Tyr Leu
                645                 650                 655

Asp Met Gly Asp Thr Arg Val Ser Ser Ile Pro Arg Gly Phe Arg Ala
            660                 665                 670

Leu Thr Asn Leu Thr Ser Leu Phe Gly Phe Pro Ala Tyr Ile Asp Gly
        675                 680                 685

Asp Trp Cys Ser Leu Glu Glu Leu Gly Ser Leu Ser Gln Leu Asn Glu
    690                 695                 700

Leu Ser Leu Gln Ser Leu Glu Asn Val Ser Ser Ala Leu Leu Ala Glu
705                 710                 715                 720

Lys Ala Arg Val Asn Ala Lys Lys Gln Leu Thr Val Leu Ala Leu Lys
                725                 730                 735

Cys Gly Gly Arg Val Gly His Gly Leu Val Gln Gly Glu Val Ser Glu
            740                 745                 750

Ser Lys Glu Glu Glu Gln Ile Ile Glu Ala Val Phe Asp Val Leu Cys
        755                 760                 765

Pro Gln Pro Cys Ile Glu His Ile Arg Ile Glu Arg Tyr Phe Gly Arg
    770                 775                 780

Arg Leu Pro Gly Trp Met Ala Ser Thr Ala Met Val Pro Leu Glu Ser
785                 790                 795                 800

Leu Lys Ile Leu Cys Leu Glu His Leu Pro Cys Cys Thr Gln Leu Pro
                805                 810                 815

Asp Gly Leu Cys Arg Leu Pro Tyr Leu Glu Trp Ile Lys Val Met Asn
            820                 825                 830

Ala Pro Val Ile Lys Cys Ile Gly Pro Glu Phe Val Gln Gln Tyr Asn
        835                 840                 845

Gln Leu His Arg Pro Ser Ser Gln Leu Ala Ala Thr Phe Pro Lys Leu
    850                 855                 860

Gln Met Leu Glu Phe His Gly Met Glu Glu Trp Glu Glu Trp Val Trp
```

-continued

```
865                 870                 875                 880

Glu Thr Glu Val Lys Ala Met Pro Leu Leu Glu Glu Leu Arg Ile Thr
                885                 890                 895

Ser Cys Arg Leu Ser Arg Met Pro Pro Gly Leu Met Ser His Ala Met
            900                 905                 910

Ala Leu Lys Lys Leu Thr Ile Trp Ser Val Gln Cys Leu His Ser Leu
        915                 920                 925

Glu Asn Phe Val Ser Val Val Glu Leu Glu Leu Gly Asn Ile Pro Glu
    930                 935                 940

Leu Ala Met Ile Ser Asn Leu Pro Lys Leu Gln Lys Leu Thr Ile Glu
945                 950                 955                 960

Cys Cys Pro Lys Leu Glu Met Leu Gln Glu Met Ala Ala Leu Arg Arg
                965                 970                 975

Leu Glu Leu Thr Ile Phe Asn Ser Glu Asn Gln Leu Pro Val Tyr Leu
            980                 985                 990

Gln Thr Val Lys Pro Ser Asn Leu  Leu Leu Thr Cys Asn  Leu Ala Val
        995                 1000                1005

Leu Thr  Ser Met Ala Glu Gly  Glu Ser Ser Ser Glu  Trp Asp Lys
    1010                1015                1020

Phe Ser  His Ile Asn His Val  Glu Ala Tyr Ala Glu  Asp Gly Glu
    1025                1030                1035

Asp Glu  Lys Lys Trp His Val  Phe Tyr Thr Ser Glu  Ser Cys Asn
    1040                1045                1050

Ile Glu  Thr Asn Ile His Gln  Asp Arg Leu Val Glu  Glu Glu Glu
    1055                1060                1065


<210> SEQ ID NO 3
<211> LENGTH: 3477
<212> TYPE: DNA
<213> ORGANISM: Aegilops tauschii

<400> SEQUENCE: 3

gcagctccac ctaccgcagc tggccggtcg tcggtccttg catcgcatcc aaggcgacgc     60

cggctccacc actgccgcca ccactgattg gtaccttaag ctcccgtgaa gctacaaggg    120

aggaggcccc ctcgcctccc atccattgtt cctcaacagc ttgggtgccg agctccccca    180

ccaccacact agacgcgctg ggattcattg gatccgctcc agcgagcgag ccggattcag    240

ttcaccgaga ttatattcac ccttcccgtc tgccaactga ttacctccct tttcccattc    300

taccctgggt gaccactctg ctcactctca ctctttcttt ctcctctacg ccggccgtgc    360

acagcgcgac gccgacgacc gcatcccccc gacgttgccg cagccgccat acaagtagaa    420

ggaccgagat ggcaacctct cccagctttg tgctacaccg caagtactag gagcattgct    480

gaatgccgga tatagatccc cagatctagg ccaagggtct cgctttctgc tcactgttac    540

ttctatcatc tctccaatcg atccaagttc cagctcaagc cactggaccc tgcaactact    600

tgcgagacag cacgggatat ctatctctgc aacaagatcc gtctctcatc tctctagtcg    660

attcaagtac tagttcaagc gtgagcaaac cctgcaacca atggcggggg ttctggatgc    720

tttggcatcc tacgtgacca acatgctcac cgagatggct aaagaggagg tggccatgct    780

aatcggcgtg tctgacggga tcaaagacct aagcatcaag cttggggacc tcaagaattt    840

ccttgctgat gctgatagga ggaacattac cgatgatagt gtgcgggggt gggtgggcga    900

actgaagcgt gccatgtact tggccactga catcgtcgac ctatgtcagc tcaaggccat    960

ggagcaaggt caaacaaagg acagggcgtg ccggtgcctt aaccctctgc tcttttgcat   1020
```

gcggaatccc ctccacgccc acgacatcgg cacccgcatc aagctgctca accaaaattt 1080
ggatgatatt tgcaagaggg gcagcagttt caatttcatc aagctagaag cctaccaaga 1140
ccaaaagacc actcggtctc ccgccactga ccggaaaaca aattcactga ttgagcggtc 1200
cggtgtggtt ggagagaaga tcgaggagga cacgagggca cttgtggagg tgcttacaag 1260
ggaggcggta ggtgacaaga gtggtcgcct cattgtggtc gccattgttg gtatcggagg 1320
gattggtaag actaccctcg gcaagaaggt cttcaatgat gaggccatcg aaggcaagtt 1380
tactaagaag atatggctta gcatcacaca agatttcacc gatgttgagt tgttaagtac 1440
gaccatcact gccattgggg cagatcttcc tggagggggt ggggctccag acaaggccct 1500
acttgtcgat gctctcaaga acgccatcaa ggacaagaag ttctttcttg tactagatga 1560
cctgtgggat gtcgatgcat ggaacaaaca tctaatgact ccctttagct atggtggccc 1620
cggtagtaga gtcctcatca ccaccagaca tgacactgta gcccgaagca tgaaagcctt 1680
tcatccctac catcatgttg acaaattagc tccacaagat gcttggtcgt tgctcaagaa 1740
gcaggtagtc acaggagagg aaaatgaacc agaagttgat atgctagaag atattgggct 1800
gcagattata gcaaaatgtg atggcttacc acttgctgta aaagttatgg gtggactcct 1860
atgcaagaag gagaaaacac gacgtgattg gcaagacgtc ttgaatgatg atatgtgcct 1920
atattgatgg tgactggtgt agtctggaag agttggggtc tctttcccag ctcaatgaac 1980
tttcactaca gagcctagaa aatgtatcta gtgccttgtt ggctgaaaag gcaagggtaa 2040
atgcaaagaa acaacttacc gtacttgctt taaaatgtgg tggtagagtg ggacatgggt 2100
tggtccaagg agaggtctct gagtctaagg aggaggagca aataattgag gcggtgtttg 2160
atgtgctctg tcctcagcct tgcatagaac acatcagaat agaaagatat tttggtcgtc 2220
ggctcccagg atggatggcg tccacagcta tggtgcccct cgagagcttg aagattctat 2280
gcctcgaaca cctgccctgc tgcacccaac tcccagatgg cttgtgcagg ctcccgtatt 2340
tggagtggat aaaagtgatg aatgctccag taatcaagtg tattggtcct gaattcgttc 2400
aacagtacaa tcagctgcac cgtccttcat ctcagttggc tgctacgttt cccaaactcc 2460
agatgttgga atttcacgga atggaggaat gggaggagtg ggtttgggag acggaagtga 2520
aagctatgcc cttattggag gaacttcgta tcacttcttg cagactgagc cgtatgcctc 2580
caggacttat gtctcatgca atggctttga agaagctaac aatatggagc gtccaatgtc 2640
tccactctct agagaacttt gtttctgtag ttgaactcga attgggaaac atacctgaac 2700
tggccatgat ctccaatctt ccaaaattac aaaaacttac aatcgagtgc tgcccaaagc 2760
tcgagatgct gcaggagatg gctgcactcc ggagactcga gctgaccatt ttcaacagcg 2820
aaaatcaact tccggtctac ctgcagactg tgaagcctag taatttgctg ctgacctgca 2880
acctagcggt actcacttcc atggctgagg gtgaatctag ctccgagtgg gacaagttca 2940
gtcatatcaa ccacgttgag gcttatgcag aggatggaga agatgagaag aaatggcacg 3000
tgttctacac atctgaatcc tgcaacatag agacaaatat tcatcaggat cgattggtcg 3060
aagaagagga gtaggctgaa actccagccg aacgaggaag gaccatatga tgcaaggata 3120
tataaagatt cacacatcat actaatttct tgtgaagtgt gacatataca gttacgaatt 3180
tagagatgta aacttcgtgg cggactatcc agctggtgaa gaaacatggt gaccttggca 3240
aggctctcct ttgtttagtg caagcaacta atggagttta gactactctg ctttgctctg 3300
ctctctgaaa gcagctcagg ttgcaggtcc tctgaagcag ctgcgttttt ctttttcttt 3360

-continued

```
tttcgcgggt gtctttcatt cgttctctgg aaaactatgt ttatttctga tagatcaatc   3420

aatagtatac tggaacacta aatactgtta gaacaaaccc aatcaaaatg tactaat      3477


<210> SEQ ID NO 4
<211> LENGTH: 408
<212> TYPE: PRT
<213> ORGANISM: Aegilops tauschii

<400> SEQUENCE: 4

Met Ala Gly Val Leu Asp Ala Leu Ala Ser Tyr Val Thr Asn Met Leu
1               5                   10                  15

Thr Glu Met Ala Lys Glu Glu Val Ala Met Leu Ile Gly Val Ser Asp
            20                  25                  30

Gly Ile Lys Asp Leu Ser Ile Lys Leu Gly Asp Leu Lys Asn Phe Leu
        35                  40                  45

Ala Asp Ala Asp Arg Arg Asn Ile Thr Asp Asp Ser Val Arg Gly Trp
    50                  55                  60

Val Gly Glu Leu Lys Arg Ala Met Tyr Leu Ala Thr Asp Ile Val Asp
65                  70                  75                  80

Leu Cys Gln Leu Lys Ala Met Glu Gln Gly Gln Thr Lys Asp Arg Ala
                85                  90                  95

Cys Arg Cys Leu Asn Pro Leu Leu Phe Cys Met Arg Asn Pro Leu His
            100                 105                 110

Ala His Asp Ile Gly Thr Arg Ile Lys Leu Leu Asn Gln Asn Leu Asp
        115                 120                 125

Asp Ile Cys Lys Arg Gly Ser Ser Phe Asn Phe Ile Lys Leu Glu Ala
    130                 135                 140

Tyr Gln Asp Gln Lys Thr Thr Arg Ser Pro Ala Thr Asp Arg Lys Thr
145                 150                 155                 160

Asn Ser Leu Ile Glu Arg Ser Gly Val Val Gly Glu Lys Ile Glu Glu
                165                 170                 175

Asp Thr Arg Ala Leu Val Glu Val Leu Thr Arg Glu Ala Val Gly Asp
            180                 185                 190

Lys Ser Gly Arg Leu Ile Val Val Ala Ile Val Gly Ile Gly Gly Ile
        195                 200                 205

Gly Lys Thr Thr Leu Gly Lys Lys Val Phe Asn Asp Glu Ala Ile Glu
    210                 215                 220

Gly Lys Phe Thr Lys Lys Ile Trp Leu Ser Ile Thr Gln Asp Phe Thr
225                 230                 235                 240

Asp Val Glu Leu Leu Ser Thr Thr Ile Thr Ala Ile Gly Ala Asp Leu
                245                 250                 255

Pro Gly Gly Gly Gly Ala Pro Asp Lys Ala Leu Leu Val Asp Ala Leu
            260                 265                 270

Lys Asn Ala Ile Lys Asp Lys Lys Phe Phe Leu Val Leu Asp Asp Leu
        275                 280                 285

Trp Asp Val Asp Ala Trp Asn Lys His Leu Met Thr Pro Phe Ser Tyr
    290                 295                 300

Gly Gly Pro Gly Ser Arg Val Leu Ile Thr Thr Arg His Asp Thr Val
305                 310                 315                 320

Ala Arg Ser Met Lys Ala Phe His Pro Tyr His His Val Asp Lys Leu
                325                 330                 335

Ala Pro Gln Asp Ala Trp Ser Leu Leu Lys Lys Gln Val Val Thr Gly
            340                 345                 350

Glu Glu Asn Glu Pro Glu Val Asp Met Leu Glu Asp Ile Gly Leu Gln
```

-continued

```
        355                 360                 365

Ile Ile Ala Lys Cys Asp Gly Leu Pro Leu Ala Val Lys Val Met Gly
    370                 375                 380

Gly Leu Leu Cys Lys Lys Glu Lys Thr Arg Arg Asp Trp Gln Asp Val
385                 390                 395                 400

Leu Asn Asp Asp Met Cys Leu Tyr
                405


<210> SEQ ID NO 5
<211> LENGTH: 2853
<212> TYPE: DNA
<213> ORGANISM: Aegilops tauschii

<400> SEQUENCE: 5

gcagctccac ctaccgcagc tggccggtcg tcggtccttg catcgcatcc aaggcgacgc     60

cggctccacc actgccgcca ccactgattg gtaccttaag ctcccgtgaa gctacaaggg    120

aggaggcccc ctcgcctccc atccattgtt cctcaacagc ttgggtgccg agctccccca    180

ccaccacact agacgcgctg ggattcattg gatccgctcc agcgagcgag ccggattcag    240

ttcaccgaga ttatattcac ccttcccgtc tgccaactga ttacctccct tttcccattc    300

taccctgggt gaccactctg ctcactctca ctctttcttt ctcctctacg ccggccgtgc    360

acagcgcgac gccgacgacc gcatcccccc gacgttgccg cagccgccat acaagtagaa    420

ggaccgagat ggcaacctct cccagctttg tgctacaccg caagtactag gagcattgct    480

gaatgccgga tatagatccc cagatctagg ccaagggtct cgctttctgc tcactgttac    540

ttctatcatc tctccaatcg atccaagttc cagctcaagc cactggaccc tgcaactact    600

tgcgagacag cacgggatat ctatctctgc aacaagatcc gtctctcatc tctctagtcg    660

attcaagtac tagttcaagc gtgagcaaac cctgcaacca atggcggggg ttctggatgc    720

tttggcatcc tacgtgacca acatgctcac cgagatggct aaagaggagg tggccatgct    780

aatcggcgtg tctgacggga tcaaagacct aagcatcaag cttggggacc tcaagaattt    840

ccttgctgat gctgatagga ggaacattac cgatgatagt gtgcgggggt gggtgggcga    900

actgaagcgt gccatgtact tggccactga catcgtcgac ctatgtcagc tcaaggccat    960

ggagcaaggt caaacaaagg acagggcgtg ccggtgcctt aaccctctgc tcttttgcat   1020

gcggaatccc ctccacgccc acgacatcgg cacccgcatc aagctgctca accaaaattt   1080

ggatgatatt tgcaagaggg gcagcagttt caatttcatc aagctagaag cctaccaaga   1140

ccaaaagacc actcggtctc ccgccactga ccggaaaaca aattcactga ttgagcggtc   1200

cggtgtggtt ggagagaaga tcgaggagga cacgagggca cttgtggagg tgcttacaag   1260

ggaggcggta ggtgacaaga gtggtcgcct cattgtggtc gccattgttg gtatcggagg   1320

gattggtaag actaccctcg gcaagaaggt cttcaatgat gaggccatcg aaggcaagtt   1380

tactaagaag atatggctta gcatcacaca agatttcacc gatgttgagt tgttaagtac   1440

gaccatcact gccattgggg cagatcttcc tggagggggt ggggctccag acaaggccct   1500

acttgtcgat gctctcaaga acgccatcaa ggacaagaag ttctttcttg tactagatga   1560

cctgtgggat gtcgatgcat ggaacaaaca tctaatgact ccctttagct atggtggccc   1620

cggtagtaga gtcctcatca ccaccagaca tgacactgta gcccgaagca tgaaagcctt   1680

tcatccctac catcatgttg acaaattagc tccacaagat gcttggtcgt tgctcaagaa   1740

gcaggtagtc acaggagagg aaaatgaacc agaagttgat atgctagaag atattgggct   1800
```

-continued

```
gcagattata gcaaaatgtg atggcttacc acttgctgta aaagttatgg gtggactcct   1860

atgcaagaag gagaaaacac gacgtgattg gcaagacgtc ttgaatgatg atatgtggtc   1920

agtatctcaa atgtcaaagg aactaaatta tgccatatat cttagctatg aggatttgtc   1980

cccttactta aaacagtgct tcttgcactt ctccctcaaa ccaaaaaaga cagtgataac   2040

tgatactgaa atggtgtcca tgtgggttgg tgaaggattg gttgaaggag acacatatac   2100

tcgtagtttg gaagaaggga ataagtacta taaggagcta atagtaagga accttataga   2160

ggatcgattg gtggaagaag aggactagac cgaaactcct acggaacgag tttaggcgaa   2220

aggaccatat gatgcaagga tatacggata cctggaaagc atcagccata atgccatata   2280

cacttaacct gcagagattc ggacaccaca ctaatttctt gcgaagtgtg acatatacac   2340

ttactaattt tgagatgtaa acttcttggc gtactatcta gctggtgaag aaacatggtg   2400

accttggcaa ggctgtcctt tgtgcagtgc aagcaactaa tggagtttat gctactctgc   2460

tctgctctgc tctgttctct gaaagcagct caggaattcc gaatcagagt gatgtatact   2520

gggaccaaac aaatgttggt gagatcctgg tccacgaaga tcacgatgat gacctgctga   2580

ctggatgttc tagctatctt tagtttcttc aattagtgaa atcaaattag atcctggcta   2640

atatggtcaa atccgtggca cgtgggtcca cgaagaacac gtgggtctag ctatctgttg   2700

tttcttcaat cagtgcagtc aaattaagtt caggttttcc ccgcaaaaaa aaaaatttaa   2760

gttcaggttt gttctggggc tcaggacata tgttgtggat ggaagcaact gtatcaggac   2820

atattggatc aggacatgaa actgtaattg cag                                2853
```

<210> SEQ ID NO 6
<211> LENGTH: 495
<212> TYPE: PRT
<213> ORGANISM: Aegilops tauschii

<400> SEQUENCE: 6

```
Met Ala Gly Val Leu Asp Ala Leu Ala Ser Tyr Val Thr Asn Met Leu
1               5                   10                  15

Thr Glu Met Ala Lys Glu Glu Val Ala Met Leu Ile Gly Val Ser Asp
            20                  25                  30

Gly Ile Lys Asp Leu Ser Ile Lys Leu Gly Asp Leu Lys Asn Phe Leu
        35                  40                  45

Ala Asp Ala Asp Arg Arg Asn Ile Thr Asp Asp Ser Val Arg Gly Trp
    50                  55                  60

Val Gly Glu Leu Lys Arg Ala Met Tyr Leu Ala Thr Asp Ile Val Asp
65                  70                  75                  80

Leu Cys Gln Leu Lys Ala Met Glu Gln Gly Gln Thr Lys Asp Arg Ala
                85                  90                  95

Cys Arg Cys Leu Asn Pro Leu Leu Phe Cys Met Arg Asn Pro Leu His
            100                 105                 110

Ala His Asp Ile Gly Thr Arg Ile Lys Leu Leu Asn Gln Asn Leu Asp
        115                 120                 125

Asp Ile Cys Lys Arg Gly Ser Ser Phe Asn Phe Ile Lys Leu Glu Ala
    130                 135                 140

Tyr Gln Asp Gln Lys Thr Thr Arg Ser Pro Ala Thr Asp Arg Lys Thr
145                 150                 155                 160

Asn Ser Leu Ile Glu Arg Ser Gly Val Val Gly Glu Lys Ile Glu Glu
                165                 170                 175

Asp Thr Arg Ala Leu Val Glu Val Leu Thr Arg Glu Ala Val Gly Asp
            180                 185                 190
```

-continued

```
Lys Ser Gly Arg Leu Ile Val Val Ala Ile Val Gly Ile Gly Gly Ile
        195                 200                 205

Gly Lys Thr Thr Leu Gly Lys Lys Val Phe Asn Asp Glu Ala Ile Glu
    210                 215                 220

Gly Lys Phe Thr Lys Lys Ile Trp Leu Ser Ile Thr Gln Asp Phe Thr
225                 230                 235                 240

Asp Val Glu Leu Leu Ser Thr Thr Ile Thr Ala Ile Gly Ala Asp Leu
                245                 250                 255

Pro Gly Gly Gly Gly Ala Pro Asp Lys Ala Leu Leu Val Asp Ala Leu
            260                 265                 270

Lys Asn Ala Ile Lys Asp Lys Lys Phe Phe Leu Val Leu Asp Asp Leu
        275                 280                 285

Trp Asp Val Asp Ala Trp Asn Lys His Leu Met Thr Pro Phe Ser Tyr
    290                 295                 300

Gly Gly Pro Gly Ser Arg Val Leu Ile Thr Thr Arg His Asp Thr Val
305                 310                 315                 320

Ala Arg Ser Met Lys Ala Phe His Pro Tyr His His Val Asp Lys Leu
                325                 330                 335

Ala Pro Gln Asp Ala Trp Ser Leu Leu Lys Lys Gln Val Val Thr Gly
            340                 345                 350

Glu Glu Asn Glu Pro Glu Val Asp Met Leu Glu Asp Ile Gly Leu Gln
        355                 360                 365

Ile Ile Ala Lys Cys Asp Gly Leu Pro Leu Ala Val Lys Val Met Gly
    370                 375                 380

Gly Leu Leu Cys Lys Lys Glu Lys Thr Arg Arg Asp Trp Gln Asp Val
385                 390                 395                 400

Leu Asn Asp Asp Met Trp Ser Val Ser Gln Met Ser Lys Glu Leu Asn
                405                 410                 415

Tyr Ala Ile Tyr Leu Ser Tyr Glu Asp Leu Ser Pro Tyr Leu Lys Gln
            420                 425                 430

Cys Phe Leu His Phe Ser Leu Lys Pro Lys Lys Thr Val Ile Thr Asp
        435                 440                 445

Thr Glu Met Val Ser Met Trp Val Gly Glu Gly Leu Val Glu Gly Asp
    450                 455                 460

Thr Tyr Thr Arg Ser Leu Glu Glu Gly Asn Lys Tyr Tyr Lys Glu Leu
465                 470                 475                 480

Ile Val Arg Asn Leu Ile Glu Asp Arg Leu Val Glu Glu Glu Asp
                485                 490                 495
```

<210> SEQ ID NO 7
<211> LENGTH: 2609
<212> TYPE: DNA
<213> ORGANISM: Aegilops tauschii

<400> SEQUENCE: 7

```
gcagctccac ctaccgcagc tggccggtcg tcggtccttg catcgcatcc aaggcgacgc     60

cggctccacc actgccgcca ccactgattg gtaccttaag ctcccgtgaa gctacaaggg    120

aggaggcccc ctcgcctccc atccattgtt cctcaacagc ttgggtgccg agctccccca    180

ccaccacact agacgcgctg ggattcattg gatccgctcc agcgagcgag ccggattcag    240

ttcaccgaga ttatattcac ccttcccgtc tgccaactga ttacctccct tttcccattc    300

taccctgggt gaccactctg ctcactctca ctctttcttt ctcctctacg ccggccgtgc    360

acagcgcgac gccgacgacc gcatcccccc gacgttgccg cagccgccat acaagtagaa    420
```

-continued ggaccgagat ggcaacctct cccagctttg tgctacaccg caagtactag gagcattgct 480
gaatgccgga tatagatccc cagatctagg ccaagggtct cgctttctgc tcactgttac 540
ttctatcatc tctccaatcg atccaagttc cagctcaagc cactggaccc tgcaactact 600
tgcgagacag cacgggatat ctatctctgc aacaagatcc gtctctcatc tctctagtcg 660
attcaagtac tagttcaagc gtgagcaaac cctgcaacca atggcggggg ttctggatgc 720
tttggcatcc tacgtgacca acatgctcac cgagatggct aaagaggagg tggccatgct 780
aatcggcgtg tctgacggga tcaaagacct aagcatcaag cttggggacc tcaagaattt 840
ccttgctgat gctgatagga ggaacattac cgatgatagt gtgcgggggt gggtgggcga 900
actgaagcgt gccatgtact tggccactga catcgtcgac ctatgtcagc tcaaggccat 960
ggagcaaggt caaacaaagg acagggcgtg ccggtgcctt aaccctctgc tcttttgcat 1020
gcggaatccc ctccacgccc acgacatcgg cacccgcatc aagctgctca accaaaattt 1080
ggatgatatt tgcaagaggg gcagcagttt caatttcatc aagctagaag cctaccaaga 1140
ccaaaagacc actcggtctc ccgccactga ccggaaaaca aattcactga ttgagcggtc 1200
cggtgtggtt ggagagaaga tcgaggagga cacgagggca cttgtggagg tgcttacaag 1260
ggaggcggta ggtgacaaga gtggtcgcct cattgtggtc gccattgttg gtatcggagg 1320
gattggtaag actaccctcg gcaagaaggt cttcaatgat gaggccatcg aaggcaagtt 1380
tactaagaag atatggctta gcatcacaca agatttcacc gatgttgagt tgttaagtac 1440
gaccatcact gccattgggg cagatcttcc tggagggggt ggggctccag acaaggccct 1500
acttgtcgat gctctcaaga acgccatcaa ggacaagaag ttctttcttg tactagatga 1560
cctgtgggat gtcgatgcat ggaacaaaca tctaatgact ccctttagct atggtggccc 1620
cggtagtaga gtcctcatca ccaccagaca tgacactgta gcccgaagca tgaaagcctt 1680
tcatccctac catcatgttg acaaattagc tccacaagat gcttggtcgt tgctcaagaa 1740
gcaggtagtc acaggagagg aaaatgaacc agaagttgat atgctagaag atattgggct 1800
gcagattata gcaaaatgtg atggcttacc acttgctgta aaagttatgg gtggactcct 1860
atgcaagaag gagaaaacac gacgtgattg gcaagacgtc ttgaatgatg atatgtggat 1920
cgattggtgg aagaagagga ctagaccgaa actcctacgg aacgagttta ggcgaaagga 1980
ccatatgatg caaggatata cggatacctg gaaagcatca gccataatgc catatacact 2040
taacctgcag agattcggac accacactaa tttcttgcga agtgtgacat atacacttac 2100
taattttgag atgtaaactt cttggcgtac tatctagctg gtgaagaaac atggtgacct 2160
tggcaaggct gtcctttgtg cagtgcaagc aactaatgga gtttatgcta ctctgctctg 2220
ctctgctctg ttctctgaaa gcagctcagg aattccgaat cagagtgatg tatactggga 2280
ccaaacaaat gttggtgaga tcctggtcca cgaagatcac gatgatgacc tgctgactgg 2340
atgttctagc tatctttagt ttcttcaatt agtgaaatca aattagatcc tggctaatat 2400
ggtcaaatcc gtggcacgtg ggtccacgaa gaacacgtgg gtctagctat ctgttgtttc 2460
ttcaatcagt gcagtcaaat taagttcagg ttttccccgc aaaaaaaaaa atttaagttc 2520
aggtttgttc tggggctcag gacatatgtt gtggatggaa gcaactgtat caggacatat 2580
tggatcagga catgaaactg taattgcag 2609

<210> SEQ ID NO 8
<211> LENGTH: 471
<212> TYPE: PRT

<213> ORGANISM: Aegilops tauschii

<400> SEQUENCE: 8

Met Ala Gly Val Leu Asp Ala Leu Ala Ser Tyr Val Thr Asn Met Leu
1 5 10 15

Thr Glu Met Ala Lys Glu Glu Val Ala Met Leu Ile Gly Val Ser Asp
20 25 30

Gly Ile Lys Asp Leu Ser Ile Lys Leu Gly Asp Leu Lys Asn Phe Leu
35 40 45

Ala Asp Ala Asp Arg Arg Asn Ile Thr Asp Asp Ser Val Arg Gly Trp
50 55 60

Val Gly Glu Leu Lys Arg Ala Met Tyr Leu Ala Thr Asp Ile Val Asp
65 70 75 80

Leu Cys Gln Leu Lys Ala Met Glu Gln Gly Gln Thr Lys Asp Arg Ala
85 90 95

Cys Arg Cys Leu Asn Pro Leu Leu Phe Cys Met Arg Asn Pro Leu His
100 105 110

Ala His Asp Ile Gly Thr Arg Ile Lys Leu Leu Asn Gln Asn Leu Asp
115 120 125

Asp Ile Cys Lys Arg Gly Ser Ser Phe Asn Phe Ile Lys Leu Glu Ala
130 135 140

Tyr Gln Asp Gln Lys Thr Thr Arg Ser Pro Ala Thr Asp Arg Lys Thr
145 150 155 160

Asn Ser Leu Ile Glu Arg Ser Gly Val Val Gly Glu Lys Ile Glu Glu
165 170 175

Asp Thr Arg Ala Leu Val Glu Val Leu Thr Arg Glu Ala Val Gly Asp
180 185 190

Lys Ser Gly Arg Leu Ile Val Val Ala Ile Val Gly Ile Gly Gly Ile
195 200 205

Gly Lys Thr Thr Leu Gly Lys Lys Val Phe Asn Asp Glu Ala Ile Glu
210 215 220

Gly Lys Phe Thr Lys Lys Ile Trp Leu Ser Ile Thr Gln Asp Phe Thr
225 230 235 240

Asp Val Glu Leu Leu Ser Thr Thr Ile Thr Ala Ile Gly Ala Asp Leu
245 250 255

Pro Gly Gly Gly Gly Ala Pro Asp Lys Ala Leu Leu Val Asp Ala Leu
260 265 270

Lys Asn Ala Ile Lys Asp Lys Lys Phe Phe Leu Val Leu Asp Asp Leu
275 280 285

Trp Asp Val Asp Ala Trp Asn Lys His Leu Met Thr Pro Phe Ser Tyr
290 295 300

Gly Gly Pro Gly Ser Arg Val Leu Ile Thr Thr Arg His Asp Thr Val
305 310 315 320

Ala Arg Ser Met Lys Ala Phe His Pro Tyr His His Val Asp Lys Leu
325 330 335

Ala Pro Gln Asp Ala Trp Ser Leu Leu Lys Lys Gln Val Val Thr Gly
340 345 350

Glu Glu Asn Glu Pro Glu Val Asp Met Leu Glu Asp Ile Gly Leu Gln
355 360 365

Ile Ile Ala Lys Cys Asp Gly Leu Pro Leu Ala Val Lys Val Met Gly
370 375 380

Gly Leu Leu Cys Lys Lys Glu Lys Thr Arg Arg Asp Trp Gln Asp Val
385 390 395 400

-continued

```
Leu Asn Asp Asp Met Trp Ile Asp Trp Trp Lys Lys Arg Thr Arg Pro
                405                 410                 415

Lys Leu Leu Arg Asn Glu Phe Arg Arg Lys Asp His Met Met Gln Gly
            420                 425                 430

Tyr Thr Asp Thr Trp Lys Ala Ser Ala Ile Met Pro Tyr Thr Leu Asn
        435                 440                 445

Leu Gln Arg Phe Gly His His Thr Asn Phe Leu Arg Ser Val Thr Tyr
    450                 455                 460

Thr Leu Thr Asn Phe Glu Met
465                 470
```

<210> SEQ ID NO 9
<211> LENGTH: 8844
<212> TYPE: DNA
<213> ORGANISM: Aegilops tauschii

<400> SEQUENCE: 9

```
tgatcatctt cacacggaag aaccaagatc gttaacttgg aaagataagt taaggatcac     60
aaccgaaaca tgcaaagctc ttgcatacct tcactctgct gtttcagtcc ctgtaataca    120
tagagatatc aagccttcca acatacttct tgatgatgcc ttgacagcaa aagtgtcaga    180
ctttggagct tcaaggtaca ttgccatgaa tcaaacagga acaacaactg cagtgcaagg    240
aactataggt tacttggatc ctacatatta ttatagcaga cgcctcacag aaagtagcga    300
tgtttatagc tttggagttc ttcttattga attgcttact aggaggaagc catctttgta    360
tagatccaat gaaggcgttg ggcttgtcat ggagttcgtt gcactacttg cagaaggcaa    420
tctatccgaa atactagacc caccagttgt agaagaggga ggtagcaaag tcgaagacgt    480
agctaatcta gctgtgtcgt gcgtgaaact gagagcagag gagcgaccaa ctatgaggca    540
agtggagatg gcgctggaag ctctccaagc acgcaaggag catgtcatgg gtgatttgat    600
agaagaaaca aacgggaaga aacatgcagc accaaattgt ccatcgacta gcaaacgacc    660
aaagggaagt ggagcaagca gatgctatag ccaagaagaa gaggtggtgt tatccgcaac    720
attccctcga tagttttgct tgcccggaag tgatttttag tgatgttgta ttctttctac    780
tatttggaat gagcgtgtgc tattgtatga atatatgagt tacacataac tctagtgtat    840
tatttaaaat aaatttgaat gcacccaact ctgttgtgct aattttgcat gttgtcgcgc    900
aatcagcatt tggtcttgat gatcgacagt tcatcactag tggaaaaagt gttagtcaca    960
atttttgttg gtggcgcacc gactcctaac aacggtagta ctattttttc caaataatgg   1020
tggcgtcgga caatttggta cgacattgat ttgagcatac cgctggcata gaatttttct   1080
cgtaccacat aggcattttc tgagtttttt tccgtgtgct ttcgttttct atagcgtggc   1140
ccattaggca tacgacagcg gtatccatta ggcccacgcg agcaaaataa aactacccta   1200
tccagtaaag atcagtgtag gtccgattca ctaacctatc attttcgcct cttcttcatc   1260
ccccttctcg accgccccgc caccgccact gcccgatgac gccgctcttc gccgccggaa   1320
ctgcgcggcc gccgccaact ccggcaaggt gctacactgt gtcatgtttg gtcgataggt   1380
gctacgcacg acaaatcctt tgcgtctgga tggacgagcg caggacgata gcgtcgtcgg   1440
gcgtcgtggt ggcatcgacg gaccggtaag gatgatgcgg atctatctcc tgaagatggg   1500
tcagcggtcc gatgatgatg gcggcttcta aaacgtgtgc atgtgttgta cgcattttgt   1560
ctgctgcgcc ggtgttagtt ctgatacatt atgtggatgg atcggcgacg acactggttt   1620
tagatatggg agtgagagcc ctccacatta tcgagttttt tagatgtgag tagtggtttc   1680
```

-continued gggtggcttg atgtatattc ctgttcgacc tttgttgaat aataaataaa gatgaccgta 1740
tgcatcgatt gatgcagagg ccggtgtttt aacctccttt ttgaaaggaa aagtactatg 1800
ttagtagagt gcttagctga ttaaggatga aaactgcaat agctccttac tttccctggt 1860
aaaactacaa atatcacaaa tgcaaaccca cccatcccgg tagcctcgtc aaattaaaat 1920
aaaaaaaaat ataagaaaag gaaaatgcga ccggcggcta gcagctccac ctaccgcagc 1980
tggccggtcg tcggtccttg catcgcatcc aaggcgacgc cggctccacc actgccgcca 2040
ccactgattg gtaccttaag ctcccgtgaa gctacaaggg aggaggcccc ctcgcctccc 2100
atccattgtt cctcaacagc ttgggtgccg agctccccca ccaccacact agacgcgctg 2160
ggattcattg gatccgctcc agcgagcgag ccggattcag ttcaccgaga ttatattcac 2220
ccttcccgtc tgccaactga ttacctccct tttcccattc taccctgggt gaccactctg 2280
ctcactctca ctctttcttt ctcctctacg ccggccgtgc acagcgcgac gccgacgacc 2340
gcatcccccc gacgttgccg cagccgccat acaagtagaa ggtgaggacc cccttcctct 2400
cctcttcgtc ctagccagcg gatcctcaga tctgagctga gtggggccgc agcaagctca 2460
gactaaattg tttcttacaa atctttgaga tgatttccgt accacgtata gaactcctaa 2520
tttctcagca gaagaaatca ccgggttctg ggtttgcgca caaagctttg attttgtttt 2580
gtgctgtgct gtgaaaattg agctcagatc ttcttttagt agcctgtgat ttgtgcagtc 2640
caatttgctg tgcggtacca actaagctca catcttttta gtagaaagta cctagtagtt 2700
tttagagctt tgctttgcaa gtagtacact agtactacaa attaagctca cacattatat 2760
tattacagag gctctgtttt gttcagtact acaaagctta gattttgatt tctgtactac 2820
gaatttagct cagatctttt ttctgaacag caagctttta atttctgcaa ataggaccga 2880
gatggcaacc tctcccagct ttgtgctaca ccgcaagtac taggagcatt gctgaatgcc 2940
ggatatagat ccccagatct aggccaaggg tctcgctttc tgctcactgt tacttctatc 3000
atctctccaa tcgatccaag gtaattcatc gattgcagca gcaccaccct ctatttagtg 3060
tgcactttct tttgtgtgca atccatgctt ttcctttaca acgaattgtt ggtagtctct 3120
gctgagtgaa tctacatgac catccttctt ttccattttt tttgcatgtc actattgatg 3180
tgtgaaaggt agtaataaag aggactcatt ttgtgtgcat cctttgtttt cagttccagc 3240
tcaagccact ggaccctgca actacttgcg agacagcacg ggatatctat ctctgcaaca 3300
agatccgtct ctcatctctc tagtcgattc aaggtacata gctgaatcca gctacacaac 3360
acttactcta gttatttttc tttttgaaa gagctgatcg tgtgtctttc catttcaatt 3420
gttggtgttt gttcaaggta atactatatc ggttttattt cgagccgaat ttctgtgcac 3480
tgtctttgca agccacattt tcctttggat ttgttactag cctctagtga gtgaatctga 3540
ttatccttcc tgttagcatg ggattgttga tgtgaaaaag cgaggtagta atacaaagga 3600
ctaattttta tttccatgct tcttttcagt actagttcaa gcgtgagcaa accctgcaac 3660
caatggcggg ggttctggat gctttggcat cctacgtgac caacatgctc accgagatgg 3720
ctaaagagga ggtggccatg ctaatcggcg tgtctgacgg gatcaaagac ctaagcatca 3780
agcttgggga cctcaagaat ttccttgctg atgctgatag gaggaacatt accgatgata 3840
gtgtgcgggg gtgggtgggc gaactgaagc gtgccatgta cttggccact gacatcgtcg 3900
acctatgtca gctcaaggcc atggagcaag gtcaaacaaa ggacagggcg tgccggtgcc 3960
ttaaccctct gctcttttgc atgcggaatc ccctccacgc ccacgacatc ggcacccgca 4020
tcaagctgct caaccaaaat ttggatgata tttgcaagag gggcagcagt ttcaatttca 4080

-continued

```
tcaagctaga agcctaccaa gaccaaaaga ccactcggtc tcccgccact gaccggaaaa   4140
caaattcact gattgagcgg tccggtgtgg ttggagagaa gatcgaggag gacacgaggg   4200
cacttgtgga ggtgcttaca agggaggcgg taggtgacaa gagtggtcgc ctcattgtgg   4260
tcgccattgt tggtatcgga gggattggta agactaccct cggcaagaag gtcttcaatg   4320
atgaggccat cgaaggcaag tttactaaga agatatggct tagcatcaca caagatttca   4380
ccgatgttga gttgttaagt acgaccatca ctgccattgg ggcagatctt cctggagggg   4440
gtggggctcc agacaaggcc ctacttgtcg atgctctcaa gaacgccatc aaggacaaga   4500
agttctttct tgtactagat gacctgtggg atgtcgatgc atggaacaaa catctaatga   4560
ctccctttag ctatggtggc cccggtagta gagtcctcat caccaccaga catgacactg   4620
tagcccgaag catgaaagcc tttcatccct accatcatgt tgacaaatta gctccacaag   4680
atgcttggtc gttgctcaag aagcaggtcg gtacttccca aaactcaata taatacacgt   4740
cgtttgggac tacactgtta agttaatttg atctacactt gcataagtct accaatctga   4800
aatttatata tttataatgc ttccttgact taaatttcac cgtaacacga gttcatcaag   4860
tttgtatatg aaattaggaa gatattaaac aatattttca tttgtatgca tgatgtacgg   4920
cttctcaatt tgtggattat tccggactta agtttagcaa ttatcaggga ttgcatccag   4980
cttctcaatt agtttctact tgcaggtagt cacaggagag gaaaatgaac cagaagttga   5040
tatgctagaa gatattgggc tgcagattat agcaaaatgt gatggcttac cacttgctgt   5100
aaaagttatg ggtggactcc tatgcaagaa ggagaaaaca cgacgtgatt ggcaagacgt   5160
cttgaatgat gatatgtggt cagtatctca aatgtcaaag gaactaaatt atgccatata   5220
tcttagctat gaggatttgt ccccttactt aaaacagtgc ttcttgcact tctccctcaa   5280
accaaaaaag acagtgataa ctgatactga aatggtgtcc atgtgggttg gtgaaggatt   5340
ggttgaagga gacacatata ctcgtagttt ggaagaaggg aataagtact ataaggagct   5400
aatagtaagg aaccttatag aggtagatac aaagtaccct agtcaactta tttgcaacat   5460
gcatgatgtt attcgctcat ttgctcaatt tgtggctagg gatgaaacac tagtaggtca   5520
caatggagat actatcaaaa caaatcttag atcaccgaat tatcttagat tatccataga   5580
aacgaaagga gtgggatccg atgaatttga gtggagatat ttaagagagc aaaaaattgct   5640
taggtctcta atattaactg gaaacctcaa aagtcagcct ggggattcgt tgactatctt   5700
cccaagtcta cgtcttttgc atatagaatc agcaaatatt gctgcactag ttgaatctat   5760
gtaccaactc aagcatttga gatatttggc attaaagagg actgatatgt gtagactacc   5820
agagaacatc catgagatga aattcctaca gcatattagc cttgaaggtt gtgaaagttt   5880
catgaaactt cctgatagta ttatcaagct gcaagggttg agatatcttg atatgggtga   5940
cacacgtgta agtagtattc ctaggggttt ccgagctctt acaaatttga cttcactatt   6000
tgggtttcca gcctatattg atggtgactg gtgtagtctg gaagagttgg ggtctctttc   6060
ccagctcaat gaactttcac tacagagcct agaaaatgta tctagtgcct tgttggctga   6120
aaaggcaagg gtaaatgcaa agaaacaact taccgtactt gctttaaaat gtggtggtag   6180
agtgggacat gggttggtcc aaggagaggt ctctgagtct aaggaggagg agcaaataat   6240
tgaggcggtg tttgatgtgc tctgtcctca gccttgcata gaacacatca gaatagaaag   6300
atattttggt cgtcggctcc caggatggat ggcgtccaca gctatggtgc ccctcgagag   6360
cttgaagatt ctatgcctcg aacacctgcc ctgctgcacc caactcccag atggcttgtg   6420
```

-continued

```
caggctcccg tatttggagt ggataaaagt gatgaatgct ccagtaatca agtgtattgg   6480
tcctgaattc gttcaacagt acaatcagct gcaccgtcct tcatctcagt tggctgctac   6540
gtttcccaaa ctccagatgt tggaatttca cggaatggag gaatgggagg agtgggtttg   6600
ggagacggaa gtgaaagcta tgcccttatt ggaggaactt cgtatcactt cttgcagact   6660
gagccgtatg cctccaggac ttatgtctca tgcaatggct ttgaagaagc taacaatatg   6720
gagcgtccaa tgtctccact ctctagagaa ctttgtttct gtagttgaac tcgaattggg   6780
aaacatacct gaactggcca tgatctccaa tcttccaaaa ttacaaaaac ttacaatcga   6840
gtgctgccca aagctcgaga tgctgcagga gatggctgca ctccggagac tcgagctgac   6900
cattttcaac agcgaaaatc aacttccggt ctacctgcag actgtgaagc ctagtaattt   6960
gctgctgacc tgcaacctag cggtactcac ttccatggct gagggtgaat ctagctccga   7020
gtgggacaag ttcagtcata tcaaccacgt tgaggcttat gcagaggatg gagaagatga   7080
gaagaaatgg cacgtgttct acacatctga atcctgcaac atagagacaa atattcatca   7140
ggtaatactt tggtctctcc ctctttcaat ctagctaata ataatattct tccttattgt   7200
tgtctgttcc atgcatatct attttcatca gtatgatata ggatagctga atatatctcc   7260
cactgttttt gttttgcttg ccaggatcga ttggtcgaag aagaggagta ggctgaaact   7320
ccagccgaac gaggaaggac catatgatgc aaggatatat aagtatgtct gctgttacaa   7380
cttcaactag ttttgagatc gaatccatga agggatacgg ggaaaagcat cagccataat   7440
gccatataca cttacctgca gagattcaca catcatacta atttcttgtg aagtgtgaca   7500
tatacagtta cgaatttaga gatgtaaact tcgtggcgga ctatccagct ggtgaagaaa   7560
catggtgacc ttggcaaggc tctcctttgt ttagtgcaag caactaatgg agtttagact   7620
actctgcttt gctctgctct ctgaaagcag ctcaggttgc aggtcctctg aagcagctgc   7680
gtttttcttt ttcttttttc gcgggtgtct ttcattcgtt ctctggaaaa ctatgtttat   7740
ttctgataga tcaatcaata gtatactgga acactaaata ctgttagaac aaacccaatc   7800
aaaatgtact aatgctctgc acctgtgagc caatcaaacg gatgtatatc aaagagaggc   7860
atcatattat tgaggagcca tcggagattt tctgaatttg cccagcttga ggatggatct   7920
gggccgccgc cgccgccagc gttggggccg cagctctgta cgcgatttgg gattgaacga   7980
tgaggccatc gagaccaaat tagcttgcag ggaaggacct tttgcaaat tatgcgccta   8040
aatctgggcc atcattttcc tatccggtgg tccagatcca ctttttcgat ttttctacca   8100
taagcatgtt ttctgttgta gttgctcctc aacagttgta cgtattttga tggtagatgg   8160
atcatggatg gatgcataag gctggtcata gtgggaagta tcatatacta gtatcatgca   8220
tatgatacta gtgtataaac tacatccata gtgcatagta tcatagatta gtatcatagg   8280
tggtctcatt tattgccatg catgacacat agtagcatta cattaattat gttacggtat   8340
ctacctatgt tactataact atctctctct tctttaattg cctgccacat aagcatgttt   8400
gcgattccca agtgcatgat actacttatg ttacttccac tatgaccagc ctaatgcatc   8460
ttcacaatca tttggcatca ctggccgccg gccaccgttt ttactccatt attttttgtt   8520
cagtgggtag taaggaacca gtaacaatta ataactggtt aatagatgca tggatctgat   8580
aaataagcca actatttagc aactttaggt gctaacttat taaataaggt gtgcttagca   8640
ataacaggtt aagcacctat acattgagga gttgagttgc taagatattt aatgcactta   8700
acatctcatt taagcacctt tgcatttgaa gaggtcaaag tgacagctag cttactcagc   8760
ttaagataat ttgagttccg gaaaaggttt tcgtcccgct ttatataatt caatcgaccg   8820
```

ttcacatgca ggactagctg taca 8844

<210> SEQ ID NO 10
<211> LENGTH: 39535
<212> TYPE: DNA
<213> ORGANISM: Aegilops tauschii

<400> SEQUENCE: 10
tgttttaaga tcaatgacct ttttaaattt cgcggccctt tttcaaagtc atgatttttt 60
ttcaaattca tgattttatt agaaaaatat aatgaacttt ttcatttttt cgaattaatt 120
tatcaaattc gagtattgtt tttcaaatcg atgaaatttt tataaacttg tgagcgaatc 180
catgattttt taattttaaa accgggaact ggtttttcag ttaacaaaat accagcagaa 240
gagaaaaccg agaaaatata gcgaggaaac gaaaactgat gatcacaagc ggtgaacagg 300
aagtggatgc cgaggtgctt gggctgcggc ccagtaaggc aggtgtgagc accaacttat 360
tttcctggca cataaggctc caaggaggaa aaaacttcat gattttgtag gaagtttgtg 420
aaaattggaa aaagttcaag aatatgaata aagtacgcgt aagggaaaaa gttcactgat 480
ttaaaaaacg aagttctcga atttgacgaa aatgttcgtg aaattgagaa aagttcatcg 540
attggggaaa aaggttaaca attttacaaa aaagaattac gaagtaaata ttttttttcat 600 aggaggcatc ccgactggat cggcccatta ttgcacaaga aaaaagggaa aattaaaata 660
tcaattttaa acacttgttt aaattatgat tttaaatact tcttgccttc aaacctggca 720
tggatgccta tcatgtgcat gcccacctac tggcaaaagt tgatatcatt tcataaatgt 780
ccaaaaaact agcatgttca atgtagggtg tcggagtagg tcagaatgct ccgtttgaga 840
gcacattgtt tggtttgcta atttgtttac attttcagga gttttctaag tcaaaaaggg 900
cgataaatgg ccgaatgggt tggaactagc atacattgtc gaaaatcgtt caaacatgac 960
attgatgcct accatgggca tgcttttcat gcatgtccaa aaatagaaca tgttcaacgg 1020
agggtgtccg agtaggcgag aagggtccat atgagagcaa gctttttcgg aatcgcccag 1080
taaccccatt tcccatgaga ttatatgaac aattaaaggc gccatgccaa gttgtttgag 1140
ttttggataa tatttgtatt ttctggagtt tttttgttga aaagttgctg ataaattgcc 1200
ggacgtgacg caacttgcat acggtgttgc aaagcgttca aacctggcat ggatgcctac 1260
cataggcatg ctcatctgct ggcaaaaggt aggatcatta aatttatgtc aaaaatagat 1320
catgttcaaa gtagggtgtc cgtgtaggct agaaaggtcc gtatgagaac atgttttttt 1380
ggcatcgtca aatatcccta aaaattttac atgagcatat atgacctatt taaaggcacc 1440
atgcaaagtt attttagttt ggacaattgt tgcactttct agaattttct tgatgaataa 1500
tgactgataa aacagctgga cgtgatgcaa cttgcatccg gtgttagaat atattcaaat 1560
caggcatgga tacctatcat gggcatgccc acatgctgga aaaagttaga gtcatttcat 1620
gtatgtctaa aaatatatca tgttcaacga agggtgtttg cgtaggccag aaggggtcgt 1680
atgagagcat attttttcgg cttcgtcata tgaccccaaa tttttcccat gctcttatat 1740
aaccaattca aggcaccatg ccaagttgtt tgagttttcg aaaaatcatg catttctgg 1800 agttttctcg gtgaaaaagt gatgataaat ggctggacgt gtcacaaggt tcaaacggtg 1860
tcagaaatcg ttgaaaccag gcatcgatgt ttcatatgtc cgcgccaggc tgctgtaaaa 1920
agttggggtt atttatccgt agtccaaaaa accaccagtt gagagaagtg tgcttactaa 1980
gccagacgag tgcatccgtg agcatggtgt ttgtattttc cgctaatata attaacacga 2040

-continued

```
aaaaaaatgt cctaactatt tctttaaatt tatctacaat tttagatgct tttgttattt   2100
gcaatttccg tcattgtcaa tgaacatgaa ctttaatttg tgcaaagtgc acacatttgc   2160
caaaattcga aaaaagaaaa aagaaaaaga aaacagaata taacgaagca aaacccggtt   2220
ttttaaaaga tggagaatgg ccaaaaattt cacaaaatta catttgccac ataagaagcc   2280
aaaaagaaag caagtgttca agttgtgttc aaaatgttag ttcctatgtt tgcacgctcc   2340
tcaaatatct ttaaaattgt tcaaaatgtt gttcaaaaaa atgttcttaa cattttgaac   2400
taacataacc atttaatttt tttgttttca tgctttaaaa aaatgttgtt cattgttttt   2460
aaatgttcat gtctttttta aatgaaaatt ttaatatgtg ttcaagttgt tcaaaacatt   2520
gttggatttt cagaatgttc gtgcgcctag ttcggaaccc ctcgtccgtg ggcctgctgc   2580
ctcgttatct tgcagcattc aactgacgtt ggtgctaatt tggcagatca tggacgtggc   2640
agctccttca atacattagt tagcaaaaca gccatttatc cctcatgatc atgtaaagtg   2700
gaacgccttt atccctaaaa aacaatcaaa gcagccactc ctagtcgatt attccccttt   2760
tagctgattt tgatccgttt ttgagggaga aaagggcggc gtgataggct tccctcccca   2820
ttcgattatt cccctcgacc aatctacaca tgcctagatt acgctgccct tccttagtcg   2880
ccctatgtac acctggacct actttttttt aaaatttaca cctgggcctt tttttaattt   2940
acacatggac ctactgggta catgtgtttt ggttgacggg ctcaataaac tcggacggaa   3000
ggagtggttc gtaaatttgc acgctcctca tttttcacaa acactagtca gagccactca   3060
ctctcacgtg cacagaggtc cgtggtttga ttcctagagg gtgcatgcat acttattttg   3120
tgaactttta ctccggcggg tgagtgatgt attttaataa aagaccatct taccctttttt   3180
aggggagacc atcttaccct ttagtatgaa ggggtatgaa gaaatctact tctttgaagt   3240
gattaggaag gttgtaccaa aggagaagtg acattaaaat aacgtaaaat gggcggggac   3300
aaacgagact atgagaatgc accaaaatga aaaaaacagg cttaccggtc ataattttgt   3360
cggcaggctg gtggacgtgt agcaggacga gcttgtcgcc accggtaagg aggtttcgag   3420
cggcccacat gaggtttgac ctgccgtcct cttcatcctt cccgacagcc acatacaagt   3480
tccttcctcc tccgccgcca ccatcctctt cgcccttcca taagggcaca tacatccttc   3540
ctccttcgcc atcatgctcc aagttggcgg tggtctcctc tttggcacaa gcaccgacac   3600
cggcaccgag gctagcgctt atgtcggact cggtggacga cctccgggta cgccacatct   3660
tggcccagta ggatcggttc ctcagcttac cctcacgagc agtgtagcta tacatcaagc   3720
cgccggaaga tgatgatgat ggtgatagtg atgatgatgc cggcttaggc ttaggcttac   3780
aaactcttga gaatctgctc cgccaagctc gtcaaacaga tcaaagagac tgagaaattt   3840
ctcccaagaa cccttgaccc gaagattcga accctcgacc aagctggcca aagagatcaa   3900
actctggtca aagagattcg aacacgcaat ttctcaagca tgtgttttct gttctcaagt   3960
gcaatttcaa gcttacagga cgcaactgac acacattgta tagtttttag gctgtcaaat   4020
gcattttttt ctgagcaaag gaagcttcac gaaggaacca gagttttctt tttggcaata   4080
aaacccccctc tatatttggt gcacgggtcg ccggttagcg accacgcgtg gaccccccccc   4140
ccccccccta cacacacacg ctggcctttc catgggctag tttttctttt tctttctttc   4200
gtgtttttct attcttttta ttattatttt ttcatttttc tagtttttttc agtttgcaaa   4260
actcttttaa atttatgaat attttggaaa tcatgcacat tttctgaaat gatgaatttt   4320
tttaaattga tgaacatatt ttcgaaaccg tggacctttt ttttacaaac ttgtgaagag   4380
tctcctaaat cccgaatgtt ttttgaaatc atgaacattt ataaaattcg tgaagaattt   4440
```

```
gtcaaaatca tgatcctgtt tttaaaaaat tcatgatcat tcatttttttg aaatgatgaa   4500
cgttgttcga ctcatgaata ttttgtaaat ttatgaacaa tttttcaaaa ttgtgaattg   4560
tttgaaaatt tgtgcagatt cttttgaatt cacgaacatt ttttaacacg gcactgccag   4620
ccacctgagc aagcccgaca gcatcgctcg gtggtggcaa ctggagagcg cacagggtga   4680
gggggccgag aaaagtgtat cggaacgctg cctgagtcgc ccgacaaaag gacgacgcgg   4740
gggcatttct gttttttttaa cacggcacat tcgaagtcac tcacatacac gagcatacaa   4800
tcaacctaca aatgtgtgca catacacacc ttacccctat gtgtgatatt caatatgttg   4860
cattatctag cacatatcat gttcttattt ctgaataata ggaccggcag cgtgcacatg   4920
tccacgtaca gttcagtagc ttcacttagt tagtctgtaa gtagattcag ttagttggtt   4980
agccagattt gctcaattga tcgcttctag ggatgctagg atcgttacgg tttatgcggg   5040
cagtgtagtt gctcgatttc agcttggcat cgtgggatgg cacgaccagt aggccggctt   5100
gaaacatggg cgtctcccgt gtaattcgtc agccgtttga gctggctaca aataacagaa   5160
aagcagagaa aaagctgcag ttcagtgagc agcacaaaaa cttctgtgag agtctctcct   5220
accacctctc gcaaagctcg gtcgttagtg ctaggcaaca acaatgataa cctccgagag   5280
actgagttga cacatgcttt tgagattgac aaagttgcca taaacgcctt cgtagtcgat   5340
cagatcgtct catccccact taacgcacat caccggaaca aggtatgtga gaaccaatgt   5400
catgtctagg acttgaaatc tggtgggttg agaataccac taccctcata accatcatac   5460
cgcagcttgg ttcgccgttt tttgtttgtt gatatatgtt cccccacggt cacaatgttt   5520
tggtacagga aaaaggtaag aatactcaat agtagaatgt tgtggagaag tggtggcaga   5580
ggggccgtac atttccttgt aacatgcctc tgccagtagt ccgtcctctc atcgaatcat   5640
catggttgaa catagcttac tattttcttg ataatcatta tcttcatgtt caactccaat   5700
tgttcctaca gaaaatatat tcagacttag cacacaaatg aactatgagt gaactactac   5760
tgaagaaaca aggctcacag tttaaggagt gacaacgtat ctgttcaaca ggcatgactt   5820
tgctatttgc cagtgtgttt tttatgagtg tgcgttagtg ttgcctgtgt gtaacccagc   5880
catgcagaaa ccgggtgcgt gctcattgcg tttgtatcat cttgatgctt cattttgagt   5940
gaataaaatc cacccattaa aaaaaataag cattgatgtt cctggcctag cgggagaaag   6000
agaggctgga atcaccgtcc cgacctttca gggcagaaga aaaaggttat ttgaccaacg   6060
gttcttactc ttagtcatca aaactctgtg cgggtcccgg ggagactggc ctagtccaag   6120
tcttcacata taagtgaggg acatgtttgt tttccttttta tttttgtgag aacacatttt   6180
tgttttgacg gggcacaaaa agccatagac ctgtatacta gtccttttcg agactagtct   6240
atgttagaat agttagaatg aagcatcata aaaaagacaa tttctgatgc ttcattctaa   6300
ctattcacga ggcatttctt tatcttttttt acacaagcca caaaaaaacgt cgtttttcac   6360
cgaaaccttg tgaacggaca taaaatgtcc ggatatacac gcggggtttt tgttccgaat   6420
ttttcaactt ttcaaaatgt gtgttttcga caatgggtgc atatgcacct atgagcaaaa   6480
aagccgcgtc cggtgaagtt tgcatatcat cttctttaca agtatataaa gcatacacca   6540
aacaatctgg actcactaac atttccagcc aatcagataa tttgcatagg tctggctcta   6600
gttaagtgaa gttgtttgtt ttaaaacaca aaacatattc ctaaaatatc tggactcggt   6660
ctcatttcca gccaatcaaa taagatggat atgtagctct ggatccatca atatgttgag   6720
ggctagaaaa gccgtgtgga ccactcaaac agacgcttgc tggctaatgt tgctttcaac   6780
```

-continued agggatttga ccaaatccgt acgaaaaatc acccaacctc gtgcgctcta ttaatttttt 6840
attctgtctt tcgtcgttgg gatattaaac cgtcatttat tttttctttt ttagaagtct 6900
cgtatgtagc tatccgaatg actcatgcat ttgcaaagct gcctaggaaa tgacaaaatt 6960
tgcgaatgag ttttgttatt ttctacccac atgaatgttc tcaggaaaat agatatttta 7020
cagatttgca gttcactcaa cacattttca aagagggcct cgcacacctt agcgttagcg 7080
agtgatatag atgcgcacac ctggcttact cctgcatcgt agcgcataac tgcataagta 7140
caccactgga attaggtaac tgtagcgaca agtcaatccg tcctgtcctg ccatacataa 7200
tgctaagcag ctgcgtatcc attgcggcag cggtggtgct gctgctaatc tcggcaccgg 7260
cggccgcagc agggcctccg ccgatgaaga tagggatgcc gggctgcaac accacctgcg 7320
gcaacgtaag cgtgccttac ccgttcggca tgggcccgaa gagttgttac tggccggggt 7380
tcaagctcac ctgcgacaac aacggaagca atctcccgcg gcttctcctc ggcgatggaa 7440
gtgccggcat tttcgaggtc gtcaagatct ccgtggagaa cactacgatg cacatcatca 7500
gccacggact gcaagccatc aacatgagag gcggctcggg ccggtggagc ctcggtgatg 7560
ctgagactga gagcatcggc gccggcaggt tgccctactt gctgcacccg gattcaaatg 7620
atttcatcct cacgggttgc aacgtgcagg cgacgcttct ggggaaccgc agcctcgcca 7680
gcggctgcgc ttcgttctgc ccggcttttg gtgatggtgg tggcggtaac ctagtttatt 7740
ctgggggaaa atccaatacc tgctccaaca tcggctgctg ccagtcgacc atccaaactg 7800
ccagcgcgtc ctacggcgtg gagctcaagc ggctcaacta cagcggcgtg tacagcaatt 7860
tcgatttgcc cgtgcacgtg ctcatcgccg aggtgggttg gttcgactta gaccacaatc 7920
gggaggtggt tatgaacctg tactgggagg aaaaccaaaa agaaaatctc tcgcggaagg 7980
ctgatcggct cagggtcccc gtgattctcg cgtgggcatt ggcacacgag gcagcagtga 8040
actctggcca tttgcattgc ccagaccacg cagcccggag catatgcaag agcgcccaca 8100
gcaattgcag tgtcggagac tttcaagtca gaggctattc gtgccagtgc agggagggct 8160
accagggcaa cccttacctc accggaggat gccaaggtga gtttacaatt tttttactga 8220
attatttgca ttgctttcca tatgtgtcac gtggttattt ttgttcgtgg acatatacac 8280
agatatcaaa gagtgcgatc aaaaagaaaa acatttctgc ttcggggact gtgaggaact 8340
gccgggctcg ttccagtgcc ggtgcccgaa cggaacgcat ggcaattaca caaagcccgg 8400
tggctgcatc atcatcgagt ctgaagacac aatcggaggt actcctagcc tgccgattac 8460
tagtgcgtgc aacaggagac aatggaacaa ttaatgttca ttagttaatt atctcgctcc 8520
atttatatat tcttgataaa atagtactag tagtaaatgt gtcaattgct tttcaggtca 8580
taataacttg ggtttaatca ttggtctctc ggtcgctagt ggcccattta ttctactttt 8640
ggttcttggt gcaatcctaa ctatccgtgg ttttaaccaa cgcaaggcga aggcgctgag 8700
acagaagttc tttactcaaa accgtggcca actattaaag caattggttt ctcacagggc 8760
cgacatcgca gagcggatgc tcatctcttt agaagagcta gagaaggcta ccaacaattt 8820
tgatcaagcc cgcaggctag gtggaggtgg acatggcact gtctacaaag ggattatgtt 8880
agacctgcat gttgtggcca tcaagaagtc aaatattgtc gtgaggagag aaatcgacga 8940
gttcataaat gaggttgcca tactctcaca gatcaaccat agaaatattg tgaagctccg 9000
tggatgttgc ctcgaggcag aagtgacgtt acttgcttac gagttcattt ccaatggaac 9060
actcgccgac catcttcacg cggaaaaagg aggatcgcta ccttggaaag ataggttaag 9120
gatcacaagt gaaataggca aagctattgc ttaccttcac tctgctatat cagtccctgt 9180

-continued

```
aatacacaga gatatcaaac cctccaacat acttcttgat gatgccttga cagcaaaagt   9240
gtcagacttt ggagcttcaa ggtacattat tcctgtggat caaacaggta caacaactac   9300
ggtgcaagga actatagggt acttagatcc tatgtattat tatactggac gcctaaccga   9360
aagtagtgat gtttatagct ttggagtcct tcttgttgaa ttgcttacta ggaggaagcc   9420
atctctgtat agatcttccg aaggtgatgg gcttgtcatg caatttgttg cactacttgc   9480
agaaggcaat ttggcaaaaa taatagaccc acaagttata gaggaggggg gtagcgcagt   9540
gaaagaagtt gctactctag ccatggagtg cgtgaaacta agagcagagg agcgaccaac   9600
catgaggcaa gtagagatgg cgctagaagc tctccaagca cccaataagc gtgtcggggc   9660
tgatttgata gaagaaacag atgagaagga atatgcagca acaggctatc catccaccag   9720
ccaacaagca aagaaaaatg aaggaagcag gtgttatagc caagaagatg agttcctgtt   9780
atctgcgaca taccctcgat agtttttgct tgcttgtaag tgaattttta gccatggtga   9840
attgtttctg ttattgtaaa tcagtgcgtg tttttatatg aatatatatg ccgaacagaa   9900
cttaagtgta tgcttcaaaa aaactgaatg cacccaacta tgttgttcta attttgcatg   9960
ctgccctgct ctcagtcttg atgatcatct atatatccat cttccacacg tactcacaag  10020
actgaccaag acactatcca tcatttcgtt gcacttatac gtatttattg atgtgtcgat  10080
ccttgtctcc attaaaaatt gtgcaacttg tggtagtaga agcaaggtag ccgctcgggt  10140
gttgggcatc ttatttaacc attgaacccc gcgatgtcat ttgatatctc agtatcgtct  10200
tgggaacatt gaactgcaca ccccagaatg caaactatac caacactatg gtacagtgca  10260
tgtaatgcaa caattggttt catctccacg caaaaattgg aattaaagca aacgctgcac  10320
atgcatgcat gctggttgct ggccctacac atgtacatag aacctctatg attcgagcgt  10380
gtgatcagca gggactggtg atgagtccaa atctcatctc cgtgttcaaa taggtacatg  10440
gcgtgtttcg gctattgagg ctcccagcag caaacacact cgagtcaagt ttctatgggt  10500
gttctcattg acctgtccct caacaatcca cttctgtact actaccgtgc aatataaccc  10560
atctgactac aacatgtggg ttaccattgt ttcattctac tctaattgcc cttctaacta  10620
ccctgtaatt cccctgtaaa gccccatgtg tctagcattg ctctcttcgc agtcttagca  10680
aatactattt actccgtacg tatgcgccca tgcagagacc ggtaaaggtt ttaactctca  10740
actgctaaca acgtactcta agtaactctc agctgctaag agcatctcca gccgtttgac  10800
cgcccaaggc gtcgaaaaag agcggcctag gagcgagccg gcgctagatc ggcccctggg  10860
gttcgtttct ccccagccac gcccccaggt gccccccccc ccccccaagg cgccccatat  10920
tcgaactcca tcgttcccgc tcaaagaaaa gcgatcatcg caatagttcg gcgattcagt  10980
gccacagttc ggtgattaaa taaaaggaca cgcagtagtt cggcgtacag aaaaggaagg  11040
acgcgggagg agtacatcaa acgtcgagct caacctccgg cggcggcgtc gtcggcgtac  11100
gcgggctgga aggagtcggc gcggcttctg ggctggtcgg catggcttct gtgctgccgg  11160
gcgcggcgga ggcatcgtcg gtggggctgg gcgtcgcgga ggcatcgtcg gtggggctgg  11220
gcgtcgcgga ggcatcgtca tcagctgccg ggctgggcag cggcggcggc gtcgccggta  11280
actgattcag gatgtggccg cgctccgcca agaaccacgc cttgagcttc tcgtcgccgc  11340
tttggagcat gtcagcgcca cccatcaaga aggcgaggtc gttgttcctc ttcttcgcgt  11400
attgagcttt gagttttgcg gcgccgttgg tccggagcaa gtcgagtttg acaacgttgt  11460
tcgtcatcaa aacagcccac ctcgcctcag ttttctcttc tcgctgggcg gccctggtct  11520
```

-continued tggcgtcggc gagacaatgt tcgatggact cctgcacgcg cgaggcagcc gactcggcgt 11580
atttcgcctt cttggcacct ttgttgccgt ccggttgccc gtcagccgcg cccgcggtcg 11640
gcgcgtccgg cttatacgtc tctttggctt tggcgagggt gcgcgggacg gctgcccatt 11700
tctcgcacct gtcgatccgc ctgaagacgt ggaggtactt gaactctgcg tcactgttgt 11760
catcgcggaa catggcgaac atgcgtagca gctgcgccga acgaaagaac atcagtcggc 11820
gtgctcggcg cgcacgaggc gaaagtgtgc gcgcacggcg gaaggcaaca gtatgagata 11880
cctgatcctc gacgctgatg ccgctctccg ggcgagccgc gacctcctcg acgatcccat 11940
gccatttgtt gcacgccgtt tggatgagcc cccaatggtt cgccatcacc gtcgccccac 12000
gcttcatgtg cacgcttttg aagtaggggt cgacgagctt ccgctcgtcg aactcggcct 12060
tgatgcggtc ccaatacgtc tcgatgctct ggttcgtgcc agtgaccggg tcgaggcaga 12120
caaccttcca cgcttcggcg aggcactcct cttccttgga cgcccacttg atgcgtggct 12180
cgccgggctt ggccgccttc ttcttcctct tcttcttgcc tttactcgtc ggcgccggtt 12240
cctcctcctc ctcttcctcc tcctccggct cttcctcgcc gtagtcgagc tcgtcgttca 12300
tgtcaccgag gtcaatcgag tcgtcctggg tagtgaaccc gggggaagcg gcggcggcgg 12360
ccgagccggc tgcgatgatg tcctccatgt cggcctccgt cgagtcggcg ttgccgagat 12420
gcatcaagga tgcggcttgc gagtagagaa tgcggcgaag aggtggcatc ggtgaggctg 12480
cgtagtccgg cggcgagtaa gtgtatggcg ggtactgcac gccggcgaat gctggcgagg 12540
gcgtgcgctg gacagggcgc ccatggggaa ggtgatgttg gggttgaagc caccatgggc 12600
gtccccatcg gcatagcccg gcgacgacgt gctccatggg tgcggcgacg acgagaaccc 12660
tgccggagag ccgacgcttt gctggctcca ggccgcgtat gggtgcccac cgggtggatt 12720
catcatcgcc gcgcacgccg cctccgcttg ttctgccacc accgcagccg tagcgtgcgc 12780
cgctttttcc ctggccttct tggccctgtt gcgcctgtcg gcggtgacga cctcccggtg 12840
ctccacatcc gccttccact cagcgttgct gatgccgggg ggcttggata gcggcgccct 12900
cggcttcctt tgcttctgct gggcggcggc ggctgtggga tccgtcgcgg cgcgcggcat 12960
cacgtacttc ttcggcggca tggcgggcgt ttggcgggag gagccgagcg tttggcgcga 13020
ggagccaagc gtatcagatt gggatattct tgatcgattt ggtcggatat gtagaattgg 13080
tgggaggaat ggagaagaga tgggagccta gggggaaagc gggagaaaac ggcgggaaag 13140
ggcttcagtc gccgacggag cggccccacg ccggttttcg cttgtgccgg cgcgcccagg 13200
cgacacccgg ccgcttgggt tcggggcggg atcgccggct ctgtatttcg cccaaaccgg 13260
cgctaaacga gatcctaggg tcgtgactgg gccgattttc ggccaccggc gctaaaaatt 13320
cgcctggggg gtctgttgga ggcgcggctg gagatgctct aacaacctac tctaagtgct 13380
ccctgtccaa ggaacccctg cttctcctcc ggctgtgtcc cgtgtgagca atgtcgtcct 13440
cacctccggc aaggccctgg ccaaccgtcg cccgccactt gttagaataa atctgaggca 13500
taccgtcgat catccgagaa ctaagcaatc acacgaggca cgacgccgag atttgttaac 13560
gaggttcacc gatatggcta catccccggg gcctgactac aggcgctcct ccccgtgaca 13620
ccgtcacaat accgcacccg gtcgccctgg acaccggcac atgctgccgg cttcccctgc 13680
gttccggtgc tattatgttg gcataggtta catcgtgtgt ctacccccgg tatatatgag 13740
aggcctagga tacaggtctc ctatttggag actccatatc ctatctaaac acaatgcaac 13800
tacaagtcca actgtaacct accttgtaca caatattcgg cacaactcta acaagcgcca 13860
tcctcgtctc gagatcggtc gctctttaac ctgagcggct gtcaagcaat ataaaaagtc 13920

-continued

```
tgacacctat attcatttat tctgtatatt catggtaggt ggtgaataat tggttgacca  13980
ccctcacgac atccttataa aaggaacaat attccgcggc aagtcccata gaaaattgac  14040
aaatattgtc cagaactgta tgataagaat tgttttcaag ctgtatgtaa atcgtaggct  14100
tgagagatat cgggaattaa tttaccagtg aggcgctctt gtagatactc ttggccacgt  14160
ctccgaggaa cagcaacatc acgaaatgag ttgctgtggt tgtcttgctg tggggaacca  14220
cctactggag gatcatggga acctgtagcc tgatcttccg ctctacgttg gacagatcca  14280
caagtagtac ctgaccaaat taccccatct cggcgatgat caggttcacg cccttctccg  14340
gtaggctgcc gtcctgtggt ttcagctcca ccacatagga cgcgtatccc atgagattga  14400
ggatggacga ctcataggag ccggcgttgc accaggcctt accgccgtga cacgtgcctg  14460
tggccatcaa ttgcggtttc cacttctttc atcatgttga gctagcaaag caggtggctt  14520
ctagtttctc tatgttagtg tgttagcttt agctagctag tcttcggaag gatcgatcta  14580
atcgctagct tagtatgtgc aagtctcccg aagcttgtac atacgcgtgt gtttctcggt  14640
ctcggccaaa agtattaaat gtcgttttaa gtccagctta atatattttt gccagaattt  14700
tccaatctat tgaagcaagc aactgaactc tattgcattc attttcctgt tgtcacccaa  14760
attccctact actcaaattt gtgataatca tctatcataa ttttcactcc tacccaaaga  14820
gaccaatcaa gacaccacct ttgccaaaaa agaagaccac aatcaagata ctatatgcta  14880
tatttaatta ggtggtactt cctctgatcc aaaatatagt gtgtattaga tttttttttc  14940
aatatcaaat cttgtaaact gtaagcaagt tcatagaaaa ataataatat caacacctat  15000
aatacaaagt caataccatt agattcatca aatatatttg cacttgattt ggtactccct  15060
cccacctgag ttaactccct atcctttgta aaagacctag ttgctcaccc acacacactc  15120
cccctcaacc agccgccgcg acctcctgac ctcgccgccc atggcgagga cgcagccgcc  15180
gtgagcctct gccgctgtgc cgccgagcca ctcgcccgcg cgccgccgcc gcttagacag  15240
gccgcccccg catcagccat ccccgagcag cagggaaacg ggcccaaccg ccggccaccg  15300
cgatgggctt tgccccggcg gcgagggtgc gggagggcgg gaaggaggga agggaaaatg  15360
atgcaacgga atattgtctg aataaaggga aatactaaaa actgaggaag cgaaactgaa  15420
gaagacatac actaaagaaa taaataaaag aatgaaggat tggaaaattg tgtgcaaaca  15480
aactgaatac tgacaactaa gaactaagag actaactaag agatctttct tggttttcat  15540
cagttttctt tgtgtcactg cttccattct ttttgcattg gtttttgttt ttgtttccct  15600
tatttccgtt tggttttcat tcgttctgtt ctcatttgat atggaatggg aaccttgttt  15660
tatacacaat taacacttat tcgaatacat gaaacgtttt ctgcatacgt ttgaaacatt  15720
tcttgtgtaa catttttcca attacatcat taacattgtt tttaaacata tatttattat  15780
ttcaaaaaaa ttcatacaca ttctatgttt tccgcataca tctgcaacat tttttgtgta  15840
cacatttaac attttcaaat acatgattaa catatttcaa aacatatctt tttttatgtt  15900
gcttttgcct acacattgta aattttttgt acacattaga aacatatttt tgtacatgct  15960
caacgttaac acatgattaa caatttttga aacatttatt atgtctattt tttgcataca  16020
aattgtacat tttttataca ctagtaaaaa aatacacgtc taacatttgc taaatatatg  16080
atcagtattt tataaaaaaa caattttatg agtaattgtt ttgatacaca ttgtacattt  16140
tctttatcta tcgaaaatat gattttatac acctttaaca ttttttctat acatgaataa  16200
tacattttta catatatata tattttgatg tctaatttct accatacata ttttacattt  16260
```

tatattaaca ttaggtacat ttttcattca ctttaaaaaa ataatacatg cttaattgtt 16320
tttcttattt tttatgtcta cttttgtcgt gcgcattttt aaattctcat atgcattagg 16380
aacattttttg tatatgcatt taacactttt catattatat ttttcgtgga tataacgtga 16440
ttttataata gacatattca ttatatttag gaatttaagc aaaagtaaaa aatttaaagt 16500
aacattataa aaaacgctaa gggcctttgg taccaggcaa ttggatcatg agcactgcat 16560
taatataaat catgagcacc tcgttgttaa atcaggcaat tcgattgtac ttctaacgcg 16620
ctttagcatt tttaacttca cgcaatacat gagcgtgaaa catgtatata gcacgttaaa 16680
aaagaagaaa gtctcgcatc tactcggcgg atcaatggaa tatggagatg tctatcaatc 16740
gatatcaatg cgaggactag gaattgtcat gcaacggatg cacaaagagc tataagtgta 16800
tgaaaactca acaaaaacta agtaggtatg catccaactt gcttcctcac gaagacctcc 16860
ggcatttgag aatgcccgtc atcggaatat acaattcgag ttatataacg aaaaagtccc 16920
agtagtatat gagtgtgaca acataggaga ctctttatat gaagaacatg ttgctactct 16980
gaagcacaag tgtaaaaaaa gtatagtaac attgcctctt ctctatttat ctgttatttt 17040
atttttatta ttttgttggg ttctttttgg cctttttttt ccatccggag tctcatcccg 17100
gcttgtgggg gaatcatagt ctccatcatc ctttcctcac tggcacaatg ttctaataat 17160
gatgatcatc acacttttat ttacttacaa cttgataact gaaacaatat gaccctataa 17220
gaatgcctct ggcagtgggg acgagcgatg gtcttttcct accaatctat ccccctagga 17280
gcatgcgcat agtactttgt ttcgataact aatagatttt tgcaataagt atgtgagttc 17340
tttatgacta attattgagt ccatggatta tacgcaccct cacccttcca tcattgctag 17400
cctcttcggt accgtgcatt gccctttctc acctcgagag ttggtgcaaa cttcgtcggt 17460
gcatccaaac cccgtgatac gatacgctct atcacacata agcctcctta tatcttcctc 17520
aaaacagcca ccatacctac ctattatggc atttccatag ccattccgag atatattgcc 17580
atgcaacttc catcatcatc atatacatga cttgagcatt cattgtcata ttgctttgca 17640
tgatcgtaag atagctagca tgatattttc atggcttgtc cgttttttat gtcattgcta 17700
cgctagatca ttgcacatcc tggtacactg ccagaggcat tcatatagag tcatgtcctt 17760
gttcagatat cgagttgtaa tattgagttg taagtaaata aaagtgtgat gatcatcatt 17820
attagagcat tgccccagtg aggaaaggat gatggagact atgattcccc cacaagtcgg 17880
gatgagactc cagactttat aaaaaaataa aagacgccaa agaagccgaa ataaaaaaag 17940
aggccaaata agcccaccaa aaaaattaaa aataaaagaa aaaaagaaaa gagaaaaaga 18000
gagaaggggc aatgttacta tccttttacc acacttgtgc ttcagagtac caccatgttc 18060
ttcatataga gagtctcttg agttatcact ttcatatact agtgggaatt tcattataga 18120
acttggcttg tatattccga tgatgggctt cctcaaatgt ccgaggtctt catgagcaag 18180
caagttggat gcacacccac ttagttttca gtttgagctt tcatacactt atagctctag 18240
tgcatctgtt gcacggcaat ccctactcac tcacattgat atctattgat gggcatctcc 18300
atcgcccgtt gatatgccta gttgatgtga gactatcttc tcctttttttg tcttctccac 18360
aaccaacatt ctattccatc tatagtgcta tgtccatggc tcacgctcat gtattgcgtg 18420
aaagttgaaa atgtttgaga acgtcagaag tatgaaacaa ttgcttggct tgtcatcggg 18480
gttgtgcatg atttgaatat tttgtgtggt gaagatggag catagccaga ctatatgatt 18540
ttgaagggat aactttcttc ggccttgtta ttttgaaaag acatgattgc tttattagta 18600
ggcttgaagt attattgttt ttatgtcaaa tgatagacta ttgctttgaa tcactcgtat 18660

-continued

```
cttaatattc atgccatgat tagatacatg atcaagaata tgctaggtag cattccacat  18720
caaaaattat ctttttatc atttacctac tcgaggacga gcaggaatta agcttgggga  18780
tgctgatacg tctccgtcgt atctataatt tttgattgtt ccatgccaat attctacaac  18840
tttcatatat ttttggcaac tttttatact atttttgggg actaacatat tgatccagtg  18900
cccagtgcca gttcctgttt gttgcatgtt tttgtttcgc agaatatcca tatcaaacgg  18960
agtccaaacg ggataaaaac ggacggagat tatttttgga atattcggag aatatgggaa  19020
ggaaaatcca tgcgagacgg tgcccgaggg aggcacgagg cagcagggcg cgcccctgac  19080
cctcgtgccc cccccccccc ccggtaaggc ggttgatgcc cttcttcggc cgcaagaaag  19140
ctatttttg gaaaaaaatc acgtcgcaga tttcagtcca atcggagtta cggatctcca  19200
tatatatacg gaacggtgaa agggcagcaa aacagaacgc agaaacagag agacagatcc  19260
aatctcagag gggctctcgc ccctcccatg ccatggaggc caaggaccag aggggaaacc  19320
gttctcccat ctagggagga ggtcaaggaa gaagaagaag gggccccctc tccccttctc  19380
ttccggtggt gccggaacgc tgccgtggcc accatcatca tcaccgcaat cttcaccaac  19440
aacttcaccg ccatcatcac caactcttgc cccctctatg tagcggtgta acctctctct  19500
tacccgctgt aatctctact taaacatggt gctccacgct atatattatt tctcaatgat  19560
gtatggctat cctatgatgt ttgagtagat ccgttttgtc ctatgggtta attgatgatc  19620
gtgattggtt tgagttgcat gtattattat tggtgctttc ctatggtgct ctccgtgtca  19680
cacaagcgtg agggatcccc gctgtagggt gttgcaatac gttcatgatt cgcttatagt  19740
gggttgcgtg agttactgaa acacaaaccc gagtaagggg gttgttgcgt atgggataaa  19800
gtggacttga tgctttaatg ctatggttgg gttttacctt aatgatcttt agtagttgcg  19860
gatgcttgct agagttccaa tcataagtgc atatgatcca agtagagaaa gtatgttagc  19920
ttatgcctct ccctcaaata aatttgcaat aatgattacc ggtctagtta tcgattgtct  19980
agggacaaat aactttctcg taacaaaaag ctctctacta aaactaattt agttgtgtct  20040
ttatctaaac aacccctact ttttatttac gcgctcttta ttttcttgca aaactttcca  20100
acaacaccta caaagtactt ctagtttcat acttgttcta ggtaaagcga acgttaagcg  20160
cgcgtagagt tgtatcggtg gtcgatagaa cacgagggaa tatttgttct acctttagct  20220
cctcgttggg ttcgacactc ttacttatcg aaagaggcta caattgatcc cctatacttg  20280
tgggttatca agggtcagga acattgattg gcaccttgaa agatttctca taattgaccc  20340
taagcccagt aaaagcagta taatgcacga tgaggttttt gacttgagca agttgtctgg  20400
catcagtagg cagtactagg attgtatcat caccatattg gatcacagga aaatctgggc  20460
aagcgtgact tctaatggga gaatgaatta aattctggtg gatagcttca ttgagcattg  20520
actgaagaag atcagctgcc agcacaaaga gtaaaggaga aacaggatcc ccttgcctga  20580
ctccttgtct gcagtgaaaa agtttccctg gcactccatt gagcagaacc gaagaagtac  20640
ctgaggaaag caagattgtg atccagttaa tccatctact tccaaaacct ttggctttca  20700
gaatagcaag aatggcttga tggttaagca gatcaaaagc tttctcaaag tctagtttga  20760
ggagtacaat aggctgttta gattgttgac attgatgcag atattcaaaa gcccatccca  20820
gacaatcatg aatagttcta ctcttgatga agccatattg attagtgtgc acaatcttga  20880
gaatcacagt ctgtaatcta ttggccaaaa gtttggtaat gatcttgata gtgaagttta  20940
gaagagaaat tggtctgaag ccactggctg tcactggatt gtccttcttt ggaatcaaag  21000
```

tgataaaaga ggcattgata ctctgaaggg agatcttccc atgatagaaa tcctcaatcc 21060
acttgtagaa atcttgggta atgatattcc aacaggcctt aataaaatct ccattaaaac 21120
catctgtccc aggtgctttg tcagaaggca ggtgcttaat aactgagtca atttcttgct 21180
tggtgaaggg ggcatccagt tcctgcaagt cctcaaccct ggtgatgagg ttgattaggt 21240
ttagagggtc tgagatctct ccagtctggc ccagtctttc tttaaatgca acccaaagaa 21300
ttgcagcttt ttcatgatgg tctgacattt ctactccttg atcattgcat aaactttgaa 21360
tgtagttatg tctgtatttg atggttgcct tagcctaatt tttttagagt tttcatcatc 21420
aaatttaacc catcaaattg ttgctctttg tctccaataa atcctttgaa aagacagcaa 21480
ttttaacaaa tgctctttta gcatttcctt gccattttgt tctatatctg tgagcactct 21540
gtattcctca aaaagatccc acatcaggat gacattattt gtggcctgaa tgttgctagc 21600
taggttggag aggcttttac tccaaaattt tagacctttc ctgagtcttt tgaattttcc 21660
agtgatgagt ttagcactgt cacttgccaa aatgggctgt tgccaaatag attggacaac 21720
atcttgaaaa tcatgattct gaagccagaa attttcaaat ctgaagactt gagctctagg 21780
aatgcttgta ccaattttta tgacaaaagg acagtgatca gaaacaggtt tggccaaagg 21840
aatagccata gtattgggat agttggaaga ccaattttca gagatgaata cccagtcaat 21900
tttctccagc aggggagctt gttgcatatt gctccaagta aaacttctac ctttcaaagg 21960
aatctcaact agggccagtt gactaattgc agcattgaaa tccatcatgt tattaatgtc 22020
accattgcct acattcctgt tagagggata tctgatataa ttgaaatctc ctgtgatgat 22080
ccaatcagat tcaacaggca tctgaatgtt tctgaaccat tccagaaaat tgtgttagta 22140
gaaaccaagg atgcatgctg atgcaccgtc cagccaaacc gaaccaaact atgccggagt 22200
ccagccaaac cgaaccatgc cggataccaa tccacgtaac gcaatttgga tagttttgca 22260
attcagtttg ctatgcgtcg cacgtgaagg acggtctccg gtttggatac gtccgacccg 22320
ggttgtatcc gatatttttt ccgcacgcag catggtggca tgcatgcatc catggtgcat 22380
cggccccgcc ttcgagggag gtgctcacgc gtggctcgct ggccccgcct cgtttgccac 22440
taccatcatg cacggcttgc cggactggcc tcaatttgcc gctgccgtcg agcgccgctc 22500
aggcgcagct ctctggacct gcctccatag ccgccatcgt cgcgcgcggc ttgtcagacc 22560
gggaccgtcc tccatagcag ctaccgtcaa gcgcccctca cgtgcggctc cctgccctgc 22620
ctttgcggtc tctgtcgttg cgccgcttgt cagactggcc ttcgcgcctc catgaccgcc 22680
cgtggcacat gacatagtgc gaaggtatgc atgtgcaaat gagtaacgca tcacaaattt 22740
tgttcattct aaatgatcaa gttcatgggc gccattatct tcttgaagac gtcgtggtgc 22800
tcctcttcgt gcctaggttc cgagtgaaaa cctttgtccg ttttggactc ggcagcgatg 22860
acgtgttgtg ccgttctccc tccctaggac gttgttgtgg agcttattag gtgttattgg 22920
tcgtagcgtg gtgttgtaaa cagttcctcc cgtgctctgt cttggtagct tagtcgcgtg 22980
agtcttgtgt ggtccgattg tcttgggatc ggtgttgtct gggattacct catcaccctg 23040
tatcgtttag tcgtgtactt tgtttgatct ttgctttata tatataaagc ggggcgaaag 23100
cctgtttcag gatccttcag tgacgttctc cttcccgagg gcgttgtctt ggagcaggtg 23160
ctggctggag ggggcatgag gtggtgcggt gtgtcatcta ccacgttggt gacggcgagt 23220
gtcggcagca tggcgcagtg aggtcccgga gttggaagtg tgttgatgga cgcgcatatg 23280
atggtagcac tgtctagcgt catggtggca tcgataacag ttgggccctg gcaaggccta 23340
tccattgatc tctcctgaaa atgggatggt ggaagatggc ggtggcagac tcgagagagt 23400

-continued gcgcatgcgg tgcacgctga aggtctgcta gaccggttgg tgttctcagc tcgccgtggg 23460
gcaacctggt gaggccaccg gattagatgg cgtgcgtgga tgcgccagtg cactccatca 23520
gacttgtacg tatagcgttt aggttgccag gaaggatgct ttgggtccat ccatctatct 23580
gctttgtcag actttgttta ataattttta aatatggttg catgcatcat tttgatgcag 23640
aggcaggggt aatcctcctt ttcgaaaaaa aaccaggcaa gaaatccgtt tctacatgta 23700
aaattccctt tgctaaaata tgtaaatttc cgtcttaaaa atggaataca tcctaacgga 23760
attctttctc aatatctgca actataaacc acctaaagaa atccctgtca aaaaacatcg 23820
cccaaggcaa atatctcgat ggttcttgat tttgctgtgt tcacttcatt gttactcaac 23880
actaacgtgc ctggcctagc acgagaaaga gaggttggaa tcatagcccc tgcctttaag 23940
ggcagaagaa aaagattatt tgaccaaggg ttctcagttc tcattcatgg aaacttcgtg 24000
cgggtcccag ggagacctgc caagtccaag tcttccccat ataagaccgt gacatttttg 24060
tttttaagag gcggaaaaag ccatggacct gtatactagt cttttctgag gctagtgttt 24120
gtgagaacga ccatgctcga tgtggaagta gtttggtcaa ctttgcttca ctaccacctt 24180
ctttacaagt actcccttca ttcctaaata taaaaccttt tagagattct actttgaact 24240
acatacccat gtatgttgtc cataatgaaa tctctaaaag gtcttgtatt taggaacgga 24300
ggaagtataa aacatacccc aaaaatctca actcacaaac atttcaagcc aatcaaacaa 24360
tttggatagc tctgcctgta gtaaagtgga gtactttgtt taaagaaata taacatatcc 24420
tcaaaataac tggactcaat atcatttcca tccagtaaaa taagttggat atatagctgt 24480
gcatctattg atgtggatgg ctgcaaaagc tatctacacc actcaaacag acgttagccg 24540
gctaatgttg ctttcaacag ggattggacc aaatccatac aaaaatcacc cgaccttacg 24600
ggtcaaaaag ttgaaaaaaa cttctcgcat gtagctacca gaatgtctcg tgtgcattcg 24660
cagagattca tatgaaatga cttaatttat gattattttt cgctacttct gcacacatgt 24720
ctcaaaaaca taaatagttg tgccaaattt gaaacttcac ataacatatt ttggattcat 24780
aaaagatttt cagttcactc aacatatttt caatgaaggt gttgacgtta atcagtggta 24840
tagagcatag acgtgtactg ctcgtctaca gctatgtagc agaagtacac ccattgaatt 24900
agctaactct agcgacaact caatccatcc cgtcacaacc cagaccgcgc gcggggcgac 24960
gaatggtatg aggcccaagc gggacgggtc agccacgtgg gagactatgg gtagaatcgg 25020
agaacgggcc aaatccaaaa aaaaacagcc cacctcatgt gctcacttga atttataaaa 25080
ttaaatcaaa tttgggtttt gaagcgtcaa aaagttcaaa aacaattctc gcatgtagct 25140
accagaatgt ctcgtgtgca tttgaagaga tccataagac atgacttaat ttatgaataa 25200
gtttcccccc gcggtttgct taccaccttc tttatactac aagtataaga catacaccaa 25260
aatatctcga ctcgctaaca tttccagcca atcaaataat ttggtagctc tacctataat 25320
aaaatggagt agttcaaaaa aacttgtccc caaaatatga ggactcaatc ccatttcgaa 25380
ccaatcaaat atatatagct gtgcatctat taatgtggag ggccacaaga gctatctaaa 25440
ccactcaaac aaacgctagc tggctaatgt tgctttcaat agggattgga cgaaatccaa 25500
acagaaaaca gcccaccaca tgtgctttct aaaaaatttg taatttgggt tttgaagcgt 25560
caaaaagctc aaaaaccaat ctcgcatgta gctaccagaa tgtctcgtgt gcatttgcag 25620
agatccataa gacacgactt aatttatgaa taggttttgt tatagtttca cagatgtctc 25680
ataaacataa atattcacac caaagttgaa acttcacata acatgttttc catttttaag 25740

-continued agatcttcag ttcgcctaac aaattttcaa tgacagcgat ggtctcatgc gtgttgacgt 25800
tagtgagtgg tggtatagag tatagacgtg taccactcgt ctactcctat atgtagcaga 25860
attgcgccaa ctgaaattag ctaactttag cgacaggtca atctatctcc gttccgccgt 25920
gatgctaacg agccggtgcg tattcatcac agcggtgctg caactactaa tctccttcct 25980
ggcggtcgcc ggggaaccac aaatcgggct gcccggctgc cagacccgct gcggcgacgt 26040
gagcgtgtcg tacccgttcg gcatgggacc caagaagtgc tactggccgg gtttgaagct 26100
cacctgcgac gaccgcggaa gcaaaccccc gcccagtatt tcgccgcaga ctacaactcc 26160
gacagctgct ccaacttggg ctgctgccag tcgtccatct tgtccagcag cacgtcctat 26220
gatgtcgagg tcaatcggct cggcgattgc ctgcggtacg gccctgtgcc cgacccgttt 26280
cccgacgatg ttccggtgaa tgtgctcatc gctgagaagg gttggttcta ccaggagtgg 26340
tcacgcaatg tcataaatgt tacctcgcgg cccaccgtga ttttcgagtg gcgggtgccg 26400
cttggtgccc cggtcccggt ggggccgtgc cccgacgacg cagcccggag catctgcaag 26460
agcacccata gctattgcac acaagagtgg tcaaataata cagtcggggc ctattcttgc 26520
cagtgcaact ccggctacac cggcaaccct tacctcaccg atggatgcca aggtgagttc 26580
acaacttcac atgtgcacat gtccatgttt tgttaactta attacagtat cttttattta 26640
cttagtctta aacaagacat gctaaactat attgtgtgca gatatccatg tgtgtgatca 26700
gaaagaaaaa catggctgct tcggccattg tgagcgactg cccggatatg ttagctgccg 26760
gtgcccagaa ggaacccatg gcaactactc catacccggg ggctgtgtcg cagacacaaa 26820
cacaggtatg acacgcacca gccagtcgat tactactact agtacgtgca aacaatggaa 26880
ctgttatttt aatgggcctg cttaagcaat tagttatagt aaacatatgt gcgtgtattg 26940
tttaactttc aggtaacttg gccttaatca ttggtttgtc ggctgcaagt ggcccattca 27000
ttctactttt ggttcttcgc atactcgtat tgtcaagtga ctttaaggaa caaaagctga 27060
ggatgttgag acggaagttc tttactcaaa accgtggaca actgctgaag cagttggtat 27120
ctcatagggc agacatcgca gagaggatgc tcatttcgtt agaagagcta cagaaggcta 27180
ccaacaattt caatcaagct cgcaggcttg gtggtggagg gcatggcact gtctacaaag 27240
ggatcttatc agacttgcat gttgtggcta taaagaagtc aaatattgtt gtgaaaagag 27300
aaattgacga gttcatcaat gaagttgcga tactctcgca gatcaaccat aggaatattg 27360
taaagcttcg tgggtgttgc ctcgagacag aagtcccttt attggcatac gagttcattt 27420
ccaatggaac acttagtgat catcttcaca cggaagaacc aagatcgtta acttggaaag 27480
ataagttaag gatcacaacc gaaacatgca aagctcttgc ataccttcac tctgctgttt 27540
cagtccctgt aatacataga gatatcaagc cttccaacat acttcttgat gatgccttga 27600
cagcaaaagt gtcagacttt ggagcttcaa ggtacattgc catgaatcaa acaggaacaa 27660
caactgcagt gcaaggaact ataggttact tggatcctac atattattat agcagacgcc 27720
tcacagaaag tagcgatgtt tatagctttg gagttcttct tattgaattg cttactagga 27780
ggaagccatc tttgtataga tccaatgaag gcgttgggct tgtcatggag ttcgttgcac 27840
tacttgcaga aggcaatcta tccgaaatac tagacccacc agttgtagaa gagggaggta 27900
gcaaagtcga agacgtagct aatctagctg tgtcgtgcgt gaaactgaga gcagaggagc 27960
gaccaactat gaggcaagtg gagatggcgc tggaagctct ccaagcacgc aaggagcatg 28020
tcatgggtga tttgatagaa gaaacaaacg ggaagaaaca tgcagcacca aattgtccat 28080
cgactagcaa acgaccaaag ggaagtggag caagcagatg ctatagccaa gaagaagagg 28140
tggtgttatc cgcaacattc cctcgatagt tttgcttgcc cggaagtgat ttttagtgat 28200
gttgtattct ttctactatt tggaatgagc gtgtgctatt gtatgaatat atgagttaca 28260
cataactcta gtgtattatt taaaataaat ttgaatgcac ccaactctgt tgtgctaatt 28320
ttgcatgttg tcgcgcaatc agcatttggt cttgatgatc gacagttcat cactagtgga 28380
aaaagtgtta gtcacaattt ttgttggtgg cgcaccgact cctaacaacg gtagtactat 28440
tttttccaaa taatggtggc gtcggacaat ttggtacgac attgatttga gcataccgct 28500
ggcatagaat ttttctcgta ccacataggc attttctgag tttttttccg tgtgctttcg 28560
ttttctatag cgtggcccat taggcatacg acagcggtat ccattaggcc cacgcgagca 28620
aaataaaact accctatcca gtaaagatca gtgtaggtcc gattcactaa cctatcattt 28680
tcgcctcttc ttcatccccc ttctcgaccg ccccgccacc gccactgccc gatgacgccg 28740
ctcttcgccg ccggaactgc gcggccgccg ccaactccgg caaggtgcta cactgtgtca 28800
tgtttggtcg ataggtgcta cgcacgacaa atcctttgcg tctggatgga cgagcgcagg 28860
acgatagcgt cgtcgggcgt cgtggtggca tcgacggacc ggtaaggatg atgcggatct 28920
atctcctgaa gatgggtcag cggtccgatg atgatggcgg cttctaaaac gtgtgcatgt 28980
gttgtacgca ttttgtctgc tgcgccggtg ttagttctga tacattatgt ggatggatcg 29040
gcgacgacac tggttttaga tatgggagtg agagccctcc acattatcga gtttttttaga 29100
tgtgagtagt ggtttcgggt ggcttgatgt atattcctgt tcgacctttg ttgaataata 29160
aataaagatg accgtatgca tcgattgatg cagaggccgg tgttttaacc tcctttttga 29220
aaggaaaagt actatgttag tagagtgctt agctgattaa ggatgaaaac tgcaatagct 29280
ccttactttc cctggtaaaa ctacaaatat cacaaatgca aacccaccca tcccggtagc 29340
ctcgtcaaat taaaataaaa aaaaatataa gaaaaggaaa atgcgaccgg cggctagcag 29400
ctccacctac cgcagctggc cggtcgtcgg tccttgcatc gcatccaagg cgacgccggc 29460
tccaccactg ccgccaccac tgattggtac cttaagctcc cgtgaagcta caagggagga 29520
ggccccctcg cctcccatcc attgttcctc aacagcttgg gtgccgagct cccccaccac 29580
cacactagac gcgctgggat tcattggatc cgctccagcg agcgagccgg attcagttca 29640
ccgagattat attcaccctt cccgtctgcc aactgattac ctcccttttc ccattctacc 29700
ctgggtgacc actctgctca ctctcactct ttctttctcc tctacgccgg ccgtgcacag 29760
cgcgacgccg acgaccgcat ccccccgacg ttgccgcagc cgccatacaa gtagaaggtg 29820
aggacccccct tcctctcctc ttcgtcctag ccagcggatc ctcagatctg agctgagtgg 29880
ggccgcagca agctcagact aaattgtttc ttacaaatct ttgagatgat ttccgtacca 29940
cgtatagaac tcctaatttc tcagcagaag aaatcaccgg gttctgggtt tgcgcacaaa 30000
gctttgattt tgttttgtgc tgtgctgtga aaattgagct cagatcttct tttagtagcc 30060
tgtgatttgt gcagtccaat ttgctgtgcg gtaccaacta agctcacatc tttttagtag 30120
aaagtaccta gtagttttta gagctttgct ttgcaagtag tacactagta ctacaaatta 30180
agctcacaca ttatattatt acagaggctc tgttttgttc agtactacaa agcttagatt 30240
ttgatttctg tactacgaat ttagctcaga tcttttttct gaacagcaag cttttaattt 30300
ctgcaaatag gaccgagatg gcaacctctc ccagctttgt gctacaccgc aagtactagg 30360
agcattgctg aatgccggat atagatcccc agatctaggc caagggtctc gctttctgct 30420
cactgttact tctatcatct ctccaatcga tccaaggtaa ttcatcgatt gcagcagcac 30480

-continued caccctctat ttagtgtgca ctttcttttg tgtgcaatcc atgcttttcc tttacaacga 30540
attgttggta gtctctgctg agtgaatcta catgaccatc cttcttttcc atttttttg 30600 catgtcacta ttgatgtgtg aaaggtagta ataaagagga ctcattttgt gtgcatcctt 30660
tgttttcagt tccagctcaa gccactggac cctgcaacta cttgcgagac agcacgggat 30720
atctatctct gcaacaagat ccgtctctca tctctctagt cgattcaagg tacatagctg 30780
aatccagcta cacaacactt actctagtta tttttctttt ttgaaagagc tgatcgtgtg 30840
tctttccatt tcaattgttg gtgtttgttc aaggtaatac tatatcggtt ttatttcgag 30900
ccgaatttct gtgcactgtc tttgcaagcc acattttcct ttggatttgt tactagcctc 30960
tagtgagtga atctgattat ccttcctgtt agcatgggat tgttgatgtg aaaaagcgag 31020
gtagtaatac aaaggactaa tttttatttc catgcttctt ttcagtacta gttcaagcgt 31080
gagcaaaccc tgcaaccaat ggcgggggtt ctggatgctt tggcatccta cgtgaccaac 31140
atgctcaccg agatggctaa agaggaggtg gccatgctaa tcggcgtgtc tgacgggatc 31200
aaagacctaa gcatcaagct tggggacctc aagaatttcc ttgctgatgc tgataggagg 31260
aacattaccg atgatagtgt gcgggggtgg gtgggcgaac tgaagcgtgc catgtacttg 31320
gccactgaca tcgtcgacct atgtcagctc aaggccatgg agcaaggtca aacaaaggac 31380
agggcgtgcc ggtgccttaa ccctctgctc ttttgcatgc ggaatcccct ccacgcccac 31440
gacatcggca cccgcatcaa gctgctcaac caaaatttgg atgatatttg caagaggggc 31500
agcagtttca atttcatcaa gctagaagcc taccaagacc aaaagaccac tcggtctccc 31560
gccactgacc ggaaaacaaa ttcactgatt gagcggtccg gtgtggttgg agagaagatc 31620
gaggaggaca cgagggcact tgtggaggtg cttacaaggg aggcggtagg tgacaagagt 31680
ggtcgcctca ttgtggtcgc cattgttggt atcggaggga ttggtaagac taccctcggc 31740
aagaaggtct tcaatgatga ggccatcgaa ggcaagttta ctaagaagat atggcttagc 31800
atcacacaag atttcaccga tgttgagttg ttaagtacga ccatcactgc cattggggca 31860
gatcttcctg gagggggtgg ggctccagac aaggccctac ttgtcgatgc tctcaagaac 31920
gccatcaagg acaagaagtt ctttcttgta ctagatgacc tgtgggatgt cgatgcatgg 31980
aacaaacatc taatgactcc ctttagctat ggtggccccg gtagtagagt cctcatcacc 32040
accagacatg acactgtagc ccgaagcatg aaagcctttc atccctacca tcatgttgac 32100
aaattagctc cacaagatgc ttggtcgttg ctcaagaagc aggtcggtac ttcccaaaac 32160
tcaatataat acacgtcgtt tgggactaca ctgttaagtt aatttgatct acacttgcat 32220
aagtctacca atctgaaatt tatatattta taatgcttcc ttgacttaaa tttcaccgta 32280
acacgagttc atcaagtttg tatatgaaat taggaagata ttaaacaata ttttcatttg 32340
tatgcatgat gtacggcttc tcaatttgtg gattattccg gacttaagtt tagcaattat 32400
cagggattgc atccagcttc tcaattagtt tctacttgca ggtagtcaca ggagaggaaa 32460
atgaaccaga agttgatatg ctagaagata ttgggctgca gattatagca aaatgtgatg 32520
gcttaccact tgctgtaaaa gttatgggtg gactcctatg caagaaggag aaaacacgac 32580
gtgattggca agacgtcttg aatgatgata tgtggtcagt atctcaaatg tcaaaggaac 32640
taaattatgc catatatctt agctatgagg atttgtcccc ttacttaaaa cagtgcttct 32700
tgcacttctc cctcaaacca aaaaagacag tgataactga tactgaaatg gtgtccatgt 32760
gggttggtga aggattggtt gaaggagaca catatactcg tagtttggaa gaagggaata 32820
agtactataa ggagctaata gtaaggaacc ttatagaggt agatacaaag taccctagtc 32880

```
aacttatttg caacatgcat gatgttattc gctcatttgc tcaatttgtg gctagggatg  32940
aaacactagt aggtcacaat ggagatacta tcaaaacaaa tcttagatca ccgaattatc  33000
ttagattatc catagaaacg aaaggagtgg gatccgatga atttgagtgg agatatttaa  33060
gagagcaaaa attgcttagg tctctaatat taactggaaa cctcaaaagt cagcctgggg  33120
attcgttgac tatcttccca agtctacgtc ttttgcatat agaatcagca aatattgctg  33180
cactagttga atctatgtac caactcaagc atttgagata tttggcatta aagaggactg  33240
atatgtgtag actaccagag aacatccatg agatgaaatt cctacagcat attagccttg  33300
aaggttgtga aagtttcatg aaacttcctg atagtattat caagctgcaa gggttgagat  33360
atcttgatat gggtgacaca cgtgtaagta gtattcctag gggtttccga gctcttacaa  33420
atttgacttc actatttggg tttccagcct atattgatgg tgactggtgt agtctggaag  33480
agttggggtc tctttcccag ctcaatgaac tttcactaca gagcctagaa aatgtatcta  33540
gtgccttgtt ggctgaaaag gcaagggtaa atgcaaagaa acaacttacc gtacttgctt  33600
taaaatgtgg tggtagagtg ggacatgggt tggtccaagg agaggtctct gagtctaagg  33660
aggaggagca aataattgag gcggtgtttg atgtgctctg tcctcagcct tgcatagaac  33720
acatcagaat agaaagatat tttggtcgtc ggctcccagg atggatggcg tccacagcta  33780
tggtgcccct cgagagcttg aagattctat gcctcgaaca cctgccctgc tgcacccaac  33840
tcccagatgg cttgtgcagg ctcccgtatt tggagtggat aaaagtgatg aatgctccag  33900
taatcaagtg tattggtcct gaattcgttc aacagtacaa tcagctgcac cgtccttcat  33960
ctcagttggc tgctacgttt cccaaactcc agatgttgga atttcacgga atggaggaat  34020
gggaggagtg ggtttgggag acggaagtga aagctatgcc cttattggag gaacttcgta  34080
tcacttcttg cagactgagc cgtatgcctc caggacttat gtctcatgca atggctttga  34140
agaagctaac aatatggagc gtccaatgtc tccactctct agagaacttt gtttctgtag  34200
ttgaactcga attgggaaac atacctgaac tggccatgat ctccaatctt ccaaaattac  34260
aaaaacttac aatcgagtgc tgcccaaagc tcgagatgct gcaggagatg gctgcactcc  34320
ggagactcga gctgaccatt ttcaacagcg aaaatcaact tccggtctac ctgcagactg  34380
tgaagcctag taatttgctg ctgacctgca acctagcggt actcacttcc atggctgagg  34440
gtgaatctag ctccgagtgg gacaagttca gtcatatcaa ccacgttgag gcttatgcag  34500
aggatggaga agatgagaag aaatggcacg tgttctacac atctgaatcc tgcaacatag  34560
agacaaatat tcatcaggta atactttggt ctctccctct ttcaatctag ctaataataa  34620
tattcttcct tattgttgtc tgttccatgc atatctattt tcatcagtat gatataggat  34680
agctgaatat atctcccact gtttttgttt tgcttgccag gatcgattgg tcgaagaaga  34740
ggagtaggct gaaactccag ccgaacgagg aaggaccata tgatgcaagg atatataagt  34800
atgtctgctg ttacaacttc aactagtttt gagatcgaat ccatgaaggg atacggggaa  34860
aagcatcagc cataatgcca tatacactta cctgcagaga ttcacacatc atactaattt  34920
cttgtgaagt gtgacatata cagttacgaa tttagagatg taaacttcgt ggcggactat  34980
ccagctggtg aagaaacatg gtgaccttgg caaggctctc ctttgtttag tgcaagcaac  35040
taatggagtt tagactactc tgctttgctc tgctctctga aagcagctca ggttgcaggt  35100
cctctgaagc agctgcgttt ttctttttct tttttcgcgg gtgtctttca ttcgttctct  35160
ggaaaactat gtttatttct gatagatcaa tcaatagtat actggaacac taaatactgt  35220
```

-continued

```
tagaacaaac ccaatcaaaa tgtactaatg ctctgcacct gtgagccaat caaacggatg  35280
tatatcaaag agaggcatca tattattgag gagccatcgg agattttctg aatttgccca  35340
gcttgaggat ggatctgggc cgccgccgcc gccagcgttg gggccgcagc tctgtacgcg  35400
atttgggatt gaacgatgag gccatcgaga ccaaattagc ttgcagggaa ggaccttttt  35460
gcaaattatg cgcctaaatc tgggccatca ttttcctatc cggtggtcca gatccacttt  35520
ttcgattttt ctaccataag catgttttct gttgtagttg ctcctcaaca gttgtacgta  35580
ttttgatggt agatggatca tggatggatg cataaggctg gtcatagtgg gaagtatcat  35640
atactagtat catgcatatg atactagtgt ataaactaca tccatagtgc atagtatcat  35700
agattagtat cataggtggt ctcatttatt gccatgcatg acacatagta gcattacatt  35760
aattatgtta cggtatctac ctatgttact ataactatct ctctcttctt taattgcctg  35820
ccacataagc atgtttgcga ttcccaagtg catgatacta cttatgttac ttccactatg  35880
accagcctaa tgcatcttca caatcatttg gcatcactgg ccgccggcca ccgtttttac  35940
tccattattt tttgttcagt gggtagtaag gaaccagtaa caattaataa ctggttaata  36000
gatgcatgga tctgataaat aagccaacta tttagcaact ttaggtgcta acttattaaa  36060
taaggtgtgc ttagcaataa caggttaagc acctatacat tgaggagttg agttgctaag  36120
atatttaatg cacttaacat ctcatttaag cacctttgca tttgaagagg tcaaagtgac  36180
agctagctta ctcagcttaa gataatttga gttccggaaa aggttttcgt cccgctttat  36240
ataattcaat cgaccgttca catgcaggac tagctgtaca acacagttga tgctacttgc  36300
tatagtgcca catgggtatc tgtaaccatt ccgtaattaa tggtttaacc caacggatgg  36360
agcttgaccc gttagacttg ccgctaagac tacccacaat gagagtaaca taggtagtaa  36420
catcacacat atctagataa aatagataat gtggcaagca ataaatgaag aaagagaggc  36480
atgtagtaac atagctagtt agtactacta gtataagtaa catcacacat agctacttag  36540
tactagcata ataaatgaag tgtcacagat gttactcccc actatagagg tagtaacata  36600
gagtagtaac atgggcatgt tactactcta tattactacc cattgtggct agtctaagcg  36660
tgcgagtcgt cgtcaaattt taactaatgt gctacaactt ccattggagg aacttcagat  36720
ctgttcttgc aaactgggtt atttgcctct aggacttatg tctcatgcaa tggctttgaa  36780
gacgctagaa atatggaacg tccatgctct caactcccta gagaactttg tttctgtagt  36840
tgagcttgac ttgttagaca tacccgaatt ggtcaagatc tcctatcttc caaaattaca  36900
aaagcctaaa atcaggtact gcccagagct caagacgctg caggagatgt ctgcactccg  36960
gagactcgag ctgaccattt tcaacagcga aaatcaactt ccggtctacc tgcagactgt  37020
aaagcctagt catttgctgc tgacctgcaa cctagcagta cttacttcca tggctgacgg  37080
tgaatctagc tcggagtggg acaagttcag tcatatcaag cacgtcgagg cttatgcaaa  37140
gggtggagaa gatgagaaga aatggcacgt gttctacaca tctgaatcct gcaacatact  37200
ttggtttccc tctctttcaa tctactagct aataatattc ttccttaatg taatctttgt  37260
tggttccatg catattgtta tcatcagtat tatataggat agctgaatgt atctcccact  37320
attttgtttt gcttgccagg atcgattggt ggaagaagag gactagaccg aaactcctac  37380
ggaacgagtt taggcgaaag gaccatatga tgcaaggata tacgtatgtc tactgttata  37440
gcttctacta gttttgggta ttcttaccta gtgccatgac cattggaatc tcatgtttaa  37500
tattatgatc gaatccatgc agggatacct ggaaagcatc agccataatg ccatatacac  37560
ttaacctgca gagattcgga caccacacta atttcttgcg aagtgtgaca tatacactta  37620
```

-continued

```
ctaattttga gatgtaaact tcttggcgta ctatctagct ggtgaagaaa catggtgacc  37680

ttggcaaggc tgtcctttgt gcagtgcaag caactaatgg agtttatgct actctgctct  37740

gctctgctct gttctctgaa agcagctcag gttgcagctt ctccattgtg gcgtttttct  37800

ttttcttttt cacgggtgtt ttgcgttggt tctctgaaaa actatgtttt ttttgataga  37860

ccagtcaata gtgtactggt atttcagctt ttaatttgta ctgcaaccac acaaatgact  37920

gtcagagagt gtagtttatt caagcttccg gctgctgatt tgtaactgta tgtcatagga  37980

attccgaatc agagtgatgt atactgggac caaacaaatg ttggtgagat cctggtccac  38040

gaagatcacg atgatgacct gctgactgga tgttctagct atctttagtt tcttcaatta  38100

gtgaaatcaa attagatcct ggctaatatg gtcaaatccg tggcacgtgg gtccacgaag  38160

aacacgtggg tctagctatc tgttgtttct tcaatcagtg cagtcaaatt aagttcaggt  38220

tttccccgca aaaaaaaaaa tttaagttca ggtttgttct ggggctcagg acatatgttg  38280

tggatggaag caactgtatc aggacatatt ggatcaggac atgaaactgt aattgcaggc  38340

atcaatgtat gtacctgcgc gtcttttctt tttatgaatg tgtgtacctg cgcgtcaatg  38400

cggacgatgc agatcttgcc gtccctcgtg cgtcctcgaa gggcgcatca tctaaatgag  38460

aagcaggctt ggtgcagccg tgctgagatc ctctcaaggg aaggtggaag ggagggcctg  38520

gagcacgaca tcctccttgc ggacttacct ggcgccggtg ctcctgtact gcagtggcgt  38580

acgggtttga tgatctgctc ctttctatgg agaagaatgg gtgtgctgcc aactcccgta  38640

tgctaaatac ttgtatagtt agaaggttac ttcagaaagg gggaatgccc agggctggga  38700

tttgtctgtc taaaattgat gagaggatct tcacccttga agcttccaca cctagcttgt  38760

tttttttctt ttttgcatgg gacacctagc ttctaaaatt taatcaagca ataagtagta  38820

tgtgaaaatg aaggaaggcg aatcaagctg tatgtatagg tacgtgcaga aggtaggtga  38880

gtgaaggacg agatttccaa tggctgcaaa ccgtactgca tatttcatgc acccacggcc  38940

aggtttgatc gttcacatct ctacatggcc attataaatt tacactagtc cttgatgcta  39000

gcttgcagct ttcttggcct tcctaggcag ctatactcta gaggttgtgg ttgccacttc  39060

actacatgat taaatttctc catggatacc atctatgtat gtgtgcgcgt cgttgataca  39120

tagttaggtg gtgggattgt gaggcagcag aaatctgatt gagcagtaaa ataaaggtat  39180

ttgcactatg atacagcgac agcgaaaaaa gaatagtgct tgcagtgttg cggaggagct  39240

agatgtgtca tcccaatagt gggagaaggg ttaaggaggg tatcgagcta gggagagatg  39300

gtgggtctgt gtggtgggtg tgtgaaccgc tgcagcctta gtgaggagcg tgtggttaca  39360

agggaccatc tagctttttt ccgtttggat gagtgcacgt ggttacagaa gccctagcat  39420

tagtggggag acagccaggc ctaggacaca gcagaattat gtgatttagc agcacaaacc  39480

aagtgtctgt tggcatgctt gttcgaaggc caaggttcaa tcactatgga atttt       39535
```

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11

```
tgtgtcatgt ttggtcgata gg                                            22
```

<210> SEQ ID NO 12

<211> LENGTH: 20
<212> TYPE: DNA
<213> ORGANISM: Artificial Sequence
<220> FEATURE:
<223> OTHER INFORMATION: primer

<400> SEQUENCE: 12
tcctcccttg tagcttcacg 20

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gcttccttga cttaaatttc accg 24

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
ccacatatca tcattcaaga cg 22

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
agatgagaag aaatggcacg tg 22

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
ccagtataca tcactctgat tcg 23

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
atattcaccc ttcccgtctg 20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18

-continued cttgccaatc acgtcgtgtt 20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gcaccgtcct tcatctcagt 20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tgcttttccc cgtatccctt 20

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
tagttcaagc gtgagcaaac c 21

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ccatgtttct tcaccagctg 20

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
ctgtagttga actcgaattg gg 22

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
atggctgatg cttttccccg 20

<210> SEQ ID NO 25
<211> LENGTH: 20
<212> TYPE: DNA

<213> ORGANISM: Artificial Sequence
<220> FEATURE:
<223> OTHER INFORMATION: primer

<400> SEQUENCE: 25
actacttgcg agacagcacg 20

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
gaagcatgaa agcctttcat cc 22

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
tccattagtt gcttgcactg c 21

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
tgagagacgg atcttgttgc 20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
agtagttgca gggtccagtg 20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
aaagctcgag atgctgcagg 20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tccgagtggg acaagttcag 20

-continued

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
cacaggagag gaaaatgaac ca 22

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
caagaaggag aaaacacgac g 21

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tgtggctagg gatgaaacac 20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
catcatatgg tccttcctcg 20

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
gcaaaatgtg atggcttacc ac 22

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
actagtgttt catccctagc 20

<210> SEQ ID NO 38
<211> LENGTH: 20
<212> TYPE: DNA
<213> ORGANISM: Artificial Sequence
<220> FEATURE:

-continued

<223> OTHER INFORMATION: primer

<400> SEQUENCE: 38
tgtgcactgt ctttgcaagc 20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gtgtagtccc aaacgacgtg 20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
gcatgatgta cggcttctca 20

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
gagtggagac attggacgct 20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
gatgaagata gggatgccgg 20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
agaacttctg tctcagcgcc 20

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
tagaacaaca tagttgggtg c 21

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gtgtcggaga ctttcaagtc 20

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
gatgtcggcc ctgtgagaa 19

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
tttctgcttc ggggactgtg 20

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
aacagaaaca attcaccatg gc 22

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
agcgagtgat atagatgcgc 20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
tgcaaatggc cagagttcac 20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
cttcacatgt gcacatgtcc 20

<210> SEQ ID NO 52
<211> LENGTH: 23
<212> TYPE: DNA
<213> ORGANISM: Artificial Sequence
<220> FEATURE:
<223> OTHER INFORMATION: primer

<400> SEQUENCE: 52
tattcataca atagcacacg ctc 23

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
tctgcaagag cacccatagc 20

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
aaaatcactt ccgggcaagc 20

<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55
gtcaaataat acagtcgggg c 21

<210> SEQ ID NO 56
<211> LENGTH: 23
<212> TYPE: DNA
<213> ORGANISM: Artificial Sequence
<220> FEATURE:
<223> OTHER INFORMATION: primer

<400> SEQUENCE: 56
tgaaggtatg caagagcttt gca 23

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
acacaggtat gacacgcacc 20

<210> SEQ ID NO 58
<211> LENGTH: 20

<212> TYPE: DNA
<213> ORGANISM: Artificial Sequence
<220> FEATURE:
<223> OTHER INFORMATION: primer

<400> SEQUENCE: 58
caagcctgcg agcttgattg 20

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
tatgccagcg gtcgaacaac 20

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
ggaacagcac ctcagggcac 20

<210> SEQ ID NO 61
<211> LENGTH: 727
<212> TYPE: DNA
<213> ORGANISM: Aegilops tauschii

<400> SEQUENCE: 61
tgtgtcatgt ttggtcgata ggtgctacgc acgacaaatc ctttgcgtct ggatggacga 60
gcgcaggacg atagcgtcgt cgggcgtcgt ggtggcatcg acggaccggt aaggatgatg 120
cggatctatc tcctgaagat gggtcagcgg tccgatgatg atggcggctt ctaaaacgtg 180
tgcatgtgtt gtacgcattt tgtctgctgc gccggtgtta gttctgatac attatgtgga 240
tggatcggcg acgacactgg ttttagatat gggagtgaga gccctccaca ttatcgagtt 300
ttttagatgt gagtagtggt ttcgggtggc ttgatgtata ttcctgttcg acctttgttg 360
aataataaat aaagatgacc gtatgcatcg attgatgcag aggccggtgt tttaacctcc 420
tttttgaaag gaaaagtact atgttagtag agtgcttagc tgattaagga tgaaaactgc 480
aatagctcct tactttccct ggtaaaacta caaatatcac aaatgcaaac ccacccatcc 540
cggtagcctc gtcaaattaa aataaaaaaa aatataagaa aaggaaaatg cgaccggcgg 600
ctagcagctc cacctaccgc agctggccgg tcgtcggtcc ttgcatcgca tccaaggcga 660
cgccggctcc accactgccg ccaccactga ttggtacctt aagctcccgt gaagctacaa 720
gggagga 727

<210> SEQ ID NO 62
<211> LENGTH: 361
<212> TYPE: DNA
<213> ORGANISM: Aegilops tauschii

<400> SEQUENCE: 62
gcttccttga cttaaatttc accgtaacac gagttcatca agtttgtata tgaaattagg 60
aagatattaa acaatatttt catttgtatg catgatgtac ggcttctcaa tttgtggatt 120

-continued

```
attccggact taagtttagc aattatcagg gattgcatcc agcttctcaa ttagtttcta    180

cttgcaggta gtcacaggag aggaaaatga accagaagtt gatatgctag aagatattgg    240

gctgcagatt atagcaaaat gtgatggctt accacttgct gtaaaagtta tgggtggact    300

cctatgcaag aaggagaaaa cacgacgtga ttggcaagac gtcttgaatg atgatatgtg    360

g                                                                   361


<210> SEQ ID NO 63
<211> LENGTH: 858
<212> TYPE: DNA
<213> ORGANISM: Aegilops tauschii

<400> SEQUENCE: 63

agatgagaag aaatggcacg tgttctacac atctgaatcc tgcaacatac tttggtttcc     60

ctctctttca atctactagc taataatatt cttccttaat gtaatctttg ttggttccat    120

gcatattgtt atcatcagta ttatatagga tagctgaatg tatctcccac tattttgttt    180

tgcttgccag gatcgattgg tggaagaaga ggactagacc gaaactccta cggaacgagt    240

ttaggcgaaa ggaccatatg atgcaaggat atacgtatgt ctactgttat agcttctact    300

agttttgggt attcttacct agtgccatga ccattggaat ctcatgttta atattatgat    360

cgaatccatg cagggatacc tggaaagcat cagccataat gccatataca cttaacctgc    420

agagattcgg acaccacact aatttcttgc gaagtgtgac atatacactt actaattttg    480

agatgtaaac ttcttggcgt actatctagc tggtgaagaa acatggtgac cttggcaagg    540

ctgtcctttg tgcagtgcaa gcaactaatg gagtttatgc tactctgctc tgctctgctc    600

tgttctctga aagcagctca ggttgcagct tctccattgt ggcgtttttc tttttctttt    660

tcacgggtgt tttgcgttgg ttctctgaaa aactatgttt tttttgatag accagtcaat    720

agtgtactgg tatttcagct tttaatttgt actgcaacca cacaaatgac tgtcagagag    780

tgtagtttat tcaagcttcc ggctgctgat ttgtaactgt atgtcatagg aattccgaat    840

cagagtgatg tatactgg                                                 858
```

USE OF YR4DS GENE OF *AEGILOPS TAUSCHII* IN STRIPE RUST RESISTANCE BREEDING OF TRITICEAE PLANTS

The present application contains a Sequence Listing that has been submitted electronically in ASCII format and is hereby incorporated by reference in its entirety. The ASCII copy, created on Mar. 12, 2021, is named Substitute Sequence Listing_ST25.txt and is 114,205 bytes in size.

TECHNICAL FIELD

The present invention relates to the technical field of molecular genetics and specifically relates to a use of Yr4DS gene of *Aegilops tauschii* in stripe rust resistance breeding of triticeae plants.

BACKGROUND TECHNOLOGY

Wheat stripe rush (or Yellow Rust) is a fungous disease caused by *Puccinia striiformis* f.sp. *tritici*., Pst, which endangers wheat production worldwide. Wheat stripe rust may usually causes 0.5%-5% yield loss, and when it occurs seriously, it may cause 5%-25% yield loss, or even extinction (Chen. 2005. Canadian Journal of Plant Pathology 27: 314-337). China is an area where wheat stripe rust is common in the world. There have been four major pandemics of wheat stripe rust (year 1950, 1964, 1990 and 2002), each of which resulted in a loss of hundreds of millions of kilograms of wheat yield, with a total loss of about 1.2 billion kilograms of wheat yield, of which the loss in 1950 was about 41.4% of the total wheat output in China (Chen Wanquan et al., 2013. Scientia Agricultura Sinica 46: 4254-4262).

The use of resistant varieties is the most economical, effective and environmentally friendly measure to prevent and control diseases. The defect of narrow genetic basis present generally in wheat breeding, which leads to the lack of effective resistance genes to stripe rust or the gradual loss of disease resistance of existing resistance genes (Kang Zhensheng et al., 2015. Scientia Agricultura Sinica 48: 3439-3453). In addition, the present of sexual reproduction and rapid virulence variation of wheat stripe rust which leads to the continuous evolution of new pathogenic varieties, which also causes many wheat varieties to “lose” disease resistance after being popularized for 3-5 years (Chen Wanquan, et al, 2013. Scientia Agricultura Sinica 46: 4254-4262). At present, the available wheat resources for disease resistance are increasingly scarce and the situation is grim. Therefore, the separation of new resistance genes is an urgent problem to be solved in wheat breeding for disease resistance. The separation of new resistance genes may broaden the wheat resistance source and promote the cultivation of resistant varieties; and may carry out polygene pyramiding with known genes by a method of gene engineering or molecular marker-assisted selection, and to cultivate a breeding germplasm material with durable resistance and broad-spectrum resistance.

The utilization of resistance genes is an important means to control stripe rust. Hundreds of resistance genes have been located in the genomes of wheat and its related plants all over the world. However, due to the huge and complex wheat genome, the number of resistance genes with known sequences is very limited. Up to now, only five genes, Yr5, Yr7, Yr15, Yr18 and Yr36, have been cloned (Fu et al. 2009. Science 323: 1357-1360; Krattinger et al. 2009. Science 323: 1360-1363; Marchal et al. 2018. Nature Plants 4:662-

668; Klymiuk et al. 2018. Nature Communications 9:3735), which greatly limits the effective utilization of stripe rust resistance genes in wheat and other crops breeding.

CONTENT OF INVENTION

In view of the above existing technology, in order to solve the difficulty of lack of disease resistance gene resources, the present invention provides a new gene Yr4DS isolated from *Aegilops tauschii* (*Ae. tauschii* ssp. *strangulata*), and it is confirmed by functional verification that the expression of the gene can improve the level of stripe rust resistance of wheat and barley. With the present invention, the Yr4DS gene for resistance to stripe rust can be applied to the disease resistance breeding of wheat family plants to promote the cultivation of stripe rust resistance wheat and barley varieties or germplasm materials.

In order to achieve the above purpose, the present invention adopts the following technical solutions:

In the first aspect of the present invention, a stripe rust resistance gene, which is named Yr4DS gene is provided, the Yr4DS gene is the nucleic acid described in any oi the following a) to j):

a) Nucleic acid, consisting of the base sequence shown in SEQ ID NO: 1;
b) Nucleic acid, consisting of the base sequence shown in SEQ ID NO: 3;
c) Nucleic acid, consisting of the base sequence shown in SEQ ID NO: 5;
d) Nucleic acid, consisting of the base sequence shown in SEQ ID NO: 7;
e) Nucleic acid, consisting of the base sequence shown in SEQ ID NO: 9;
f) Nucleic acid, consisting of the base sequence shown in SEQ ID NO: 10;
g) Nucleic acid, consisting of the base sequence encoding the protein shown in SEQ ID NO: 2;
h) Nucleic acid, consisting of the base sequence encoding the protein shown in SEQ ID NO: 4;
i) Nucleic acid, consisting of the base sequence encoding the protein shown in SEQ ID NO: 6;
j) Nucleic acid, consisting of the base sequence encoding the protein shown in SEQ ID NO: 8.

Wherein, the full-length cDNA TV1 sequence of Yr4DS gene is shown in SEQ ID NO: 1; the full-length cDNA TV2a sequence of Yr4DS gene is shown in SEQ ID NO: 3; the full-length cDNA TV3 sequence of Yr4DS gene is shown in SEQ ID NO: 5; the full-length cDNA TV4 sequence of Yr4DS gene is shown in SEQ ID NO: 7; the full-length expression frame of Yr4DS genome includes promoter, genome coding region and terminator, and the nucleotide sequence of Yr4DS is shown in SEQ ID NO: 9 or SEQ ID NO: 10.

In the second aspect of the present invention, a protein encoded by the stripe rust resistance gene is provided, and the amino acid sequence of the protein is shown in SEQ ID NO: 2, SEQ ID NO: 4, SEQ ID NO: 6 or SEQ ID NO: 8.

Wherein, the protein Yr4DS protein TV1 encoded by the full-length cDNA TV1 of Yr4DS gene is shown in SEQ ID NO: 1, and its amino acid sequence is shown in SEQ ID NO: 2; the protein Yr4DS protein TV2a encoded by the full-length cDNA TV2a of Yr4DS gene is shown in SEQ ID NO: 3, and its amino acid sequence is shown in SEQ ID NO: 4; the protein Yr4DS protein TV3 encoded by the full-length cDNA TV3 of Yr4DS gene is shown in SEQ ID NO: 5, and its amino acid sequence is shown in SEQ ID NO: 6; the protein Yr4DS protein TV4 encoded by the full-length cDNA TV4 of Yr4DS gene is shown in SEQ ID NO: 7, and its amino acid sequence is shown in SEQ ID NO: 8;

Recombinant expression vectors, transgenic cell lines or genetically engineered bacteria carrying the above-mentioned stripe rust resistance genes are also the protection scope of the present invention.

In the third aspect of the present invention, the DNA fragments described in any of the following a)-f) is provided as the stripe rust resistance gene in the application of the control of stripe rust of wheat and barley or plant breeding;

a) cDNA fragments shown in SEQ ID NO: 1, SEQ ID NO: 3, SEQ ID NO: 5 or SEQ ID NO: 7;
b) cDNA fragments of the amino acid sequence shown in encoded SEQ ID NO: 2, SEQ ID NO: 4, SEQ ID NO: 6 or SEQ ID NO: 8:
c) DNA fragments shown in SEQ ID NO: 9 or SEQ ID NO: 10;
d) DNA fragments of the amino acid sequence shown in encoded SEQ ID NO: 2, SEQ ID NO: 4, SEQ ID NO: 6 or SEQ ID NO: 8;
e) cDNA fragments or DNA fragments, the encoded protein is functionally equivalent to the protein shown in SEQ ID NO: 2, SEQ ID NO: 4, SEQ ID NO: 6 or SEQ ID NO: 8, however, there are substitution, deletion or insertion of one, several or dozens of amino acids in the amino acid sequence;
f) cDNA fragments or DNA fragments, which are hybridized with the DNA fragments of a) or c) under strict conditions and encodes the protein shown in SEQ ID NO: 2, SEQ ID NO: 4, SEQ ID NO: 6 or SEQ ID NO: 8.

In the fourth aspect of the invention, the application of the DNA fragments described in any of the following 1)-4) in the control of stripe rust of wheat and barley or plant breeding by regulating the expression of stripe rust resistance genes is provided;

1) DNA fragments, whose transcripts up-regulate the expression of the stripe rust resistance gene shown in at least one of SEQ ID NO: 1, SEQ ID NO: 3, SEQ ID NO: 5, SEQ ID NO: 7, SEQ ID NO: 9 or SEQ ID NO: 10 in plant cells;
2) DNA fragments, whose translation products up-regulate the expression of the stripe rust resistance gene shown in at least one of SEQ ID NO: 1, SEQ ID NO: 3, SEQ ID NO: 5, SEQ ID NO: 7, SEQ ID NO: 9 or SEQ ID NO: 10 in plant cells;
3) DNA fragments, whose transcripts up-regulate the transcribed RNA of the stripe rust resistance gene shown in at least one of SEQ ID NO: 1, SEQ ID NO: 3, SEQ ID NO: 5, SEQ ID NO: 7, SEQ ID NO: 9 or SEQ ID NO: 10 in plant cells;
4) DNA fragments, whose translation products up-regulate the encoded protein by the stripe rust resistance gene shown in at least one of SEQ ID NO: 1, SEQ ID NO: 3, SEQ ID NO: 5, SEQ ID NO: 7, SEQ ID NO: 9 or SEQ ID NO: 10 in plant cells;

In the fifth aspect of the present invention, an application of the recombinant expression vectors, transgenic cell lines or genetically engineered bacteria carrying the stripe rust resistance genes or a protein encoded by the wheat stripe rust resistance gene in breeding Triticeae plants with improved or reduced stripe rust resistance is provided, wherein the above-mentioned stripe rust resistance gene is shown in at least one of SEQ ID NO: 1, SEQ ID NO: 3, SEQ ID NO: 5, SEQ ID NO: 7, SEQ ID NO: 9 or SEQ ID NO: 10; preferably, the Triticeae plants axe wheat or barley.

In the sixth aspect of the present invention, a method for breeding stripe rust resistant wheat is provided. The cultivation method comprises: transferring stripe rust resistant genes shown in at least one of SEQ ID NO: 1, SEQ ID NO: 3, SEQ ID NO: 5, SEQ ID NO: 7, SEQ ID NO: 9 or SEQ ID NO: 10 into wheat or barley to obtain stripe rust resistant wheat or barley; or up-regulating the expression of the stripe rust resistance gene shown in at least one of SEQ ID NO: 1, SEQ ID NO: 3, SEQ ID NO: 5, SEQ ID NO: 7, SEQ ID NO: 9 or SEQ ID NO: 10 in wheat or barley genome, and screening to obtain wheat or barley plants with improved stripe rust resistance.

In the above-mentioned breeding method, the method of transferring the stripe rust resistance gene into wheat or barley comprises: polyethylene glycol method, agrobacterium-mediated method or biolistics bombardment.

In the above-mentioned cultivation method, the method of up-regulating the expression of stripe rust resistance gene in wheat or barley genome comprises: introducing DNA fragments which are able to activate or improve the transcription level or translation level or protein activity of wheat stripe rust resistance gene; or control the synthesis of specific small RNA molecules and up-regulate the accumulation of wheat stripe rust resistance gene mRNA.

The specific small RNA molecules include microRNA (miRNA), small interfering RNA (siRNA) or artificial microRNA (amiRNA).

In the seventh aspect of the present invention, a method for breeding wheat or barley with reduced stripe rust resistance is provided. The method comprises: suppressing the expression of the stripe rust resistance gene shown in at least one of SEQ ID NO: 1, SEQ ID NO: 3, SEQ ID NO: 5, SEQ ID NO: 7, SEQ ID NO: 9 or SEQ ID NO: 10 in wheat or barley genome, and screening to obtain wheat or barley plants with reduced stripe rust resistance.

In the above methods, the method for suppressing the expression of stripe rust resistance genes in wheat or barley genome comprises: mutating or knocking out all or part of the sequences of the gene shown in at least one of SEQ ID NO: 1, SEQ ID NO: 3, SEQ ID NO: 5, SEQ ID NO: 7, SEQ ID NO: 9 or SEQ ID NO: 10 in wheat or barley; or interfering with the expression of the gene shown in at least one of SEQ ID NO: 1, SEQ ID NO: 3, SEQ ID NO: 5, SEQ ID NO: 7, SEQ ID NO: 9 or SEQ ID NO: 10 by using interfering RNA; or using a gene silencing system to silence the gene shown in at least one of SEQ ID NO: 1, SEQ ID NO: 3, SEQ ID NO: 5, SEQ ID NO: 7, SEQ ID NO: 9 or SEQ ID NO: 10.

In the eighth aspect of the present invention, a molecular marker for identifying wheat stripe rust resistance genes is provided, which has three markers named Yr4DS-PM, Yr4DS-GM and Yr4DS-TM, respectively. The above three molecular markers can be used to distinguish different *Aegilops tauschii* families with stripe rust resistance and susceptible stripe rust.

Wherein, Yr4DS-PM is a PCR marker designed based on the promoter region of Yr4DS gene, and the nucleotide sequence of which is shown in SEQ ID NO: 61.

The primers for amplification of Yr4DS-PM are Yr4DS-FP1 (SEQ ID NO: 11) and Yr4DS-RP1 (SEQ ID NO: 12). If the length of the amplified band is 727 bp, it is closely linked with the high resistance of *Aegilops tauschii* to wheat stripe rust; and if not amplified or the amplified product is 575 bp, then it is suggested that the corresponding *Aegilops tauschii* should not be resistant to wheat stripe rust.

The Yr4DS-GM is a PCR marker designed based on the coding region of Yr4DS gene, and the nucleotide sequence of which is shown in SEQ ID NO: 62.

The primers for amplification of Yr4DS-GM are Yr4DS-FP2 (SEQ ID NO: 13) and Yr4DS-RP2 (SEQ ID NO: 14). After the amplified product was digested with HaeIII enzyme, if a 361 bp band appeared, closely linked with the high resistance of *Aegilops tauschii* to wheat stripe rust; and if two bands (240 bp and 121 bp) appeared, then it is suggested that the corresponding *Aegilops tauschii* is not resistant to wheat stripe rust.

Yr4DS-TM is a PCR marker, which is designed based on the terminator region of Yr4DS gene, and the nucleotide sequence of which is shown in SEQ ID NO: 63.

The primers used to amplify Yr4DS-TM are Yr4DS-FP3 (SEQ ID NO: 15) and Yr4DS-RP3 (SEQ ID NO: 16). If the length of the amplified band is 858 bp, it is closely linked with the high resistance of *Aegilops tauschii* to wheat stripe rust; and if it is not amplified, the corresponding *Aegilops tauschii* should not be resistant to wheat stripe rust is suggested.

In the ninth aspect of the present invention, a method for obtaining a plant cell carrying the stripe rust resistance gene is provided, which is obtained by means of transgenic or genome editing.

In the tenth aspect of the invention, a method for obtaining a plant carrying the stripe rust resistance gene is provided, and the plant cells obtained by the above method regenerate into seedlings.

The beneficial effects of the present invention:

The present invention clones a new type of stripe rust resistance gene Yr4DS from *Aegilops tauschii* for the first time, which can effectively regulate the resistance to stripe rust of the Triticeae plants (especially wheat and barley), and enriches stripe rust resistance gene resources. The present invention found that the expression of Yr4DS provides a high-level function of resistance to stripe rust, which indicates that artificial manipulation of the Yr4DS gene can endow wheat and other Triticeae plants with resistance to stripe rust. The present invention can be used to improve the resistance to stripe rust of existing wheat, barley and other Triticeae plants through molecular marker assisted breeding, genetic transformation and gene editing based on Yr4DS gene, and to cultivate and create intermediate materials and production varieties for resistance to stripe rust.

DESCRIPTION OF FIGURE

Synthetic wheat 'Syn-SAU-93(AS2382/AS2388)' shows a good level of resistance of adult plant to stripe rust, with infection type ranging from 3 to 4 (infection type or IT; Line and Qayoum. 1992. USDA Technical Bulletin 1788). FIG. 3 shows the incidence of $M_3$ mutants (L68 and L91; Table 2) and wild-type controls (WT=Syn-SAU-93) after being infected with wheat stripe rust at the adult stage. Yr4DS gene mutant shows high susceptibility to wheat stripe rust (IT is between 8 and 9), while wild type control shows middle resistance to wheat stripe rust (IT is between 3 and 4).

SPECIFIC EMBODIMENTS

Figure 1:
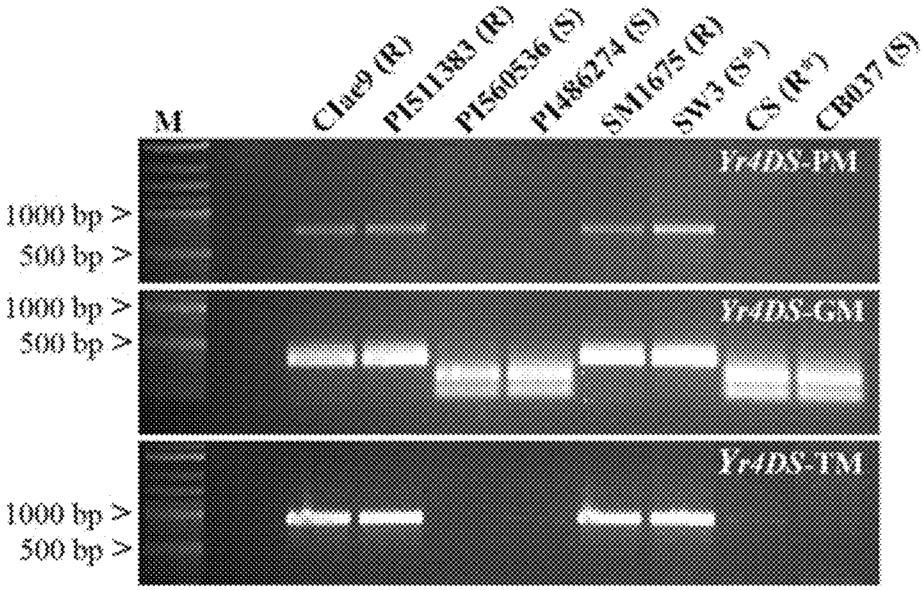
FIG. 1: identification of three effective markers Yr4DS-PM, Yr4DS-GM and Yr4DS-TM of YR4DS gene in *Aegilops tauschii*; wherein, the Yr4DS-PM and Yr4DS-TM are directly amplified products of PCR, and the Yr4DS-GM is the result of HaeIII digestion of PCR amplified products. CIae9 and PI511383 of *Aegilops tauschii* are highly resistant to wheat stripe rust. PI486274 and PI560536 of *Aegilops tauschii* are highly susceptible to wheat stripe rust. SM1675 and SW3 are hexaploid wheat carrying copies of disease-resistant Yr4DS, the Chinese Spring (CS) and hexaploid wheat CB037 do not carry disease-resistant Yr4DS gene. The letters in brackets behind the strain represent the resistance to stripe rust (R) or susceptibility to stripe rust (S), and the asterisk (*) indicates that its disease resistance is influenced by genetic background or other disease resistance genes. And M represents a molecular weight standard sample.

Noted that the following detailed description is exemplary and is intended to provide further explanation for the application. Unless otherwise specified, all technical and scientific terms used herein have the same meanings as commonly understood by those of ordinary skill in the technical field to which this application belongs.

As described in the background technology section, due to the huge and complex wheat genome, the number of stripe rust resistance genes with known sequences is very limited, which greatly limits the effective use of stripe rust resistance genes in wheat breeding. Based on this, the purpose of the present invention is to provide a new stripe rust resistance gene and use it for the breeding of wheat, barley and other Triticeae plants.

In the present invention, RNA sequencing (RNA-seq) and Bulked Segregant Analysis (BSA) are used to compare the leaf transcriptome of stripe rust resistant BSA pool and stripe rust susceptible BSA pool in F$_6$ generation of *Aegilops tauschii* segregation population at the adult stage. from which genes which are only expressed in stripe rust resistant parents (PI511383) and stripe rust resistant BSA pool are identified, and a gene which is specifically expressed on PI511383 and has NBS-LRR domain and is located on the 4DS chromosome of *Aegilops tauschii* is further screened out (thus named the Yr4DS gene). As a result, artificial manipulation of Yr4DS gene can improve the level of stripe rust resistance of wheat and barley. The present invention can be used for improving the stripe rust resistance level of wheat and other Triticeae plants and cultivating intermediate materials and production varieties with high stripe rust resistance.

The full-length cDNA sequence of Yr4DS gene is shown in SEQ ID NO: 1, SEQ ID NO: 3, SEQ ID NO: 5 or SEQ ID NO: 7; the amino acid sequence of the protein encoded by Yr4DS gene (i.e. Yr4DS protein) is shown in SEQ ID NO: 2, SEQ ID NO: 4, SEQ ID NO: 6 or SEQ ID NO: 8; Yr4DS genome full-length expression cassettes (including promoter, genome coding region and terminator), and its nucleotide sequence is shown in SEQ ID NO: 10.

The present invention relates to the application of cDNA, synthetic DNA and genomic DNA encoding Yr4DS protein of *Aegilops tauschii* and its homologous protein. Those skilled in the art can obtain Yr4DS gene-related cDNA and genomic DNA using conventional techniques. The preparation of cDNA comprises the following steps: a) message RNA (mRNA) is extracted from *Aegilops tauschii* or other species; b) the mRNA used as template to synthesize cDNA; c) PCR primers are designed according to the full-length cDNA sequence SEQ ID NO: 1, SEQ ID NO: 3, SEQ ID NO: 5 or SEQ ID NO: 7 of Yr4DS gene of the present invention, and then Yr4DS gene or its homologous gene is amplified from cDNA template; d) cloning the PCR product into plasmid carrier, and isolating the cDNA of Yr4DS gene or its homologous gene; e) the cDNA sequence of Yr4DS gene used as template, commercial service is commissioned to synthesize DNA artificially. Likewise, those skilled in the art can also extract genomic DNA from *Aegilops tauschii* or other species to create genomic DNA libraries (such as BAC, cosmid, fosmid and other types of libraries), and then use the DNA probes or PCR primers based on the nucleotide sequence (such as SEQ ID NO: 10) of Yr4DS genome full-length expression cassettes to screen the DNA library, then the positive plasmid carrying Yr4DS gene was obtained. The long fragment PCR method can also be adopted to amplify the Yr4DS gene or its homologous gene from the plant genomic DNA or plasmid DNA by using the specific PCR primers of the nucleotide sequence (such as SEQ ID NO: 10) of the full-length expression cassettes of Yr4DS genome of the present invention, and then the PCR product is connected to the cloning vector.

The present invention includes homologous DNA fragments of Yr4DS, as long as their encoded protein is functionally equivalent to Yr4DS protein (such as SEQ ID NO: 2, SEQ ID NO: 4, SEQ ID NO: 6 or SEQ ID NO: 8). As used herein, "functionally equivalent to Yr4DS protein" means that the protein encoded by the target DNA fragment is close to the Yr4DS protein (such as SEQ ID NO: 2, SEQ ID NO: 4, SEQ ID NO: 6 or SEQ ID NO: 8) of the present invention in terms of biological function and physiological and biochemical characteristics. The typical biological function of Yr4DS protein is to provide resistance to stripe rust. In order to verify whether Yr4DS gene is resistant to wheat stripe rust, ethylmethylsulfone (EMS) can be used to create a mutant population of 'synthetic wheat carrying Yr4DS gene' (Embodiment 4 and 5), and the mutant individuals with high susceptibility to wheat stripe rust can be identified by inoculation, and then the mutation situation of Yr4DS gene is analyzed, and the correlation between mutation frequency of Yr4DS gene and susceptible phenotype is analyzed. Genetic complementation can also be used to verify in order to clarify the function of Yr4DS gene. In the present invention, the Yr4DS genome full-length expression cassettes carrier (such as SEQ ID NO: 10) is introduced into the wheat 'CB037' and barley 'Golden Promise' (Embodiment 6) that are highly susceptible to stripe rust by using the biolistics bombardment technology; with the obtained transgenic plants, the contribution of Yr4DS transgenic expression to wheat and barley resistance to stripe rust was analyzed.

If the protein function encoded by DNA fragments is equivalent to Yr4DS protein (such as SEQ ID NO: 2, SEQ ID NO: 4, SEQ ID NO: 6 or SEQ ID NO: 8), the preferred source of these DNA fragments is monocotyledon, more preferably Gramineae, and most preferably Triticeae. These DNA fragments include alleles, homologous genes, mutant genes and derived genes corresponding to nucleotide sequences of the present invention (such as SEQ ID NO: 1, SEQ ID NO: 3, SEQ ID NO: 5 or SEQ ID NO: 7); the encoded protein is similar to the amino acid sequence of Yr4DS protein of the present invention (such as SEQ ID NO: 2, SEQ ID NO: 4, SEQ ID NO: 6 or SEQ ID NO: 8), or there is substitution, deletion or insertion of one, several or dozens of amino acids, which belong to the content of the present invention.

Genome editing technology, which can direct and knock out target genes, and be applied to animals and plants (Cheng and Alper. 2014. Current Opinion in Biotechnology 30:87-94). Partial genome editing technology, such as clustered, regularly interspaced, short palindromic repeats (CRISPR), has been successfully applied in wheat and other crops (Shan et al. 2014. Nature Protocols 9:2395-2410; Wang et al. 2014. Nature Biotechnology 32:947-951; Zhang et al. 2016. Nature Communications 7: 12617). Genome editing technology will cause deletion or insertion of one, several or dozens of bases in specific regions of target genes, which will lead to gene mutation, while DNA variation in transcription regions may cause variation or truncation of coding proteins (Wang et al. 2014. Nature Biotechnology 32:947-951). The base mutation of DNA in the transcription region will also cause the amino acid change of the encoded protein. Compared with Yr4DS protein (such as SEQ ID NO: 2, SEQ ID NO: 4, SEQ ID NO: 6 or SEQ ID NO: 8), the protein encoded by DNA fragment created by genome editing or base mutation may be replaced, deleted or inserted by one, several or dozens of amino acids, but as long as the protein encoded by DNA fragment is functionally equivalent to Yr4DS protein (such as SEQ ID NO: 2, SEQ ID NO: 4, SEQ ID NO: 6 or SEQ ID NO: 8), the DNA fragment belongs to the application content of the present invention. The DNA fragments defined by the present invention also include those mutations that have undergone base mutations but do not change the coding protein sequence, that is, conservative mutations.

For those skilled in the art, genome editing technology can be used to change the Yr4DS gene (such as SEQ ID NO: 1, SEQ ID NO: 3, SEQ ID NO: 5 or SEQ ID NO: 7) and its homologous gene sequence in the present invention. In addition, the variation of the target gene can be induced by mutation or identified by germplasm screening. For example, Slade et al. (2005) created EMS mutation population of wheat, and then identified the point mutation of target gene by Targeting Induced Local Lesions IN Genomes (TILLING) (Slade et al. 2005. Nature Biotechnology 23:75-81). Long-term evolution of natural germplasm has accumulated a large number of variations, and eco-tilling can also be used to identify the variations of target genes from natural germplasm or bred varieties (Till et al. 2006. Nature Protocols 1:2465-2477). For those skilled in the art, a mutant population of related plant materials can be created, and then individuals whose DNA fragments (such as SEQ ID NO: 1, SEQ ID NO: 3, SEQ ID NO: 5, SEQ ID NO: 7, SEQ ID NO: 9 or SEQ ID NO: 10) in the content of the present invention are mutated can be screened from thereof. Those skilled in the art can also identify the natural variation of the DNA fragment of the present invention (such as SEQ ID NO: 1, SEQ ID NO: 3, SEQ ID NO: 5, SEQ ID NO: 7, SEQ ID NO: 9 or SEQ ID NO: 10) from the natural germplasm or bred varieties of related plants. Therefore, the present invention also covers: a) all plant cells which are mutated by DNA fragments (such as SEQ ID NO: 1, SEQ ID NO: 3, SEQ ID NO: 5, SEQ ID NO: 7, SEQ ID NO: 9 or SEQ ID NO: 10) carrying the content of the present invention obtained by genome editing, mutagenesis or natural mutation screening; b) plants carrying plant cells of item a); c) asexual clones or plant progeny from plants of item b), as long as they still carry plant cells of item a); d) plant seeds, plant tissues or plant organs from items b) and c), as long as they still carry the plant cells of item a).

For those skilled in the art, there are many methods to obtain DNA fragments, so that their encoded protein is functionally equivalent to Yr4DS protein (such as SEQ ID NO: 2, SEQ ID NO: 4, SEQ ID NO: 6 or SEQ ID NO: 8), such as PCR method (Saiki et al. 1985. Science 230:1350-1354; Hemsley et al. 1989. Nucleic Acids Research 17:6545-6551; Landt et al. 1990. Gene 96:125-128), DNA recombination technology and DNA artificial synthesis technology (Kosuri and Church. 2014. Nature Methods 11:499-507). It can be said that for those skilled in the art, it is a conventional technique to obtain DNA fragments highly homologous to Yr4DS gene from wheat or other plants, and the corresponding DNA fragments can be obtained by screening genomic DNA or cDNA library by using PCR primers corresponding to the nucleotide sequence of the present invention (such as SEQ ID NO: 1, SEQ ID NO: 3, SEQ ID NO: 5, SEQ ID NO: 7, SEQ ID NO: 9 or SEQ ID NO: 10) or DNA probes corresponding to the nucleic acid sequence of the present invention (such as SEQ ID NO: 1, SEQ ID NO: 3, SEQ ID NO: 5, SEQ ID NO: 7, SEQ ID NO: 9 or SEQ ID NO: 10). With regard to the acquisition of DNA fragments, whether by PCR, DNA recombination, DNA synthesis or other similar technologies, as long as the protein encoded by these DNA fragments is functionally equivalent to Yr4DS protein (such as SEQ ID NO: 2, SEQ ID NO: 4, SEQ ID NO: 6 or SEQ ID NO: 8), these DNA fragments belong to the content of the present invention. The amino acid sequence encoded by these DNA fragments should be highly homologous to the amino acid sequence of the Yr4DS protein of the present invention (such as SEQ ID NO: 2, SEQ ID NO: 4, SEQ ID NO: 6 or SEQ ID NO: 8); as used herein, high homology means that the sequence identity of amino acid sequences between the two is at least 50% or higher, preferably 70% or higher, more preferably 90% or higher (such as 95%, 96%, 97%, 98% and 99% or higher) on regions that can be matched. The sequence identity of amino acid or nucleotide sequence can be determined by BLAST algorithm (Altschul et al. 1990. Journal of Molecular Biology 215:403-410; Karlin and Altschul. 1993. Proceedings of the National Academy of Sciences 90:5873-5877).

Molecular marker-assisted selective breeding makes use of effective molecular markers to accelerate the breeding process and improve the breeding effect. At present, the markers used effectively include Single nucleotide polymorphism, Cleaved amplified polymorphic sequence, Derived cleaved amplified polymorphic sequence, kompetitive allele specific PCR and the like. Those skilled in the art can use similar marker creation methods to design molecular markers (such as the Yr4DS-PM marker designed in the present invention; Embodiment 3, FIG. 1) that can be used for backcross breeding of stripe rust resistance genes and pyramiding of disease resistance genes according to DNA fragments of the Yr4DS gene (such as SEQ ID NO: 1, SEQ ID NO: 3, SEQ ID NO: 5, SEQ ID NO: 7, SEQ ID NO: 9 or SEQ ID NO: 10) or its homologous genes of the present invention; the use of relevant molecular markers to carry out molecular breeding of wheat and other crops for resistance to stripe rust belongs to the present invention.

In view of application, when a plant highly susceptible to stripe rust is introduced, the DNA fragments of the Yr4DS gene (such as SEQ ID NO: 1, SEQ ID NO: 3, SEQ ID NO: 5, SEQ ID NO: 7, SEQ ID NO: 9 or SEQ ID NO: 10) of the present invention or its homologous gene are likely to create a phenotype with high resistance to stripe rust. In other words, for the DNA fragments of Yr4DS gene (such as SEQ ID NO: 1, SEQ ID NO: 3, SEQ ID NO: 5, SEQ ID NO: 7, SEQ ID NO: 9 or SEQ ID NO: 10) or its homologous gene or the recombinant vectors of the DNA fragments, after they are introduced into the plant with high susceptibility to stripe rust, the transgenic cells are differentiated and regenerated to form a transgenic plant with high resistance to stripe rust, thereby transforming the susceptible plant into a disease-resistant plant. On the contrary, transgenic plants that regulate the expression of Yr4DS gene (such as SEQ ID NO: 1, SEQ ID NO: 3, SEQ ID NO: 5, SEQ ID NO: 7, SEQ ID NO: 9 or SEQ ID NO: 10) or its homologous gene can also be created. The "regulated expression" here includes three levels: DNA transcription level, cDNA translation level and protein product activity, including up-regulation and down-regulation. For example, DNA fragments excavated from the Yr4DS gene (such as SEQ ID NO: 1, SEQ ID NO: 3, SEQ ID NO: 5, SEQ ID NO: 7, SEQ ID NO: 9 or SEQ ID NO: 10) or its homologous gene according to the present invention can activate or improve the transcription level or translation level or protein activity of the gene, or insert them into a suitable plasmid carrier, and introduce the above DNA fragments or its carrying plasmid into plant cells carrying Yr4DS gene (such as SEQ ID NO: 1, SEQ ID NO: 3, SEQ ID NO: 5, SEQ ID NO: 7, SEQ ID NO: 9 or SEQ ID NO: 10) or its homologous gene, and the transgenic cells are differentiated to form transgenic plants with high resistance to stripe rust. For another example, for Yr4DS gene or its homologous gene, or the existence of microRNA (miRNA), small interfering RNA (siRNA) or artificial microRNA (amiRNA) interacting with it; by reasonably controlling the expression of specific small RNA molecules (amiRNA, miRNA or siRNA), the accumulation of Yr4DS gene or its homologous gene mRNA can be regulated, and the level of resistance to stripe rust of plants can be improved.

The present invention is not limited to plasmid carriers used for carrying out plant cell transformation, as long as they can express carrier genes in plant cells. For example, use carriers that carry constitutive promoters (such as corn Ubi promoter, Christensen et al. 1992. Plant Molecular Biology 18:675-689) or leaf-specific promoters. The "plant cell" referred to in the present invention has various forms, including various single cells, multi-cells, plant tissues or organs with life omnipotence, which can be suspension culture cells, protoplast cells, plant slice tissues and plant callus, and their unified characteristics are that plants or part of plants can be formed through differentiation regeneration or asexual reproduction. The "plant cell" referred to in the present invention also covers cells from various plants, such as wheat, barley and other triticeae plants, whose unified characteristic is that plants or parts of plants can be formed through differentiation and regeneration or asexual reproduction.

For those skilled in the art, various methods can be used to introduce plasmid carriers into plant cells, such as polyethylene glycol (PEG), electroporation method, agrobacterium-mediated method, biolistics bombardment etc., and the transformed cells can be developed into transgenic plants. In the field of plants, various transgenic technologies tend to mature and are widely used. The above methods and other similar methods are applicable to the field of the present invention.

Transgenic plants carrying the DNA fragments of the present invention can be propagated in large quantities by obtaining their sexual offspring (such as seeds), asexual clones (such as adventitious branches, callus, protoplasts, etc.) and meristems (such as bud points, stem tips, root tips, etc.) in a sexual or asexual manner. Therefore, the present invention covers: a) all transgenic plant cells carrying DNA fragments of the present invention; b) plants carrying plant cells of item a); c) asexual clones or plant progeny from plants of item b), as long as they still carry plant cells of item a); d) plant seeds, plant tissues or plant organs from items b) and c), as long as they still carry the plant cells of item a). The resistance to stripe rust of transgenic plants or plants carrying transgenic cells obtained by the above methods will be different from that of wild-type control plants in theory. For example, Yr4DS gene of *Aegilops tauschii* (such as SEQ ID NO: 1, SEQ ID NO: 3, SEQ ID NO: 5, SEQ ID NO: 7, SEQ ID NO: 9 or SEQ ID NO: 10) or its homologous gene was introduced into the plants susceptible to stripe rust, and the plants with high resistance to stripe rust were created.

In summary, the present invention focuses on the application of Yr4DS gene (such as SEQ ID NO: 1, SEQ ID NO: 3, SEQ ID NO: 5, SEQ ID NO: 7, SEQ ID NO: 9 or SEQ ID NO: 10) in the field of triticeae plants resistance to stripe rust. The expression of Yr4DS gene or its homologous gene in leaves and other tissues by using the plants susceptible to stripe rust as receptors may transform stripe rust-sensitive plants into plants with high resistance to stripe rust. Therefore, it is speculated that Yr4DS and its homologous genes will play an important role in breeding wheat plants for resistance to stripe rust.

In order to enable those skilled in the art to understand the technical scheme of this application more clearly, the technical scheme of this application will be described in detail with specific embodiments below.

The test materials used in the embodiments and comparative examples of the present invention are all conventional test materials in the field and can be purchased through commercial channels. Test methods without detailed conditions are carried out according to conventional test methods or operating instructions recommended by suppliers.

In the present invention, *Aegilops tauschii* PI511383 arid PI486274 were used as parents to create a recombinant inbred line ($F_6$) of high generation hybridization. In order to test their resistance to stripe rust, the invention uses wheat stripe rust (Pst races including CYR29, CYR30, CYR31, CYR32, CYR33, CYR34, Gui 22-1, SY11-4, or HY46-8, etc.) for inoculation and identification. *Aegilops tauschii* is planted in greenhouse with long sunshine (16 h, 105 $molm^{-2}s^{-1}$), with daytime temperature of 25-30° C. and nighttime temperature of 15-20° C. *Aegilops tauschii* is inoculated by injection or shaking powder, then kept at 10° C., dark and high humidity (100%) for 24 h, and then transferred to artificial climate room: 8 h night, 12° C.; 16 h light, 18° C. In the present invention, water, conventional drugs and plant hormones for molecular biology experiments are purchased from Fisher Scientific, Pittsburgh, Pa., USA and Sigma-Aldrich, St. Louis, Mo., USA, the plant tissue culture medium is purchased from PhytoTechnology Laboratories, Overland Park, Kans., USA, the microbial culture medium is purchased from Becton, Dickinson and Company, Franklin Lakes, N.J., USA, and antibiotics and bialaphos are purchased from Gold Biotechnology, St. Louis, Mo., USA. The PCR primers and sequences involved in the present invention are shown in Table 1.

TABLE 1

PCR primers used in the present invention

| Name of the primers | Sequences of the primers (5' to 3' end) | Number of the sequences |
|---|---|---|
| YR4DS-FP1 | TGTGTCATGTTTGGTCGATAGG | SEQ ID NO. 11 |
| YR4DS-RP1 | TCCTCCCTTGTAGCTTCACG | SEQ ID NO. 12 |
| YR4DS-FP2 | GCTTCCTTGACTTAAATTTCACCG | SEQ ID NO. 13 |
| YR4DS-RP2 | CCACATATCATCATTCAAGACG | SEQ ID NO. 14 |
| YR4DS-FP3 | AGATGAGAAGAAATGGCACGTG | SEQ ID NO. 15 |

TABLE 1-continued

| PCR primers used in the present invention | | |
|---|---|---|
| **Name of the primers** | **Sequences of the primers (5' to 3' end)** | **Number of the sequences** |
| YR4DS-RP3 | CCAGTATACATCACTCTGATTCG | SEQ ID NO. 16 |
| YR4DS-FP4 | ATATTCACCCTTCCCGTCTG | SEQ ID NO. 17 |
| YR4DS-RP4 | CTTGCCAATCACGTCGTGTT | SEQ ID NO. 18 |
| YR4DS-FP5 | GCACCGTCCTTCATCTCAGT | SEQ ID NO. 19 |
| YR4DS-RP5 | TGCTTTTCCCCGTATCCCTT | SEQ ID NO. 20 |
| YR4DS-FP6 | TAGTTCAAGCGTGAGCAAACC | SEQ ID NO. 21 |
| YR4DS-RP6 | CCATGTTTCTTCACCAGCTG | SEQ ID NO. 22 |
| YR4DS-FP7 | CTGTAGTTGAACTCGAATTGGG | SEQ ID NO. 23 |
| YR4DS-RP7 | ATGGCTGATGCTTTTCCCCG | SEQ ID NO. 24 |
| YR4DS-FP8 | ACTACTTGCGAGACAGCACG | SEQ ID NO. 25 |
| YR4DS-FP9 | GAAGCATGAAAGCCTTTCATCC | SEQ ID NO. 26 |
| YR4DS-RP9 | TCCATTAGTTGCTTGCACTGC | SEQ ID NO. 27 |
| YR4DS-RP10 | TGAGAGACGGATCTTGTTGC | SEQ ID NO. 28 |
| YR4DS-RP11 | AGTAGTTGCAGGGTCCAGTG | SEQ ID NO. 29 |
| YR4DS-FP10 | AAAGCTCGAGATGCTGCAGG | SEQ ID NO. 30 |
| YR4DS-FP11 | TCCGAGTGGGACAAGTTCAG | SEQ ID NO. 31 |
| YR4DS-FP12 | CACAGGAGAGGAAAATGAACCA | SEQ ID NO. 32 |
| YR4DS-FP13 | CAAGAAGGAGAAAACACGACG | SEQ ID NO. 33 |
| YR4DS-FP14 | TGTGGCTAGGGATGAAACAC | SEQ ID NO. 34 |
| YR4DS-RP14 | CATCATATGGTCCTTCCTCG | SEQ ID NO. 35 |
| YR4DS-FP15 | GCAAAATGTGATGGCTTACCAC | SEQ ID NO. 36 |
| YR4DS-RP15 | ACTAGTGTTTCATCCCTAGC | SEQ ID NO. 37 |
| YR4DS-FP16 | TGTGCACTGTCTTTGCAAGC | SEQ ID NO. 38 |
| YR4DS-RP16 | GTGTAGTCCCAAACGACGTG | SEQ ID NO. 39 |
| YR4DS-FP17 | GCATGATGTACGGCTTCTCA | SEQ ID NO. 40 |
| YR4DS-RP17 | GAGTGGAGACATTGGACGCT | SEQ ID NO. 41 |
| RLK1-FP1 | GATGAAGATAGGGATGCCGG | SEQ ID NO. 42 |
| RLK1-RP1 | AGAACTTCTGTCTCAGCGCC | SEQ ID NO. 43 |
| RLK1-RP2 | TAGAACAACATAGTTGGGTGC | SEQ ID NO. 44 |
| RLK1-FP3 | GTGTCGGAGACTTTCAAGTC | SEQ ID NO. 45 |
| RLK1-RP3 | GATGTCGGCCCTGTGAGAA | SEQ ID NO. 46 |
| RLK1-FP4 | TTTCTGCTTCGGGGACTGTG | SEQ ID NO. 47 |
| RLK1-RP4 | AACAGAAACAATTCACCATGGC | SEQ ID NO. 48 |
| RLK1-FP5 | AGCGAGTGATATAGATGCGC | SEQ ID NO. 49 |
| RLK1-RP5 | TGCAAATGGCCAGAGTTCAC | SEQ ID NO. 50 |
| RLK2-FP1 | CTTCACATGTGCACATGTCC | SEQ ID NO. 51 |
| RLK2-RP1 | TATTCATACAATAGCACACGCTC | SEQ ID NO. 52 |
| RLK2-FP2 | TCTGCAAGAGCACCCATAGC | SEQ ID NO. 53 |
| RLK2-RP2 | AAAATCACTTCCGGGCAAGC | SEQ ID NO. 54 |
| RLK2-FP3 | GTCAAATAATACAGTCGGGGC | SEQ ID NO. 55 |
| RLK2-RP3 | TGAAGGTATGCAAGAGCTTTGCA | SEQ ID NO. 56 |
| RLK2-FP4 | ACACAGGTATGACACGCACC | SEQ ID NO. 57 |
| RLK2-RP4 | CAAGCCTGCGAGCTTGATTG | SEQ ID NO. 58 |
| Actin-FP[1] | TATGCCAGCGGTCGAACAAC | SEQ ID NO. 59 |
| Actin-RP | GGAACAGCACCTCAGGGCAC | SEQ ID NO. 60 |

Note: The internal reference primers Actin-FP and Actin-RP in RT-PCR work on wheat, barley and Aegilops tauschii.

TABLE 2

Mutations of candidate genes in synthetic wheat mutants with high susceptibility to stripe rust[1]

| Mutant strain | Plant generation | RLK1 (RLK1-FP1/RP1) | RLK2 (RLK2-FP1/RP1) | Yr4DS (YR4DS-FP5RP5) | Yr4DS base substitution[2] | Yr4DS Amino acid substitution[3] |
|---|---|---|---|---|---|---|
| L30 | $M_3$ | + | + | + | G350A | G117D |
| L59 | $M_3$ | + | + | + | G350A | G117D |
| L68 | $M_3$ | + | + | + | G350A | G117D |
| L75 | $M_3$ | + | + | + | G350A | G117D |
| L19 | $M_3$ | + | + | + | G805A | V267I |
| L64 | $M_3$ | + | + | + | G805A | V267I |
| L70 | $M_3$ | + | + | + | G805A | V267I |
| L91 | $M_3$ | + | + | + | G805A | V267I |
| L80 | $M_3$ | + | + | + | C1560T | L421F |
| L38 | $M_3$ | + | + | + | C1968T | Q557* |
| G4 | $M_3$ | + | + | + | C603T | A201A |
| L10 | $M_3$ | + | + | + | C843T | F281F |
| G1 | $M_4$ | + | + | + | No | No |
| G2 | $M_4$ | + | + | + | No | No |
| G3 | $M_4$ | + | + | + | No | No |
| G6 | $M_4$ | + | + | + | No | No |
| G7 | $M_4$ | + | + | + | No | No |

TABLE 2-continued

Mutations of candidate genes in synthetic wheat mutants with high susceptibility to stripe rust[1]

| Mutant strain | Plant generation | RLK1 (RLK1-FP1/RP1) | RLK2 (RLK2-FP1/RP1) | Yr4DS (YR4DS-FP5RP5) | Yr4DS base substitution[2] | Yr4DS Amino acid substitution[3] |
|---|---|---|---|---|---|---|
| G8 | $M_4$ | + | + | + | No | No |
| G9 | $M_4$ | + | + | + | No | No |
| L22 | $M_3$ | + | + | + | No | No |
| L27 | $M_3$ | + | + | + | No | No |
| L31 | $M_3$ | + | + | + | No | No |
| L40 | $M_3$ | + | + | + | No | No |
| L43 | $M_3$ | + | + | + | No | No |
| L44 | $M_3$ | + | + | + | No | No |
| L52 | $M_3$ | + | + | + | No | No |
| L53 | $M_3$ | + | + | + | No | No |
| L56 | $M_3$ | + | + | + | No | No |
| L62 | $M_3$ | + | + | + | No | No |
| L66 | $M_3$ | + | + | + | No | No |
| L71 | $M_3$ | + | + | + | No | No |
| L73 | $M_3$ | + | + | + | No | No |
| S2 | $M_3$ | + | + | + | No | No |
| S5 | $M_3$ | + | + | + | No | No |
| S10 | $M_3$ | + | + | + | No | No |
| S14 | $M_3$ | + | + | + | No | No |
| S19 | $M_3$ | + | + | + | No | No |
| S20 | $M_3$ | + | + | + | No | No |
| S3 | $M_3$ | + | + | − | No | No |
| L14 | $M_3$ | + | − | − | No | No |
| L42 | $M_3$ | + | − | − | No | No |
| L54 | $M_3$ | + | − | − | No | No |
| L55 | $M_3$ | + | − | − | No | No |
| L58 | $M_3$ | + | − | − | No | No |
| L72 | $M_3$ | + | − | − | No | No |
| L85 | $M_3$ | + | − | − | No | No |
| L86 | $M_3$ | + | − | − | No | No |
| S11 | $M_3$ | + | − | − | No | No |
| S13 | $M_3$ | + | − | − | No | No |
| S17 | $M_3$ | + | − | − | No | No |
| S22 | $M_3$ | + | − | − | No | No |
| G5 | $M_4$ | − | − | − | No | No |
| L32 | $M_3$ | − | − | − | No | No |
| L63 | $M_3$ | − | − | − | No | No |
| L69 | $M_3$ | − | − | − | No | No |
| L89 | $M_3$ | − | − | − | No | No |
| S6 | $M_3$ | − | − | − | No | No |
| S7 | $M_3$ | − | − | − | No | No |
| S9 | $M_3$ | − | − | − | No | No |
| S25 | $M_3$ | − | − | − | No | No |

[1]The table describes the deletion and point mutation of three genes in Yr4DS region. ACTIN gene is used as an internal reference to evaluate the quality of DNA samples. The amplified primers include RLK1(RLK1-FP1 and RLK1-RP1), RLK2(RLK2-FP1 and RLK2-RP1), Yr4DS(YR4DS-FP5 and YR4DS-RP5) and ACTIN(Actin-FP and Actin-RP). "+" means positive PCR amplification; "−" means negative PCR amplification, reflecting the deletion of the whole or part of the target gene. The RLK2 and Yr4DS genes carried by the plants with positive target gene amplification were sequenced, there is no base mutation in the coding sequence of RLK2 gene of all individuals, but there is a base mutation in the coding sequence of Yr4DS gene.

[2]The left letter is the base of disease-resistant Yr4DS gene, the middle number represents the base position of cDNA level relative to the start codon ATG, and the right letter is the base after mutation.

[3]The left letter is the corresponding amino acid in the disease-resistant Yr4DS protein, the middle number represents the position relative to the first amino acid, and the right letter is the mutated amino acid.

TABLE 3 effect of different target gene expression on stripe rust resistance level of transgenic plants

| Classification | Carrier (enzyme digestion treatment) [1] | Independent transgenic line[2] | RLK1 | RLK2 | Yr4DS | Stripe rust reaction |
|---|---|---|---|---|---|---|
| G1 | PC1104 (I) | 2 + 3 | + | + | + | Disease-resistant |
| G2 | PC1104 (X1) | 1 | + | + | − | susceptible |
| G3 | PC1104 (I) | 1 | − | + | + | Disease-resistant |

TABLE 3-continued effect of different target gene expression on stripe rust resistance level of transgenic plants

| Classification | Carrier (enzyme digestion treatment) [1] | Independent transgenic line[2] | RLK1 | RLK2 | Yr4DS | Stripe rust reaction |
|---|---|---|---|---|---|---|
| G4 | PC1104 (X1, XK1) | 2 | + | − | − | susceptible |
| G5 | PC1104 (B1, N1, XK1) | 5 | − | + | − | susceptible |
| G6 | PC1104 (B1, N1, X1) | 7 + 2 | − | − | − | susceptible |

[1]Firstly, the plasmid PC1104 was digested with restriction enzymes, and then used for the transformation of wheat and barley. The restriction enzyme digestion treatment of the plasmid includes: non-restriction digestion (Intact = I), BsrGI digestion (B1), NotI digestion (1), XbaI digestion (X1), and XbaI + KpnI double digestion (XK1). The role of each gene in resistance to stripe rust is determined by detecting the expression of three genes in the Yr4DS region and the resistance to stripe rust of transgenic plants. The amplified primers include RLK1 (first round primers RPK1-FP1 and RLK1-RP2, second round primers RPK1-FP3 and RLK1-RP3), RLK2 (first round primers RPK2-FP2 and RLK2-RP2, second round primers RPK2-FP3 and RLK2-RP3), Yr4DS (TV1 first round primers YR4DS-FP6 and YR4DS-RP6, TV1 second round primers YR4DS-FP7 and YR4DS-RP7; TV4 first round primers YR4DS-FP8 and YR4DS-RP3, TV4 second round primers YR4DS-FP9 and YR4DS-RP9) and ACTIN (single round primers Actin-FP and Actin-RP). "+" represents expression; represents non expression.

[2]For double numbers, the number before plus sign represents the number of independent transgenic lines of wheat, and the number behind plus sign represents the number of independent transgenic lines of barley. For a single number, it only represents the number of independent transgenic lines of wheat.

Embodiment 1: Transcriptomics is Used to Identify the Genes Specifically Expressed in Stripe Rest Resistant Parents and BSA Pool In the present invention, RNA sequencing (RNA-seq) and Bulked Segregant Analysis (BSA) are used to compare the leaf transcriptome of the stripe rust resistant BSA pool and the stripe rust susceptible BSA pool of the $F_6$ generation of the *Aegilops tauschii* isolated population at the adult stage. RNA sequencing uses high-throughput sequencing technology to directly determine the sample cDNA molecules. In the present invention, RNA sequencing is used to compare the transcriptome of leaves in adult stage of BSA disease-resistant pool (Rpool) and BSA susceptible pool (Spool), wherein the Rpool is composed of stripe rest resistant *Aegilops tauschii* parent PI511383, stripe rust susceptible *Aegilops tauschii* parent PI486274 and 12 stripe rust-resistant strains in $F_6$ generation homozygous strains derived from stripe rust resistant *Aegilops tauschii* parent PI511383 and stripe rust susceptible *Aegilops tauschii* parent PI486274, the Spool is composed of 11 stripe rust susceptible strains. A biological repeat is determined separately for different samples. Total RNA is extracted by TRIzol reagent and related methods/Life Technologies, Grand Island, N.Y., USA). The library construction (preferably about 500 bp mRNA fragments) and high-throughput double-ended sequencing/HiSeq 2500, Illumina, San Diego, Calif., USA; paired-end, PE125) involved in RNA sequencing are undertaken by Berry Genomics Company, Beijing, China.

Figure 2:
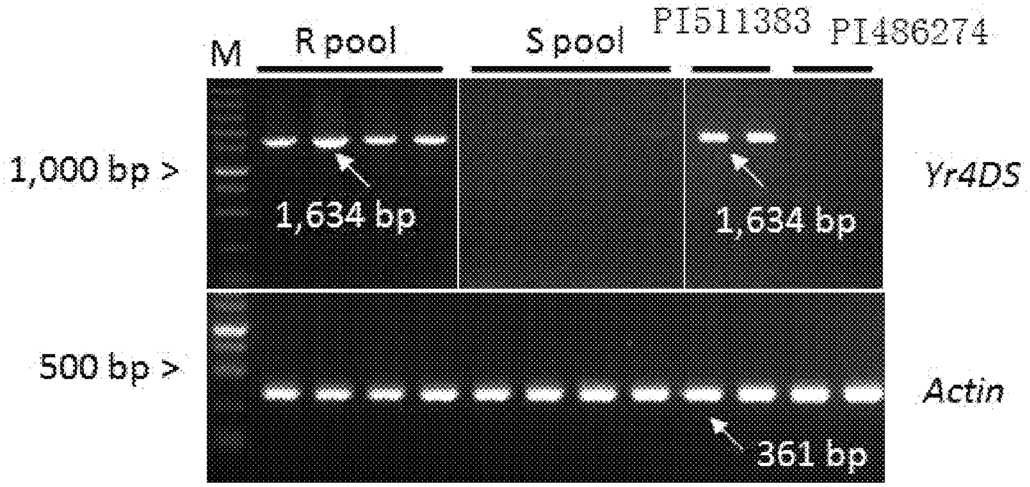
FIG. 2: the expression of Yr4DS gene in leaves of *Aegilops tauschii* at Adult Stage; in which Rpool and Spool represent the $F_6$ generation homozygous lines that constitute the disease-resistant pool and the susceptible pool respectively; in the upper part of FIG. 2, the expression of Yr4DS cDNA was detected by RT-PCR, the samples include stripe rust resistant *Aegilops tauschii* parent PI511383, stripe rust susceptible *Aegilops tauschii* parent PI486274, BSA disease-resistant pool (R pool, which includes 12 strains, each strain shows Yr4DS cDNA positive, and only 4 of them are shown here) and BSA susceptible pool (S pool, including 11 strains, each strain shows Yr4DS cDNA negative, only 4 strains are shown here), BSA disease resistant pool and BSA susceptible pool are composed of stripe rust resistant *Aegilops tauschii* parent PI511383, stripe rust susceptible *Aegilops tauschii* parent PI486274 and $F_6$ generation homozygous strains derived from stripe rust resistant *Aegilops tauschii* parent PI511383 and stripe rust susceptible *Aegilops tauschii* parent PI486274. RT-PCR detection is applied to PCR primers Yr4DS-FP4 and Yr4DS-RP4 (Table 1). In the lower part of FIG. 2, RT-PCR is used to test the expression of Actin gene (endogenous reference) of *Aegilops tauschii* in the corresponding samples, and applied to the PCR primers Actin-FP and Actin-RP (Table 1).

For the original data of RNA-seq. firstly, the adapter information, low-quality bases (bases with Q value ≤3, accounting for more than 50% of the whole read) and undetected bases (the ratio of N is more than 3%) are eliminated to obtain valid data; using Trinity software (Haas et al. 2013. Nature Protocols 8:1494-1512) to assemble effective data from scratch. By comparing the leaf transcriptome data of PI511383, PI486274, Rpool and Spool, it is found that individual genes are only expressed in stripe rust resistant parents PI511383 and Rpool. According to the present invention, an unknown gene is identified, the sequence of which is shown as SEQ ID NO: 1, SEQ ID NO: 3, SEQ ID NO: 5, SEQ ID NO: 7, SEQ ID NO: 9 or SEQ ID NO: 10; with primer combination Yr4DS-FP4/Yr4DS-RP4, it is detected that the gene is expressed in resistant parents PI511383 and resistant pool, but not expressed in susceptible parent PI486274 and susceptible pool (FIG. 2). Inventors predict that the gene (such as SEQ ID NO: 1, SEQ ID NO: 3, SEQ ID NO: 5, SEQ ID NO: 7, SEQ ID NO: 9 or SEQ ID NO: 10) may affect the resistance level of *Aegilops tauschii* to wheat swipe rust. By comparing the genome sequences of *Aegilops tauschii*, it is found that the gene is located on chromosome 4DS. The present invention temporarily named the gene as Yellow rust resistance gene 4DS (Yr4DS), and carried out functional research around the gene.

Embodiment 2: Verification of Full-Length cDNA of Yr4DS Gene of *Aegilops tauschii*

In order to verify the full-length cDNA of Yr4DS gene, TRIzol reagent was used to extract the total RNA of leaf of *Aegilops tauschii* PI511383 after 10 days of inoculation with stripe rust, and then the cDNA template was prepared by the RevertAid Frist Strand cDNA Synthesis kit (Thermo Scientific, Waltham, Mass., USA). The 5' and 3' ends of the full-length cDNA of Yr4DS gene (SEQ ID NO: 1 and 3) were isolated by rapid amplification of cDNA ends (RACE) and the SMARTer RACE cDNA Amplification kit (Clontech Laboratories, Mountain View, Calif., USA) was used, and the operation method was according to the kit instructions. The nested primers of 5'-end RACE PCR were Yr4DS-RP10 and Yr4DS-RP11, in which Yr4DS-RP11 was the nested primer of Yr4DS-RP10. The gene had two 3' ends, and the nested primers of the first 3' end RACE PCR were Yr4DS-FP10 and Yr4DS-FP11, in which Yr4DS-FR11 was the nested primer of Yr4DS-FP10. The nested primers of the second 3' end RACE PCR were Yr4DS-FP12 and Yr4DS-FP13, in which Yr4DS-FP13 was the nested primer of Yr4DS-FP12. Sequencing the RACE PCR products confirmed the integrity of both ends of the full-length cDNA sequence (such as SEQ ID NO: 1, SEQ ID NO: 3, SEQ ID NO: 5 or SEQ ID NO: 7j)of Yr4DS gene, which indicated that RNA sequencing and sequence assembly were highly reliable. The full-length cDNA TV1 (SEQ ID NO: 1) of Yr4DS gene was 4,266 bp in total, including an open reading frame (ORF) of 3,207 bp; there was one in-frame stop codon at the position 30 bp upstream of the start codon, indicating the current prediction ORE was reliable and representing an isoform of Yr4DS protein. The full-length cDNA TV2a (SEQ ID NO: 3) of the Yr4DS gene was 3,477 bp in total and contains an ORE of 1.277 bp, representing another isoform of the Yr4DS protein. The full-length cDNA TV3 (SEQ ID NO: 5) of the Yr4DS gene was 2,853 bp in total and contains an ORE of 1,488 bp, representing the third isoform of the Yr4DS protein. The full-length cDNA TV4 (SEQ ID NO: 1) of Yr4DS gene was 2,609 bp in total and contains an ORF of 1,416 bp, representing the fourth isoform of Yr4DS protein.

Embodiment 3: Construction and Screening of Fosmid Library of 'PI511383' Genome The Fosmid library of PI511383 genomic DNA is created for the convenience of cloning genomic DNA, and the construction method referred to published literature (Jetty. 2005. Theor Appl Genet 111: 1596-1607). Firstly, genomic DNA with high-molecular weight (HMW) was extracted from leaves of PI511383, and the genomic DNA with high-molecular weight was randomly "cut" into fragments with different sizes by repeated freezing and thawing (liquid nitrogen/45° C., 20-30 times). 1% agarose gel and pulsed-field gel electrophoresis (PFGE) free DNA fragment products were used to purify DNA fragments between 36-60 kb. Complement the DNA fragment with terminal repair enzyme, repeat pulsed-field gel electrophoresis and fragment purification steps, and clone the DNA fragment obtained by twice purification into Fosmid carrier pCC1FOS; after packed with phage extract, the host bacteria EPI300-T1R strain cells were infected. The host bacteria infected with phage was coated on LB plate containing 12.5 ug $ml^{-1}$ chloramphenicol, cultured overnight at 37° C., and Fosmid clones on the plate were collected.

The Fosmid library of PI511383 genome contains about 1 million clones and is stored in 622 super pools. According to the randomly selected 120 Fosmid clones, the library quality is tested, and the empty rate of the library is 0, the monoclonal average insert fragment is 35 kb, covering about 8.2 times of the whole genome of *Aegilops tauschii* (calculated by 4.3 Gb). To obtain Fosmid done carrying Yr4DS gene, several sets of PCR primers are designed according to The full-length cDNA TV1 (SEQ ID NO: 1) of Yr4DS gene and reference sequence of *Aegilops tauschii* genome, the amplification effect of different primer combinations on *Aegilops tauschii* genome DNA is tested, and two pairs of primer combinations for library screening are determined: Yr4DS-FP1/Yr4DS-RP1 and Yr4DS-FP14/Yr4DS-RP14. A 727 bp band is amplified by Yr4DS-FP1/Yr4DS-RP1 from the *Aegilops tauschii* Clae9 and PI511383 resistant to stripe rust (FIG. 1), while no specific band is amplified in *Aegilops tauschii* PI486274 and PI560536 susceptible to stripe rust, but a 575 bp band is amplified from *Aegilops tauschii* AL8/78 susceptible to stripe rust. To verify the relationship between the marker and stripe rust resistance of *Aegilops tauschii*, the invention detects more than 6,000 isolated individuals from *Aegilops tauschii* combinations (PI486274/PI511383, AS2388/AS87), and the marker (727 bp band) and stripe rust resistance phenotype complete linkage. In order to further determine the validity of this marker, 175 samples of *Aegilops tauschii* germ plasm are screened, in which a 727 bp band is amplified from 69 resistant *Aegilops tauschii*, a 575 bp band is amplified from 35 susceptible *Aegilops tauschii*, and 71 susceptible *Aegilops tauschii* have no specific amplified bands. The genotype of this marker is completely consistent with the resistance to stripe rust of existing *Aegilops tauschii* germplasm. Therefore, Yr4DS-FP1/Yr4DS-RP1 can be used as a reliable marker for diagnosing stripe rust resistance phenotype of *Aegilops tauschii*, which is named Yr4DS-PM (promoter-derived marker). In addition, specific molecular markers named Yr4DS-GM (gene-derived marker) and Yr4DS-TM (terminator-derived marker) are designed for YR4DS gene region and terminal region (FIG. 1), which can be used as reliable markers for diagnosing stripe rust resistance phenotype of *Aegilops tauschii*.

Figure 4:
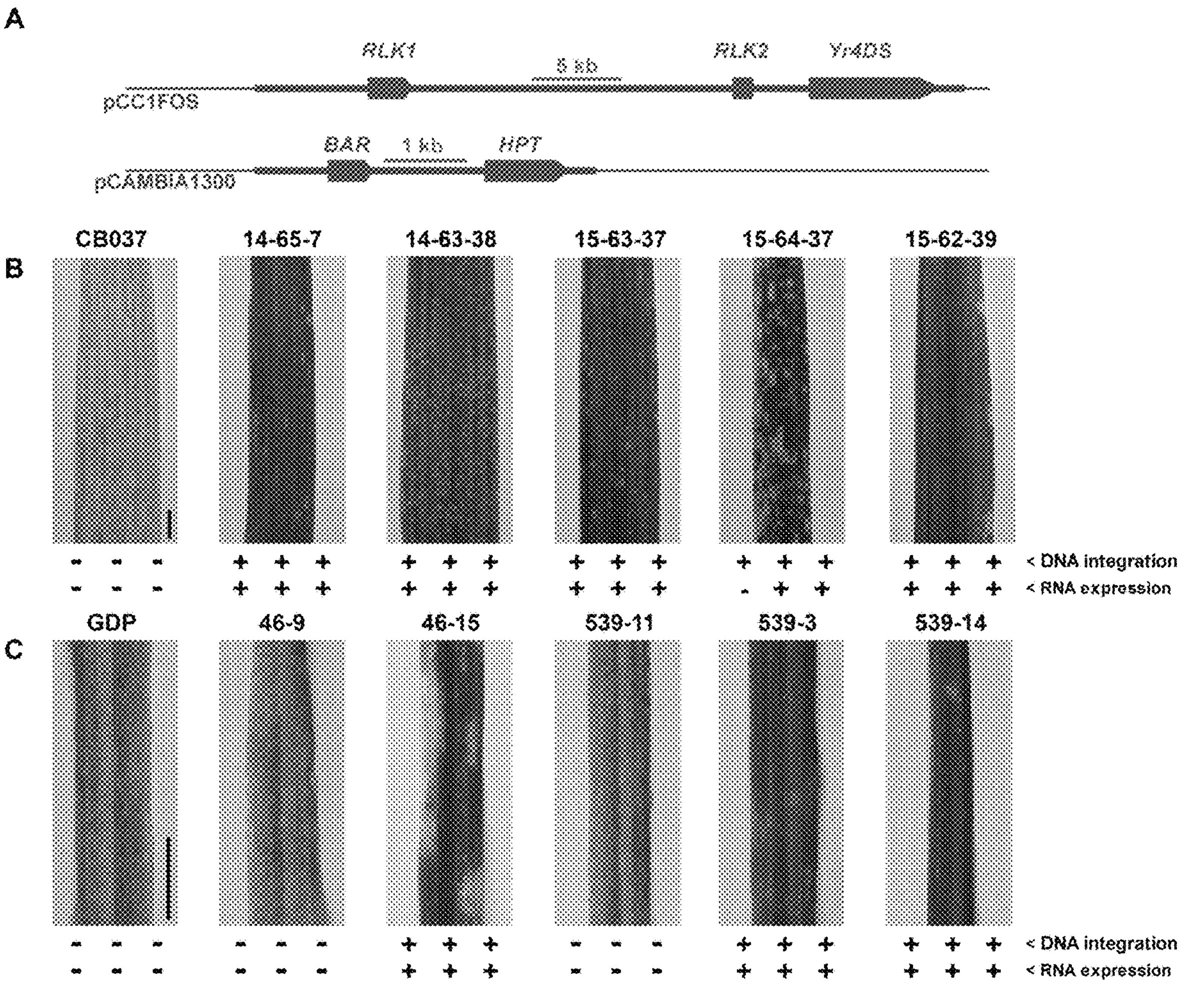
FIG. 4: A graph showing the genetic complementation of Yr4DS and other genes by using wheat 'CB037' and barley 'Golden Promise'; in which FIG. A) shows the plasmid carrying the full-length expression cassettes (SEQ ID NO: 5) of Yr4DS and other genomes, the plasmid backbone is pCC1FOS, and the red line represents the carrier segment. Co-transformation carrier is PC174, which carries the herbicide screening marker BAR gene, and the plasmid backbone is pCAMBIA1300. FIG. B) shows the reaction of transgenic wheat plants after inoculation, and the integration and expression of three genes in the plants were verified by PCR. The three genes arranged as RLK1 (left), RLK2 (middle) and Yr4DS (right). FIG. C) shows the reaction of transgenic barley plants after inoculation, which also detects the integration and expression of three genes (left RLK1, middle RLK2 and right Yr4DS), the "+" means integration or expression, and the "−" means non-integration or non-expression. The wheat 'CB037' and barley 'Golden Promise (GDP)' are non-GM wild type control. Scale bar=1 cm.

With Yr4DS-PM labeling, 622 super pools of PI511383 Fosmid library are screened by bacterial liquid PCR. Firstly, the super pool where the positive Fosmid monoclonal is located is confirmed, and then the positive Fosmid monoclonal is obtained by dilution screening step by step, and a total of 10 independent monoclonal antibodies are screened. Then, the primer Yr4DS-FP15/YR4DS-RP15 of YR4DS gene is used for further screening to obtain 8 independent monoclonal antibodies. Clone F2-1 (i.e., plasmid PC1104) carries an insert fragment of 39,535 bp (SEQ ID NO: 10; FIG. 4A), the sequence has three expressed genes, which are receptor-like kinase gene 1 (RLK1), receptor-like kinase gene 2 (RLK2) and Yr4DS.

Embodiment 4: Creation of EMS Mutant Group of 'Synthetic Wheat'

In order to confirm the function of the disease-resistant Yr4DS gene, the synthetic wheat Syn-SAU-93( AS2382/AS2388) was treated with the chemical mutagen ethyl methane sulfonate (EMS) aqueous solution (Zhang et al. 2010. Euphytica 172: 285-294). The previous results showed that AS2388 and PI511383 carry the same disease resistance gene (Liu et al. 2013. Crop Science 53: 2014-2020); actually, their Yr4DS gene sequences (such as SEQ ID NO: 1, SEQ ID NO: 3, SEQ ID NO: 5, SEQ ID NO: 7, SEQ ID NO: 9 or SEQ ID NO: 10) were identical. The mutant population was created as follows: a total of 1,850 seeds are treated, 200 seeds per 100 ml of EMS water solution (78 mM) were treated, placed on a horizontal shaker for 12 hours (150 rpm, 25° C.), and then washed with water for 12 hours at room temperature; the washed seeds were simply dried by airing and then sown to the experimental field of the Wheat Research Institute of Sichuan Agricultural University, and a total of 613 $M_2$ strains were obtained.

Embodiment 5: Screening the Mutant Population of Synthetic Wheat and Confirming the Mutation and Function of Yr4DS and Other Genes $M_3$ or $M_3$ seeds derived from all $M_2$ strains were mixed and planted in the experimental field of Wheat Research Institute of Sichuan Agricultural University, and the current popular stripe rust mixed physiological races, including CYR30, CYR31, CYR32, CYR33, CYR34, Gui 22-1, SY11-4 and HY46-8, were used for inoculation at seedling stage; and identification of synthetic wheat mutants susceptible to stripe rust was carried out after the full incidence of the susceptible control. The genomic DNA of susceptible plants was extracted with Sodium lauroylsarcosinate (Sarkosyl) method (Yuan et al. 2012. Journal of Genetics and Genomics 39: 587-592), and the DNA concentration was determined by NanoDrop™ One ultramicro spectrophotometer (Thermo Fisher Scientific, Madison, Wis., USA), and adjusted uniformly to 100 ng $ul^{-1}$. By using PCR amplification technology, Yr4DS gene was cloned by using mutant DNA with high susceptibility to stripe rust as template. The 3,956 bp region in the Yr4DS gene is divided into three amplifications: the first segment uses PCR primers Yr4DS-FP16 and Yr4DS-RP16. the second segment uses PCR primers Yr4DS-FP17 and Yr4DS-RP17, and the third segment uses PCR printers Yr4DS-FP5 and Yr4DS-RP5; the PCR reaction conditions are as follows: initial denaturation 94° C., 3 min, 10 cycles (denaturation 94° C., 30 sec;

annealing at 65° C. each cycle drops 0.5° C., 30 sec; and the extension is 72° C., 105 sec); 28 cycles (denaturation 94° C., 30 sec; annealing 60° C., 30 sec; extension 72° C., 105 sec), and the final extension is 72° C., 6 min. In addition, the variations of RLK1 and RLK2 genes close to Yr4DS in mutants with high susceptibility to stripe rust were detected, and PCR primers RLK1-FP1 and RLK1-RP1, RLK1-FP4 and RLK1-RF4, RLK2-FP4 and RLK2-RP1 were used (Table 1). PCR amplification products were commissioned to Sangon Biotech (Shanghai) (Sangon Biotech, Chengdu, China) for sequencing.

Figure 3:
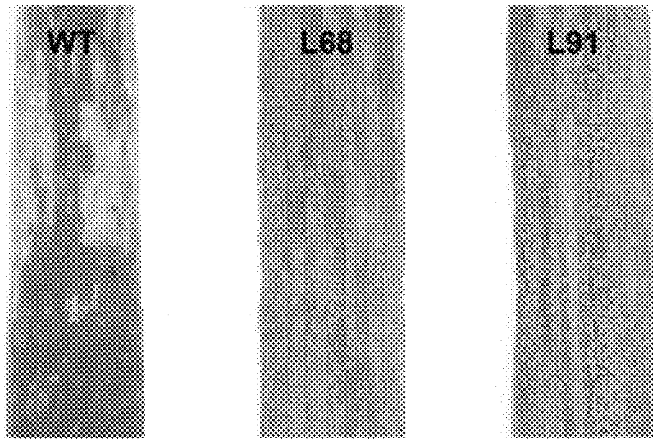
FIG. 3: the mutation of disease-resistant Yr4DS gene leads to the high susceptibility of synthetic wheat to wheat stripe rust at the adult stage. In the figure, L68 and L91 are $M_3$ generation EMS mutants of synthetic wheat (Syn-SAU-93, carrying disease-resistant Yr4DS gene) (Table 2), which are highly susceptible to wheat stripe rust (infection type is between 8 and 9). The corresponding wild-type control (WT) shows middle resistance to wheat stripe rust (infection type is between 3 and 4). Scale bar=1 cm.

In $M_3$ or $M_4$ mixed generation, 60 synthetic wheat plants with high susceptibility to wheat stripe rust were detected (Table 2, FIG. 3). Through the detection of 3 genes in the Yr4DS region, it was found that 22 mutants had Yr4DS gene deletions, in which 21 mutants had deletions extended to the RLK2 gene; there were 9 mutants in the plants with RLK2 and Yr4DS deletion, and the deletion extended to RLK1 gene. However, in all 60 mutants highly susceptible to wheat stripe rust, no deletion of RLK1 or RLK2 genes was found. The Yr4DS gene deletion accounted for 36% of all plants, similar to the 29% target gene deletion revealed by Ni et al. (Ni et al. 2017. Nature Communications 8:15121). Comparing the deletion of RLK1, RLK2 and Yr4DS, the deletion of Yr4DS gene may cause the loss of resistance to stripe rust in synthetic wheat.

For the 38 mutant plants with high susceptibility to stripe rust without deletion of Yr4DS gene, 10 of them had point mutation of Yr4DS gene, which caused single amino acid change or early termination of protein translation. According to other people's research, when 0.8% EMS (or 78 mM) is used to treat common wheat, the average step size of point mutation in each mutant is about 30 kb (Krasileva et al. 2017. PNAS 114: E913-921). Assuming that the Yr4DS gene has nothing to do with wheat resistance to stripe rust ($H_0$ hypothesis), in the remaining 38 individuals highly susceptible to stripe rust, theoretically 5 (=38×3.956+30; Yr4DS gene detection region is 3,956 bp) strains of Yr4DS gene mutation will be found, and the other 33 strains did not have mutations in the detected segment of the Yr4DS gene. In reality, among 38 individuals with high susceptibility to stripe rust, 28 plants did not find the effective point mutation of Yr4DS gene, but the other 10 plants had the effective point mutation of Yr4DS gene. Based on this, a chi-square goodness-of-fit test was carried out ($\chi^2$=5.8, df=1, P=0.016), and the $H_0$ hypothesis was overturned at the significance level of $\alpha$=0.05. Therefore, the Yr4DS gene affects the resistance level of *Aegilops tauschii* to stripe rust. In addition, the RLK2 gene in highly susceptible stripe rust mutants was also determined, which was located less than 3 kb away from the centromere of Yr4DS gene, but no effective point mutation was found. In contrast, the mutation frequency of Yr4DS gene was 26.3% in mutants with Yr4DS gene but high susceptibility to stripe rust. It can be seen that the Yr4DS gene affects the resistance level of *Aegilops tauschii* to stripe rust.

Embodiment 6: Acquisition, Phenotypic Analysis and Molecular Verification of transgenic Wheat and Barley In order to carry out the genetic complementary experiment of wheat, the genetic transformation of Fosmid F2-1 (or plasmid PC1104 with insertion sequence of SEQ ID NO: 10; FIG. 4A) carrying Yr4DS gene was carried out, and co-transformation carrier PC174 (FIG. 4A) was used. The co-transformation carrier carry a Bar screening mark (Block et al. 1987. The EMBO Journal 6:2513-2518). PC1104 carries three genes: RLK1, RLK2 and Yr4DS, in order to obtain transgenic plants with individual gene expression. PC1104 was treated respectively with restriction enzymes (including BsrGI, NotI, XbaI and KpnI+XbaI) (New England Biolabs, USA), and then the genetic co-transformation of enzyme digestion products was carried out.

Wheat immature embryo culture and transformation by biolistics bombardment refer to the procedure of Lv et al (Lv et al. 2014. PLoS ONE 9:e94171). Wherein, the carrier PC1104 of Yr4DS gene and the co-transformation carrier PC174 are mixed in a molar ratio of 3:1. The present invention selects wheat 'CB037' and barley 'Golden Promise' which can be infected with stripe rust as the transformation recipients. For wheat transformation, the immature embryos about 7-14 d after flowering were sterilized on the surface of the immature embryos. Firstly, treated with 70% alcohol (containing 0.05% Tween-20) for 5 minutes, and then treated with 20% Clorox's bleaching solution (Clorox® Regular Bleach, Oakland, Calif., USA; additional 0.05% tween-20 was added) for 15 min, and finally rinsed with sterilized water for 3-5 times. Peel off immature embryos (the length of immature embryos is 1-1.5 mm) on an ultra-clean table, and placed the scutellum upward on the induction medium (MS basic medium 4.3 $gL^{-1}$, maltose 40 $gL^{-1}$, vitamin $B_1$ 0.5 $mgL^{-1}$, aspartic acid 0.15 $gL^{-1}$, 2.4-D 2 $mg^{-1}$, copper sulfate 0.78 $mgL^{-1}$, phytagel 2.5 $gL^{-1}$, pH 5.8), cultured in dark at 22-23° C. for 4-6 d. The immature embryos were transferred to hypertonic medium (i.e., induction medium+sucrose 171.15 $gL^{-1}$, pH 5.8) and treated for 4 h, followed by biolistics bombardment. After the bombardment treatment for 20 h, the immature embryos were transferred to a recovery medium (equivalent to an induction medium) and cultured in the dark at 22-23° C. for 2 wk. Transfer embryogenic callus derived from immature embryos to differentiation medium (ie. induction medium+ 6-benzylaminopurine 0.1 $mgL^{-1}$+bialaphos 3 $mgL^{-1}$, pH 5.8), cultured for 2 wk at 22-23° C. and 16 h light (25 $\mu molm^{-2}s^{-1}$). Transfer the differentiated regenerated seedlings (height 2-3 cm) to rooting medium (MS basic medium 2.15 $gL^{-1}$, maltose 20 $gL^{-1}$, vitamin $B_1$ 0.25 $mgL^{-1}$, aspartic acid 0.075 $gL^{-1}$, 2,4-D 1 $mgL^{-1}$, copper sulfate 0.39 $mgL^{-1}$, phytagel 2.5 $gL^{-1}$, bialaphos 3 $mgL^{-1}$, pH 5.8), and cultured under the same environmental conditions. After the roots of the regenerated seedlings are fully developed, converted to potted plants and planted under greenhouse conditions.

PDS-1000/He tabletop gene gun (Bio-Rad Laboratories, Hercules, Calif., USA) was used for bombardment treatment. The preparation steps for bombarding the particle mixture are as follows: add 2 mg gold powder (diameter 0.6 $\mu$m) into a 1.5 ml silicified centrifuge tube, then add 35 $\mu$l absolute ethyl alcohol, shake and mix well, centrifuge and collect (12,000 rpm, 5 sec), and discard the supernatant; add 200 $\mu$l sterilized water precooled by ice, shake and mix well, centrifuge and collect (12,000 rpm, 5 sec), and discard the supernatant; adding 20 $\mu$g plasmid DNA (the concentration is about 1 $\mu g\mu l^{-1}$), then add the sterilized water precooled by ice to 245 $\mu$l, shake and mix well; then add 250 $\mu$l calcium chloride precooled by ice (2.5 M), shake and mix well; at last, add 50 $\mu$l spermidine (1.45%, v/v), shake at 4° C. for 15-20 min, centrifuge and collect (12,000 rpm, 10 sec), and discard the supernatant; and then add 36 $\mu$l absolute ethanol precooled by ice, shake and mix well. 10 $\mu$l gold powder and DNA suspension were sucked into the center of the carrier film, and after aseptic air drying, the carrier film (with gold powder side down) is placed into the microcarrier launch assembly, which is located 3 cm below the splittable film (1,100 psi). Place the bombarded callus on a hypertonic medium (area with a diameter of about 3.5 cm), and then place it 6 cm below the carrier membrane. The use of PDS-1000/He gene gun refers to the instrument manual, and the bombardment parameters are 1,300 psi (bombardment pressure) and 25 mm Hg (vacuum degree).

Figure 5:
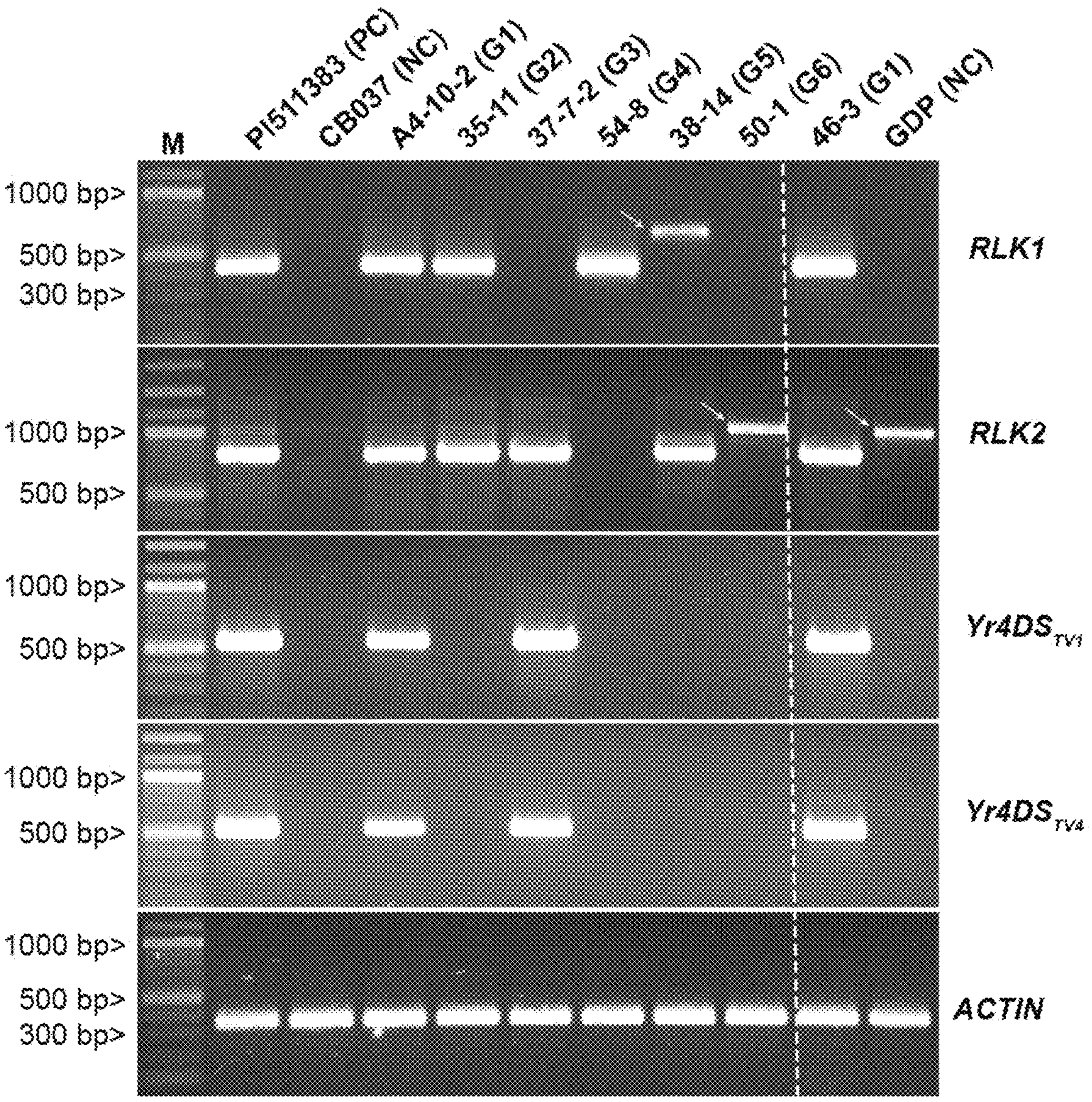
FIG. 5: the full-length expression of RLK1, RLK2 and Yr4DS genes in transgenic wheat and barley plants; the figure shows the expression of three genes in different types of transgenic plants (G1-G6) targeting the PC1104 plasmid, the different types of which refereed to Table 3. Two-round of PCR used to detect the expression of target genes: the first round uses long-span PCR primers to enrich the full-length transcripts of the target and its homologous genes, and the second round uses specific PCR primers to amplify only the transcripts of three target genes. For Yr4DS gene, two types of full-length transcripts, Yr4DS$_{TV1}$ and Yr4DS$_{TV4}$, are detected simultaneously. In addition, ACTIN gene is used as an internal reference control, which only needed one round of PCR. On the left side of the dotted line are wheat plants and on the right side are barley plants. PI511383 is a wild-type positive control (PC). CB037 and GDP are wild-type negative controls (NC). The white arrow in the figure indicates amplification products of genomic copies or other non-specific amplified products. M represents the molecular weight standard sample. Scale bar=1 cm.

In the present invention, a total of 8,380 wheat immature embryos were bombarded (including 1,590 immature embryos which were not treated with enzyme-digested PC1104 plasmid and 6,790 immature embryos which were treated with enzyme digested PC1104 plasmid), and 222 strains from 170 immature embryos were successfully obtained through tissue culture, screening and transplanting. PCR primers were used to detect the integration of RLK1 (RLK1-FP5 and RLK1-RP5), RLK2 (RLK2-FP3 and RLK2-RP4) and Yr4DS (YR4DS-FP1 and YR4DS-RP1, YR4DS-FP3 and YR4DS-RP3) in 222 strains. Furthermore, RT-PCR primers, RLK1 (first round primers RLK1-FP1 and RLK1-RP2; second round primers RLK1FP3 and RLK1-RP3), RLK2 (first round primers RLK2-FP2 and RLK2-RP2; second round primers RLK2-FP3 and RLK2-RP3) and Yr4DS (TV1 first round primers YR4DS-FP6 and YR4DS-RP6, second round primers YR4DS-FP7 and YR4DS-RP7; TV4 first round primers YR4DS-FP8 and YR4DS-RP3, second round primers YR4DS-FP9 and YR4DS-RP9) were used to confirm the expression of each target gene (see Table 3, FIG. 5). RT-PCR primers (Actin-FP and Actin-RP) were also used to confirm the expression of endogenous reference ACTIN gene. According to the test of wheat stripe rust, only two lines expressing Yr4DS transgene have high resistance to wheat stripe rust in the progenies of all 222 strains (see Table 3, FIG. 4 and FIG. 5). Overall, the expression of Yr4DS genome full-length expression framework (SEQ ID NO: 10) provides wheat with high resistance to stripe rust, and transforms susceptible wheat into stripe rust resistant wheat.

The PC1104 plasmid without enzyme digestion was co-transformed in barley, and the transformation steps were similar to those in wheat, but the methods of Hao et al. (Hao et al. 2018. Molecular Plant Pathology 19:1995-2010) were used for tissue culture, regeneration and screening. After biolistics bombardment, the treated immature embryos were transferred to the induction screening medium and cultured in the dark at 24° C. for 14 d; transferring the differentiated callus immature embryos to the induction screening medium, performing subculture screening culture, and culturing in the dark at 24° C. for 14 d; the bright yellow embryogenic callus were selected and transferred into the induction and screening medium for subculture and screening, and cultured in darkness at 24° C. for 14 d; the vigorous callus were transferred to the transition medium to induce callus differentiation and regeneration, after 5-10 d of culture, green buds could be regenerated, the culture conditions was 24° C., weak light, and light intensity was 2 μ mol $m^{-2}s^{-1}$; after 14 d, the callus was transferred to regeneration medium, and the culture conditions was 24° C., 16 light/8 h dark, and the light intensity was 35 μmol $m^{-2}s^{-1}$; after about 14 d, the strong regenerated seedlings were transferred to rooting medium, and the culture conditions are the same as the previous step; transplanting the regenerated seedlings to the greenhouse for planting after the roots of the regenerated seedlings develop well.

The various media used in barley tissue culture are as follows: a) the medium for induction includes MS salt 4.3 g $L^{-1}$, maltose 30 g $L^{-1}$, casein enzymatic hydrolysate 1 g $L^{-1}$, solution A 10 mL $L^{-1}$, phytagel 3.5 g $L^{-1}$, pH=5.8, hygromycin 25 mg $L^{-1}$ was added after autoclaving (121° C., 15 min); b) transition medium includes MS salt 2.7 g $L^{-1}$, maltose 20 g $L^{-1}$, glutamic acid 0.75 g $L^{-1}$, solution B 5 mL $L^{-1}$, phytagel 3.5 g $L^{-1}$, pH=5.8, and hygromycin 25 mg $L^{-1}$, 2,4-D 2.5 mg $L^{-1}$ and 6BA 0.1 mg $L^{-1}$ were added after autoclaving; c) the regeneration medium includes MS salt 2.7 g $L^{-1}$, maltose 20 g $L^{-1}$, glutamic acid 0.75 g $L^{-1}$, solution B 5 mL $L^{-1}$, phytagel 3.5 g $L^{-1}$, pH=5.8, and hygromycin 25 mg $L^{-1}$ was added after autoclaving; d) rooting medium includes MS salt 4.3 g $L^{-1}$, maltose 30 g $L^{-1}$, casein enzymatic hydrolysate 1 g $L^{-1}$, solution A 10 mL $L^{-1}$, phytagel 3.5 g $L^{-1}$, pH=5.8, and hygromycin 25 mg $L^{-1}$ was added after autoclaving. Solution A is inositol 35 g $L^{-1}$, proline 69 g $L^{-1}$, copper sulfate 0.12 g $L^{-1}$, VB1 0.1 g $L^{-1}$, pH=5.8. Solution B is ammonium nitrate 33 g $L^{-1}$, inositol 20 g $L^{-1}$, VB1 0.08 g $L^{-1}$, pH=5.8.

In the present invention, 2,200 barley immature embryos were bombarded, and 540 strains from 300 immature embryos were successfully obtained through tissue culture, screening and transplanting. The integration and expression of RLK1, RLK2 and Yr4DS in 540 strains were detected by PCR primers introduced from wheat (see Table 3, FIG. 5): in addition, Actin-FP and Actin-RP were used to confirm the expression of endogenous reference ACTIN gene. By testing the barley stripe rust strain PSH-72, among the descendants of 5 positive transgenic lines, all 3 lines expressing Yr4DS transgenic expression were highly resistant to barley stripe rust (see Table 3, FIG. 4 and FIG. 5).

In summary, the expression of Yr4DS genome full-length expression framework (SEQ ID NO: 10) provides high resistance to stripe rust in wheat and barley, and transforms susceptible wheat and barley into stripe rust resistant wheat and barley, respectively. Thus, introducing the full-length expression framework of Yr4DS genome (SEQ ID NO: 10) into wheat and other triticeae plants can create plants with high resistance to stripe rust, which will play a role in breeding wheat and other triticeae plants with resistance to stripe rust.

The above are only preferred embodiments of the application, and are not used to limit the application, and for those skilled in the art, the application can be variously modified and varied. Any modification, equivalent substitution, improvement and the like made within the spirit and principle of the application shall be included in the protection scope of the application.

The invention claimed is:

1. A transgenic Triticeae plant cell comprising a heterologous stripe rust resistance gene encoding SEQ ID NO: 2.

2. The transgenic Triticeae plant cell of claim 1, wherein the stripe rust resistance gene comprises SEQ ID NO: 1.

3. The transgenic Triticeae plant cell of claim 1, wherein the transgenic Triticeae plant cell is a wheat cell.

4. The transgenic Triticeae plant cell of claim 1, wherein the transgenic Triticeae plant cell is a barley cell.

5. A transgenic Triticeae plant comprising cells that are each the transgenic Triticeae plant cell of claim 1.

6. The transgenic Triticeae plant of claim 5, wherein the transgenic Triticeae plant is resistant to stripe rust due to expression of the stripe rust resistance gene.

7. The transgenic Triticeae plant of claim 5, wherein the transgenic Triticeae plant is wheat.

8. The transgenic Triticeae plant of claim 5, wherein the transgenic Triticeae plant is barley.

9. A recombinant expression vector comprising a promoter, a stripe rust resistance gene encoding SEQ ID NO: 2, and a terminator.

10. The recombinant expression vector of claim 9, wherein the stripe rust resistance gene comprises SEQ ID NO: 1.

11. A transgenic cell comprising the recombinant expression vector of claim 9.

12. The transgenic cell of claim 11, wherein the transgenic cell is a transgenic Triticeae plant cell.

13. A genetically engineered bacterium comprising the recombinant expression vector of claim 9.

14. A PCR marker for identifying the wheat stripe rust resistance gene in the plant of claim 1, wherein the PCR marker comprises SEQ ID NO: 62.

15. The PCR marker of claim 14, wherein the PCR marker is amplified with a first primer comprising SEQ ID NO: 13 and a second primer comprising SEQ ID NO: 14.

16. A method for breeding stripe rust resistance in a wheat or barley plant, wherein the method comprises:

breeding plants wherein each plant is the transgenic Triticeae plant of claim 5; and wherein the stripe rust resistance gene is expressed in the plants.

17. A method for obtaining a plant cell carrying the stripe rust resistance gene, wherein the method comprises:

transferring the recombinant expression vector of claim 9 into wheat or barley cells; and wherein the stripe rust resistance gene is expressed in the wheat or barley cells.

* * * * *